US007927830B2

(12) United States Patent
Cheung et al.

(10) Patent No.: US 7,927,830 B2
(45) Date of Patent: *Apr. 19, 2011

(54) MODIFIED CARBOCYANINE DYES AND THEIR CONJUGATES

(75) Inventors: Ching-Ying Cheung, San Ramon, CA (US); Stephen Yue, Eugene, OR (US); Wai-Yee Leung, San Ramon, CA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/129,671

(22) Filed: May 29, 2008

(65) Prior Publication Data

US 2009/0035810 A1 Feb. 5, 2009

Related U.S. Application Data

(60) Division of application No. 11/675,033, filed on Feb. 14, 2007, now Pat. No. 7,671,214, which is a continuation of application No. 11/150,596, filed on Jun. 10, 2005, now Pat. No. 7,566,790, which is a division of application No. 09/969,853, filed on Oct. 1, 2001, now Pat. No. 6,974,873, and a division of application No. 09/968,401, filed on Sep. 29, 2001, now Pat. No. 6,977,305.

(60) Provisional application No. 60/276,870, filed on Mar. 16, 2001, provisional application No. 60/236,637, filed on Sep. 29, 2000.

(51) Int. Cl.
*G01N 1/30* (2006.01)
*G01N 33/68* (2006.01)
*G01N 33/53* (2006.01)

(52) U.S. Cl. .......... 435/40.5; 436/86; 436/94; 530/402; 536/55.3; 548/491; 548/465; 548/159; 548/427; 546/113; 546/115; 546/83

(58) Field of Classification Search .................. 435/40.5; 436/86, 94

See application file for complete search history.

(56) References Cited

U.S. PATENT DOCUMENTS

| | | |
|---|---|---|
| 2,993,791 A | 7/1961 | Coles et al. |
| 3,723,419 A | 3/1973 | Mee et al. |
| 3,864,644 A | 2/1975 | Lincoln et al. |
| 4,011,086 A | 3/1977 | Simson |
| 4,273,862 A | 6/1981 | Yoshida et al. |
| 4,711,955 A | 12/1987 | Ward et al. |
| 4,839,265 A | 6/1989 | Ohno et al. |
| 4,981,977 A | 1/1991 | Southwick et al. |
| 4,997,928 A | 3/1991 | Hobbs |
| 5,030,253 A | 7/1991 | Tokuhiro et al. |
| 5,047,519 A | 9/1991 | Hobbs et al. |
| 5,049,673 A | 9/1991 | Tsien et al. |
| 5,137,810 A | 8/1992 | Sizemore et al. |
| 5,171,534 A | 12/1992 | Smith et al. |
| 5,196,306 A | 3/1993 | Bobrow et al. |
| 5,208,148 A | 5/1993 | Haugland et al. |
| 5,268,486 A | 12/1993 | Waggoner et al. |
| 5,332,666 A | 7/1994 | Prober |
| 5,405,975 A | 4/1995 | Kuhn et al. |
| 5,436,134 A | 7/1995 | Haugland et al. |
| 5,453,505 A | 9/1995 | Lee |
| 5,453,517 A | 9/1995 | Kuhn et al. |
| 5,486,616 A | 1/1996 | Waggoner et al. |
| 5,487,502 A | 1/1996 | Liao |
| 5,496,700 A | 3/1996 | Ligler et al. |
| 5,516,911 A | 5/1996 | London et al. |
| 5,539,082 A | 7/1996 | Nielsen et al. |
| 5,556,959 A | 9/1996 | Brush |
| 5,567,588 A | 10/1996 | Gold |
| 5,569,587 A | 10/1996 | Waggoner |
| 5,569,766 A | 10/1996 | Waggoner et al. |
| 5,580,990 A | 12/1996 | Van Den Berg et al. |
| 5,583,001 A | 12/1996 | Bobrow et al. |
| 5,627,027 A | 5/1997 | Waggoner |
| 5,639,874 A | 6/1997 | Middendorf |
| 5,648,270 A | 7/1997 | Kuhn et al. |
| 5,659,025 A | 8/1997 | Engels |
| 5,668,268 A | 9/1997 | Tang |
| 5,679,785 A | 10/1997 | Engels |
| 5,684,142 A | 11/1997 | Mishra |
| 5,714,327 A | 2/1998 | Houthoff et al. |
| 5,714,386 A | 2/1998 | Roederer |
| 5,731,158 A | 3/1998 | Bobrow et al. |

(Continued)

FOREIGN PATENT DOCUMENTS

AU 69861 3/2001

(Continued)

OTHER PUBLICATIONS

U.S. Appl. No. 09/968,401, "Notice of Allowance mailed Apr. 13, 2005".
U.S. Appl. No. 09/968,401, "Notice of Allowance mailed Aug. 12, 2005".
U.S. Appl. No. 09/968,401, "Notice of Allowance mailed Sep. 29, 2005".
U.S. Appl. No. 09/968,401, "Office Action mailed Feb. 16, 2005".
U.S. Appl. No. 09/968,401, "Office Action mailed Mar. 17, 2005".
U.S. Appl. No. 09/968,401, "Office Action mailed Apr. 20, 2004".
U.S. Appl. No. 09/968,401, "Office Action mailed May 1, 2003".
U.S. Appl. No. 09/968,401, "Office Action mailed Jun. 3, 2002".
U.S. Appl. No. 09/968,401, "Office Action mailed Sep. 10, 2003".
U.S. Appl. No. 09/968,401, "Office Action mailed Nov. 15, 2002".

(Continued)

*Primary Examiner* — Yong Chu
(74) *Attorney, Agent, or Firm* — Life Technologies Corporation; James K. Blodgett

(57) ABSTRACT

Chemically reactive carbocyanine dyes incorporating an indolium ring moiety that is substituted at the 3-position by a reactive group or by a conjugated substance, and their uses, are described. Conjugation through this position results in spectral properties that are uniformly superior to those of conjugates of spectrally similar dyes wherein attachment is at a different position. The invention includes derivative compounds having one or more benzo nitrogens.

24 Claims, 13 Drawing Sheets

U.S. PATENT DOCUMENTS

| | | |
|---|---|---|
| 5,767,287 A | 6/1998 | Bobrow |
| 5,808,044 A | 9/1998 | Brush et al. |
| 5,831,098 A | 11/1998 | Ollmann |
| 5,853,969 A | 12/1998 | Harada et al. |
| 5,877,310 A | 3/1999 | Reddington et al. |
| 5,922,618 A | 7/1999 | Shigetou et al. |
| 5,965,713 A | 10/1999 | Shigeto et al. |
| 5,985,566 A | 11/1999 | Houthoff |
| 5,986,086 A | 11/1999 | Brush et al. |
| 6,002,003 A | 12/1999 | Shen et al. |
| 6,004,536 A | 12/1999 | Leung et al. |
| 6,008,373 A | 12/1999 | Waggoner et al. |
| 6,027,709 A | 2/2000 | Little et al. |
| 6,043,025 A | 3/2000 | Minden et al. |
| 6,048,982 A | 4/2000 | Waggoner et al. |
| 6,083,485 A | 7/2000 | Licha et al. |
| 6,086,737 A | 7/2000 | Patonay |
| 6,114,350 A | 9/2000 | Randall et al. |
| 6,127,134 A | 10/2000 | Minden et al. |
| 6,130,094 A | 10/2000 | Waggoner et al. |
| 6,133,445 A | 10/2000 | Waggoner et al. |
| 6,150,510 A | 11/2000 | Seela |
| 6,197,956 B1 | 3/2001 | Randall et al. |
| 6,204,389 B1 | 3/2001 | Randall et al. |
| 6,224,644 B1 | 5/2001 | Randall et al. |
| 6,225,050 B1 | 5/2001 | Waggoner |
| 6,245,499 B1 | 6/2001 | Suzuki et al. |
| 6,258,340 B1 | 7/2001 | Licha et al. |
| 6,303,758 B1 | 10/2001 | Shigetou et al. |
| 6,303,759 B1 | 10/2001 | Shigetou et al. |
| 6,342,326 B1 | 1/2002 | Milton |
| 6,538,129 B1 | 3/2003 | Terpetschnig et al. |
| 6,664,047 B1 | 12/2003 | Haugland et al. |
| 6,740,755 B2 | 5/2004 | Caputo et al. |
| 6,962,992 B2 | 11/2005 | Martin et al. |
| 6,972,326 B2 | 12/2005 | Haugland et al. |
| 6,974,873 B2 * | 12/2005 | Leung et al. ............. 548/455 |
| 6,977,305 B2 * | 12/2005 | Leung et al. ............. 548/450 |
| 7,250,517 B2 | 7/2007 | Terpetschnig et al. |
| 7,566,790 B2 | 7/2009 | Leung et al. |
| 7,671,214 B2 * | 3/2010 | Leung et al. ............. 548/450 |
| 7,790,893 B2 | 9/2010 | Leung et al. |
| 7,820,824 B2 | 10/2010 | Leung et al. |
| 2003/0138791 A1 | 7/2003 | Haalck et al. |
| 2006/0099638 A1 | 5/2006 | Leung et al. |
| 2007/0178511 A1 | 8/2007 | Leung et al. |
| 2007/0212767 A1 | 9/2007 | Bonyhadi et al. |
| 2007/0232805 A1 * | 10/2007 | Leung et al. ............. 546/116 |
| 2009/0035809 A1 | 2/2009 | Leung et al. |

FOREIGN PATENT DOCUMENTS

| | | |
|---|---|---|
| DE | 19937024 | 2/2001 |
| DE | 10046215 | 4/2004 |
| EP | 1065250 | 8/2004 |
| GB | 870753 | 7/1958 |
| JP | 05313304 | 11/1993 |
| JP | 06014984 | 1/1994 |
| WO | WO-93/04357 | 3/1993 |
| WO | WO-94/05688 | 3/1994 |
| WO | WO-96/17628 | 6/1996 |
| WO | WO-97/40104 | 10/1997 |
| WO | WO-98/48838 | 11/1998 |
| WO | WO-99/51702 | 10/1999 |
| WO | WO-99/64519 | 12/1999 |
| WO | WO-00/31534 | 6/2000 |
| WO | WO-00/75237 | 12/2000 |
| WO | WO-01/02374 | 1/2001 |
| WO | WO-01/11370 | 2/2001 |
| WO | WO-01/21624 | 3/2001 |
| WO | WO-02/26980 | 4/2002 |
| WO | WO-2004/039894 | 5/2004 |

OTHER PUBLICATIONS

U.S. Appl. No. 09/968,401, "Response to Feb. 16, 2005 Office Action", filed Mar. 1, 2005.

U.S. Appl. No. 09/968,401, "Response to Mar. 17, 2005 Office Action", filed Mar. 30, 2005.

U.S. Appl. No. 09/968,401, "Response to Apr. 20, 2004 Office Action", filed Oct. 20, 2004.

U.S. Appl. No. 09/968,401, "Response to May 1, 2003 Office Action", filed Jul. 28, 2003.

U.S. Appl. No. 09/968,401, "Response to Jun. 3, 2002 Office Action", filed Aug. 4, 2002.

U.S. Appl. No. 09/968,401, "Response to Sep. 10, 2003 Office Action", filed Nov. 13, 2003.

U.S. Appl. No. 09/968,401, "Response to Nov. 15, 2002 Office Action", filed Mar. 13, 2003.

U.S. Appl. No. 09/968,401, "Response to Office Action", filed Jul. 5, 2005.

U.S. Appl. No. 09/969,853, "Notice of Allowance mailed Apr. 27, 2005".

U.S. Appl. No. 09/969,853, "Notice of Allowance mailed Aug. 15, 2005".

U.S. Appl. No. 09/969,853, "Office Action mailed Feb. 9, 2005".

U.S. Appl. No. 09/969,853, "Office Action mailed Mar. 2, 2004".

U.S. Appl. No. 09/969,853, "Office Action mailed Mar. 17, 2005".

U.S. Appl. No. 09/969,853, "Office Action mailed May 3, 2004".

U.S. Appl. No. 09/969,853, "Office Action mailed on Mar. 10, 2003".

U.S. Appl. No. 09/969,853, "Office Action mailed on May 14, 2003".

U.S. Appl. No. 09/969,853, "Office Action mailed on Aug. 12, 2003".

U.S. Appl. No. 09/969,853, "RCE and Response, filed Jul. 5, 2005".

U.S. Appl. No. 09/969,853, "Response to Feb. 9, 2005 Office Action, filed Mar. 2, 2005".

U.S. Appl. No. 09/969,853, "Response to Mar. 2, 2004 Office Action, filed Mar. 18, 2004".

U.S. Appl. No. 09/969,853, "Response to Mar. 10, 2003 Office Action, filed on Apr. 3, 2003".

U.S. Appl. No. 09/969,853, "Response to Mar. 17, 2005 Office Action, filed Apr. 6, 2005".

U.S. Appl. No. 09/969,853, "Response to May 3, 2004 Office Action, filed Oct. 28, 2004".

U.S. Appl. No. 09/969,853, "Response to May 14, 2003 Office Action, filed on Jun. 10, 2003".

U.S. Appl. No. 09/969,853, "Response to Aug. 12, 2003 Office Action, filed Feb. 13, 2004".

U.S. Appl. No. 09/969,853, "Supp. Notice of Allowability mailed Sep. 23, 2005".

U.S. Appl. No. 11/150,596, "Notice of Allowance mailed Feb. 26, 2009".

U.S. Appl. No. 11/150,596, "Notice of Allowance mailed Jun. 15, 2009".

U.S. Appl. No. 11/150,596, "Office Action mailed Apr. 4, 2008".

U.S. Appl. No. 11/150,596, "Office Action mailed Nov. 7, 2008".

U.S. Appl. No. 11/150,596, "Office Action mailed Dec. 20, 2007".

U.S. Appl. No. 11/150,596, "RCE and Response to Nov. 7, 2008 Office Action, filed Jan. 7, 2009".

U.S. Appl. No. 11/150,596, "Response to Apr. 4, 2008 Office Action, filed Aug. 28, 2008".

U.S. Appl. No. 11/150,596, "Response to Dec. 20, 2007 Office Action, filed Jan. 22, 2008".

U.S. Appl. No. 11/313,890, "Notice of Allowance mailed Apr. 15, 2010".

U.S. Appl. No. 11/313,890, "Notice of Allowance Mailed Jul. 23, 2010".

U.S. Appl. No. 11/313,890, "Notice of Allowance mailed Apr. 15, 2010".

U.S. Appl. No. 11/313,890, "Office Action mailed Jan. 29, 2008".

U.S. Appl. No. 11/313,890, "Office Action mailed Jun. 3, 2008".

U.S. Appl. No. 11/313,890, "Office Action mailed Sep. 4, 2009".

U.S. Appl. No. 11/313,890, "Office Action mailed Sep. 29, 2008".

U.S. Appl. No. 11/313,890, "Office Action mailed Jun. 12, 2009".

U.S. Appl. No. 11/313,890, "Response to Jan. 29, 2008 Office Action", filed Mar. 28, 2008.

U.S. Appl. No. 11/313,890, "Response to Jun. 3, 2008 Office Action", filed Aug. 26, 2008.

U.S. Appl. No. 11/313,890, "Response to Jun. 12, 2009 Office Actiion", filed Aug. 12, 2009.

U.S. Appl. No. 11/313,890, "Response to Sep, 29, 2008 Office Action", filed Mar. 30, 2009.

U.S. Appl. No. 11/313,890, "Response to Office Action mailed Sep. 4, 2009 filed Mar. 3, 2010".
U.S. Appl. No. 11/675,030, "Office Action mailed Mar. 30, 2009".
U.S. Appl. No. 11/675,030, "Office Action mailed Apr. 7, 2008".
U.S. Appl. No. 11/675,030, "Office Action mailed Apr. 16, 2010".
U.S. Appl. No. 11/675,030, "Office Action mailed Aug. 7, 2008".
U.S. Appl. No. 11/675,030, "Office Action Mailed Oct. 20, 2009".
U.S. Appl. No. 11/675,030, "Response to Mar. 30, 2009 Office Action", filed Aug. 31, 2009.
U.S. Appl. No. 11/675,030, "Response to Apr. 7, 2008 Office Action", filed Jun. 9, 2008.
U.S. Appl. No. 11/675,030, "Response to Aug. 7, 2008 Office Action", filed Feb. 9, 2009.
U.S. Appl. No. 11/675,030, "Response to Restriction Requirement filed Feb. 22, 2010".
U.S. Appl. No. 11/675,033, "Notice of Allowance mailed Jan. 11, 2010".
U.S. Appl. No. 11/675,033, "Notice of Allowance mailed Dec. 4, 2009".
U.S. Appl. No. 11/675,033, "Office Action mailed May 2, 2008".
U.S. Appl. No. 11/675,033, "Office Action mailed May 13, 2009".
U.S. Appl. No. 11/675,033, "Response May 13, 2009 Office Action", filed Oct. 20, 2009.
U.S. Appl. No. 11/675,037, "Notice of Allowance mailed May 17, 2010".
U.S. Appl. No. 11/675,037, "Notice of Allowance mailed Sep. 7, 2010".
U.S. Appl. No. 11/675,037, "Office Action mailed Mar. 13, 2009".
U.S. Appl. No. 11/675,037, "Office Action mailed May 23, 2008".
U.S. Appl. No. 11/675,037, "Office Action mailed Aug. 1, 2008".
U.S. Appl. No. 11/675,037, "Office Action mailed Nov. 19, 2009".
U.S. Appl. No. 11/675,037, "Response to Mar. 13, 2009 Office Action", filed Aug. 13, 2009.
U.S. Appl. No. 11/675,037, "Response to May 23, 2008 Office Action", filed Jun. 9, 2008.
U.S. Appl. No. 11/675,037, "Response to Aug. 1, 2008 Office Action", filed Dec. 31, 2008.
U.S. Appl. No. 11/675,037, "Response to Final Rejection mailed Nov. 19, 2009, filed Apr. 19, 2010".
U.S. Appl. No. 12/129,641, "Response to Restriction Requirement mailed Mar. 19, 2010, filed Sep. 20, 2010".
U.S. Appl. No. 12/129,641, "Restriction Requirement mailed Mar. 19, 2010".
2,423,806, "Notice of Allowance mailed May 22, 2009".
2,423,806, "Office Action mailed May 9, 2008".
2,423,806, "Office Action mailed May 14, 2007".
2,423,806, "Response to Office Action", filed Oct. 26, 2006.
2,423,806, "Response to Office Action", filed Nov. 14, 2007.
2,423,806, "Response to Office Action", filed on Nov. 10, 2008.
20122672U1, "Office Action mailed Dec. 27, 2006".
20122672U1, "Response to Dec. 27, 2006 Office Action", filed Feb. 7, 2007.
U.S. Appl. No. 60/236,637, "Provisional Appln. filed Sep. 29, 2000".
U.S. Appl. No. 60/237,932, "Provisional Appln. filed Oct. 2, 2000".
U.S. Appl. No. 60/276,870, "Provisional Appln. filed Mar. 16, 2001".
U.S. Appl. No. 95/001,329, "Request for Inter Partes Reexam-Denied", Sep. 13, 2010.
Alvarez-Maubecin, Veronica et al., "Functional Coupling between Neurons and Glia", *The Journal of Neuroscience* vol. 20, No. 11 Jun. 1, 2000, 4091-4098.
Amlaiky, Nourdine et al., "A Novel RadioRodinated High Affinity Ligand for the D2 Dopamine Receptor.", *Febs Letters* vol. 176, No. 2 1984, 436-440.
Atamna, Hani et al., "A method for detecting a basic sites in living cells: Age-dependent changes in base excision repair.", *Proceedings of the National Academy of Sciences (PNAS)* vol. 97, No. 2 Jan. 18, 2000, 686-691.
Bannwarth, Willi et al., "Formation of Carboxamides with N,N,N',N'-Tetramethyl (Succinimido) Uronium Tetrafluoroborate in Aqueous Organic Solvent Systems", *Tetrahedron Letters* vol. 32, No. 9 1991, 1157-1160.
Barlin, Gordon B. et al., "Purine Analogues as Amplifiers of Phleomycin. IX* Some 2- and 6-Substituted Thiazolo [4,5,-b] Pyrazines, 2-Substituted Thiazolo[4,5,-c]- and Thiazolo[5,4,-b]-Pyridines and Related Compounds", *Aust. J. Chem.* vol. 37 1984, 1729-1737.

Barlin, Gordon B. et al., "Purine Analogues as Amplifiers of Phleomyein. Some Thiazolo[4,5-g] pyrazines and Related Compounds", *Aust. J. Chem.* vol. 36 1983, 983-985.
Bharaj, Bhupinder S. et al., "Rapid Sequencing of the p53 Gene with a New Automated DNA Sequencer", *Clinical Chemistry* vol. 44, No. 7 1998, 1397-1403.
Brinkley, Michael, "A Brief Survey of Methods for Preparing Protein Conjugates with Dyes, Haptens, and Cross-Linking Reagents", *Bioconjugate Chem.*, vol. 3 1992, 2-13.
Brooker, L G. et al., "Color and consitution. V. The absorption of unsymmetrical cyanines. Resonance as a basis for a classification of dyes", *Journal of the American Chemical Society* vol. 64, Communication No. 833 From the Kodak Research Laboratories Feb. 1942, 199-210.
Burns, Mark A. et al., "An Integrated Nanoliter DNA Analysis Device", *Science* vol. 282 1998, 484-487.
Chiavarelli, "4-Phenylpiperidines . V. Derivatives of 4, 4'-Spiro(1-Methylpiperidyl)-1, 2, 2, 4- tetrahydroisoquinoline", *abstract only of gazzetta chimica italiana* vol. 90, CA 55:70676 1960 , 189-195.
Chu-Moyer, Margaret Y. et al., "Preparation of the Four Regioisomeric 2-(Methylthio)oxazolopyridines: Useful Synthons for Elaboration to 2-(Amino substituted)oxazolopyridines", *Journal of Organic Chemistry* vol. 60, No. 17 1995, 5721-5725.
Couture, Axel et al., "Nouvelle Methode De Synthese De Thiazolopyridines", (French Version) *J. Heterocyclin Chem.* vol. 24 1987, 1765-1769.
Derisi, Joseph L. et al., "Exploring the Metabolic and Genetic Control of Gene Expression on a Genomic Scale", *Science,* vol. 278 Oct. 24, 1997, 680-686.
EP322710B9, "Notice to Opposition to a European Patent", Issue Date Jan. 2007.
EP01975541, "Amended claims filed after receipt of (European) search report", Apr. 22, 2003.
EP01975541, "Amendments received before examination", Apr. 22, 2003.
EP01975541, "Annex to the communication", May 2, 2005.
EP01975541, "Annex to the communication—opposition", Jun. 4, 2009.
EP01975541, "Claims—Opposition (Third Aux Request)", Oct. 9, 2009.
EP01975541, "Communication about intention to grant a European patent", Feb. 3, 2006.
EP01975541, "Communication from the Examining Division", May 2, 2005.
EP01975541, "Decision to grant a European patent", Jan. 2, 2007.
EP01975541, "Filing of a new opposition", Oct. 24, 2007.
EP01975541, "Grounds for the decision (Annex)—opposition", Dec. 18, 2009.
EP01975541, "Interlocutory decision in opposition proceedings", Dec. 18, 2009.
EP01975541, "International Search Report", Apr. 4, 2002.
EP01975541, "Minutes of the oral proceedings (Opposition Division)—conclusion of the proceedings", Dec. 18, 2009.
EP01975541, "Notice of further oppositions to opponent(s) mailed Apr. 23, 2008".
EP01975541, "Notice of opposition", Oct. 24, 2007.
EP01975541, "Reply to Apr. 23, 2008 Communication, filed Dec. 22, 2008".
EP01975541, "Reply to communication from the Examining Division", filed Sep. 12, 2005.
EP01975541, "Statement Setting Grounds of Appeal", *Dyomics GmbH* Apr. 23, 2010.
EP01975541, "Summons to attend oral proceedings", Jun. 4, 2009.
EP06025328, "EPO Search Report mailed Nov. 21, 2007".
EP06025328, "Examination Report mailed Jun. 13, 2008".
EP06025328, "Response to Jun. 13, 2008 Office Action", filed Dec. 16, 2008.
EP07001000, "European Search Report mailed Nov. 22, 2007".
EP07001000, "Examination Report mailed Jun. 11, 2008".
EP07001000, "Response to Jun. 11, 2008 Office Action", filed Feb. 13, 2009.

Estep, Timothy N. et al., "Optimization of Erythrocyte Membrane Glycoprotein Fluorescent Labeling with Dansylhydrazine after Polyacrylamide Gel Electrophoresis", *Analytical Biochemistry* vol. 157 1986, 100-105.

Ficken, G E. et al., "Diazaindenes and Their Quaternary Salts Part 1: The preparation of 2,3,3-Trimethyl-3H-1,7-diazaindene, and its Methiodides and Derived Cyanine Dyes", *Journal of Chemical Society* 1959, 3202-3212.

Ficken, et al., "Diazaines and Their Quarternary Salts Part 2", *CA 55:70677, abstract only of J of Chem Soc* 1961, 584-588.

Foye, William O. et al., "Antiradiation compounds XV: Condensations of carbon disulfide with amino, chloro, cyanomethyl, and sulfonamido heterocycles", *Journal of Pharmaceutical Science* vol. 64, No. 8 Aug. 1975, 1371-1374.

Fradelizi, Julie et al., "Quantitative Measurement of Proteins by Western Blotting with Cy5-Coupled Secondary Antibodies", *BioTechniques* vol. 26 Mar. 1999, 484-494.

Gruber, Hermann J. et al., "Anomalous Fluorescence Enhancement of Cy3 and Cy3.5 Versus Anomalous Fluorescence Loss of Cy5 and Cy7 Upon covalent Linking to IgG and Noncovalent Binding to Avidin", *Bioconjugate Chem.* vol. 11 2000, 696-704.

Haugland, Rosaria P., "Antibody Conjugates for Cell Biology", *Current Protocols in Cell Biology* 2000, 16.5.1-16.5.22.

Haugland, Rosaria P., "Ch 22: Coupling of monoclonal antibodies with fluorophores", *Methods in Molecular Biology* vol. 45: Monoclonal Antibody Protocols 1995, 205-221.

Haugland, Rosaria P. et al., "Coupling of monoclonal antibodies with biotin", *Methods in Molecular Biology* vol. 45 1995, 223-233.

Haugland, Rosaria P. et al., "Coupling of monoclonal antibodies with enzymes", *Methods in Molecular Biology* vol. 45 1995, 235-243.

Haugland, Richard P., "Handbook of Fluorescent Probes and Research Products", Ch 1-3.3 Molecular Probes, Inc/Invitrogen, 2002 2002, 11-118.

Haugland, Richard P., "Molecular Probes Handbook of Fluorescent Probes and Research Chemicals", Chapters 1-3 Molecular Probes, Inc, 1996, Sixth Edition 1996, Jul. 1980.

Haugland, Richard P., "Molecular Probes Handbook of Fluorescent Probes and Research Chemicals", *Ch 22: Indicators for Ca2+, Mg2+, Zn2+, and Other Metals* Sixth Edition and its subsequent 7th edition and 8th edition updates issued on CD ROM in Nov. 1999 and May 2001, Molecular Probes, Inc. 1996, 503-544.

Haugland, Richard P., "Molecular Probes Handbook of Fluorescent Probes and Research Products", 6th Edition 1996, 13-15.

Haugland, Richard P., "Molecular Probes Handbook of Fluorescent Probes and Research Products", Table of Contents 9th edition, CD ROM, Molecular Probes, Inc. 2002, 1-6.

Heravi, M M. et al., "Heterocyclic monoazo dyes derived from 2-(p-aminophenyl)oxazolo-[4,5-b]pyridine and 7-(p-aminophenyl)-4H-[1,3,4]thiadiazolo-[2,3-c][1,2,4]triazin-4-one", *Indian J. Chem.* 36B 1997, 1025-1029.

Hollars, Christopher W. et al., "Submicron Fluorescence, Topology, and Compliance Measurements of Phase-Separated Lipid Monolayers Using Tapping-Mode Near-Field Scanning Optical Microscopy", *The Journal of Physical Chemistry B* 101 Aug. 14, 1997, 6313-6317.

Kendall, Debra A. et al., "A Fluorescence Assay to Monitor Vesicle Fusion and Lysis", *The Journal of Biological Chemistry* vol. 257, No. 23 1982, 13892-13895.

Khanna, Ish K. et al., "Facile, Regioselective Synthesis of N-Alkylated 2,3-Diaminopyridines and Imidazo[4,5-b]pyridines", *J. Org. Chem.* vol. 60 1995, 960-965.

Licha, Kai et al., "Highly parallel nano-synthesis of cleavable peptide-dye conjugates on cellulose membranes", *Tetrahedron Letters* vol. 41 2000, 1711-1715.

Mac Beath, Gavin et al., "Printing Proteins as Microarrays for High-Throughput Function Determination", *Science,* vol. 289 2000, 1760-1763.

Manders, Erik M. et al., "Direct Imaging of DNA in Living Cells Reveals the Dynamics of Chromosome Formation", *Journal of Cell Biology* vol. 144, No. 5 Mar. 8, 1999, 813-821.

Martini, et al., "Relaxation dynamics in the first excited singlet state of a cyanine dye: HITC (Abstract)", *Chemical Physics Letters* 258 (1,2) 1996, 180-186.

McMahan, Scott et al., "Single-step synthesis and characterization of biotinylated nitrilotriacetic acid, a unique reagent for the detection of histidine-tagged proteins immobilized on nitrocellulose.", *Analytical Biochemistry* vol. 236 1996, 101-106.

Mishra, Amaresh et al., "Cyanines during the 1990s: A Review", *Chem. Rev.* vol. 100, No. 6 2000, 1973-2011.

Misra, Hari S. et al., "An Enzymatically Active Chimeric HIV-1 Reverse Transcriptase (RT) with the RNase-H Domain of Murine Leukemia Virus RT Exists as a Monomer", *The Journal of Biological Chemistry* vol. 273, No. 16 Apr. 17, 1998, 9785-9789.

Mujumdar, Ratnakar B. et al., "Cyanine Dye Labeling Reagents: Sulfoindocyanine Succinimidyl Esters", *Bioconjugate Chemistry* vol. 4, No. 2 Mar. 1, 1993, 105-111.

Mujumdar, Swati R., "Cyanine-Labeling Reagents: Sulfobenzindocyanine Succinimidyl Esters.", *Bioconjugate Chem* vol. 7 1996, 356-362.

Ozmen, Burcu et al., "Infrafed fluorescence sensing of submicromolar calcium: pushing the limits of photoinduced electron transfer", *Tetrahedron Letters* vol. 41 2000, 9185-9188.

Petric, A et al., "Azido-Tetrazolo Isomerizations of Some Thiazolopyridines (1)", *J. Heterocyclin Chem.* vol. 14 Oct. 1977, 1045-1047.

Pharmacia Biotech Inc., "Table of Contents", *Pharmacia Biotech Catalogue* 1994, 295.

Piatek, Amy S. et al., "Molecular beacon sequence analysis for detecting drug resistance in Mycobacterium Tuberculosis", *Nature Biotechnology* vol. 16 Apr. 1998, 359-363.

Raju, B. et al., "A fluorescent indicator for measuring cytosolic free magnesium", *Am. J. Phyl.* vol. 256 1989, C540-0548.

Roman, Beth L. et al., "Non-Radioisotopic AFLP Method Using PCR Primers Fluorescently Labeled with Cy5", *BioTechniques* vol. 26, No. 2 Feb. 1999, 236-238.

Saikachi, Haruo et al., "Studies on Compounds Related to Pyrazine. III. Synthesis of 2-Substituted Thiazolo[b]quinozaline.", *Chem. & Pharm. Bull.* vol. 9, No. 12 Dec. 1961, 941-944.

Schena, Mark et al., "Parallel human genome analysis: Microarray-based expression monitoring of 1000 genes", *Proceedings of the National Academy of Sciences (PNAS)* vol. 93, (Biochemistry) Oct. 1996, 10614-10619.

Smith, Keith et al., "The synthesis of 2-substituted thiazolo[5,4-c]pyridines via directed methalation", *Sulfur Letters* vol. 17, No. 4 1994, 197-216.

STN Registry, "File search history; generated Mar. 10, 2009".

Szoka, Francis J. et al., "Comparative Properties and Methods of Preparation of Lipid Vesicles (Liposomes)", *Annu. Rev. Biophys. Bioeng* vol. 9 1980, 467-508.

Szoka, Francis et al., "Procedure for Preparation of Liposomes with Large Internal Aqueous Space and High Capture by Reverse-Phase Evaporation.", *Proceedings of the National Academy of Sciences (PNAS)* vol. 75, No. 9 Sep. 1978, 4194-4198.

Turner, James A., "Regiospecific electrophilic substitution of aminopyridines: ortho lithiation of 2-, 3-, and 4-(pivaloylamino)pyridines", *Journal of Organic Chemistry* vol. 48 1983, 3401-3408.

Tyagi, Sanjay et al., "Multicolor molecular beacons for allele discrimination", *Nature Biotechnology,* vol. 16 1998, 49-53.

US 7,671,214, "Corrected Request for Inter Parties Reexamination, mailed Jul. 2, 2010".

US 7,671,214, "Request for Inter Parties Reexamination, mailed Mar. 26, 2010".

US 7,671,214, "USPTO's Response to Initial Request for Inter Parties Reexamination, mailed Jun. 7, 2010".

Voss, H. et al., "Automated Cycle Sequencing with Taquenase: Protocols for Internal Labeling, Dye Primer and Doublex Simultaneous Sequencing", *BioTechniques* vol. 23, No. 2 Aug. 1997, 312-318.

Waggoner, et al., "Cyanine Dye Labeling Reagents: Sulfoindocyanine Succinimidyl Esters", *Bioconjugate Chem* 1993, 105-111.

WO 2002/026891, "PCT ISR mailed Mar. 14, 2002".

U.S. Appl. No. 12/129,641, "Office Action Mailed Dec. 6, 2010".

\* cited by examiner

MODIFIED CARBOCYANINE DYES AND THEIR CONJUGATES

CROSS-REFERENCE TO RELATED APPLICATIONS

This application is a divisional of US Ser. No. 11/675,033, filed Feb. 14, 2007, which is a continuation of U.S. Ser. No. 11/150,596, filed Jun. 10, 2005, which is a divisional of U.S. Ser. No. 09/968,401 filed Sep. 29, 2001 (U.S. Pat. No. 6,977, 305) and U.S. Ser. No. 09/969,853, filed Oct. 1, 2001 (U.S. Pat. No. 6,974,873), which claims priority to U.S. Ser. No. 60/236,637, filed Sep. 29, 2000; and U.S. Ser. No. 60/276, 870, filed Mar. 16, 2001, which disclosures are herein incorporated by reference.

INTRODUCTION

1. Field of the Invention

The invention relates to colored and fluorescent chemicals, including reactive dyes and dye-conjugates; and to their uses.

2. Background of the Invention

Fluorescent compounds are covalently or noncovalently attached to other materials to impart color and fluorescence. Brightly fluorescent dyes permit detection or location of the attached materials with great sensitivity. Certain carbocyanine dyes have demonstrated utility as labeling reagents for a variety of biological applications, e.g. U.S. Pat. Nos. 4,981, 977 to Southwick, et al. (1991); 5,268,486 to Waggoner et al. (1993); 5,569,587 to Waggoner (1996); 5,569,766 to Waggoner et al. (1996); 5,486,616 to Waggoner et al. (1996); 5,627,027 to Waggoner (1997); 5,808,044 to Brush, et al. (1998); 5,877,310 to Reddington, et al. (1999); 6,002,003 to Shen, et al. (1999); 6,004,536 to Leung et al. (1999); 6,008, 373 to Waggoner, et al. (1999); 6,043,025 to Minden, et al. (2000); 6,127,134 to Minden, et al. (2000); 6,130,094 to Waggoner, et al. (2000); 6,133,445 to Waggoner, et al. (2000); also WO 97/40104, WO 99/51702, WO 01/21624, and EP 1 065 250 A1; and TETRAHEDRON LETTERS 41, 9185-88 (2000); all of the above incorporated by reference. Nevertheless, many carbocyanine dyes are known to share certain disadvantages, e.g. severe quenching of the fluorescence of carbocyanine dyes in biopolymer conjugates, e.g. quenching of Cy5 and Cy7 dye variants on conjugates, as discussed by Gruber et al., BIOCONJUGATE CHEM. 11, 696 (2000), and in EP 1 065 250 A1, 0004. In addition, certain desired sulfoalkyl derivatives of the reactive carbocyanine dyes are difficult to prepare, as indicated for Cy3 and Cy5 variants by Waggoner and colleagues in BIOCONJUGATE CHEM. 4, 105, 109 col.2 (1993). Cyanine dyes also have a very strong tendency to self-associate (i.e. stack), which can significantly reduce the fluorescence quantum yields, as described in the extensive review by Mishra, et al., CHEM. REV. 100, 1973 (2000).

Modification of an indolium ring of the carbocyanine dye to permit a reactive group or conjugated substance at the number 3 position unexpectedly mitigates these problems and results in dye-conjugates that are uniformly and substantially more fluorescent on proteins, nucleic acids and other biopolymers, than conjugates labeled with structurally similar carbocyanine dyes bound through the nitrogen atom at the number 1 position. In addition to having more intense fluorescence emission than structurally similar dyes at virtually identical wavelengths, and decreased artifacts in their absorption spectra upon conjugation to biopolymers, certain embodiments of the invention also have greater photostability and higher absorbance (extinction coefficients) at the wavelength(s) of peak absorbance than such structurally similar dyes. These improvements result in significantly greater sensitivity in assays that use these dyes and their conjugates, while utilizing available filters and instrumentation already commercially available for use with similar dyes.

Furthermore, the dyes of the invention typically exhibit absorbance maxima between about 530 nm and about 800 nm, so dyes can be selected to match the principal emission lines of the mercury arc lamp (546 nm), frequency-doubled Nd-Yag laser (532 nm), Kr-ion laser (568 nm and 647 nm), HeNe laser (543 nm, 594 nm, and 633 nm) or long-wavelength laser diodes (especially 635 nm and longer). The azacarbocyanine dyes of the invention exhibit a bathochromic spectral shift (a shift to longer wavelength) of approximately 20 to 50 nm relative to otherwise structurally similar carbocyanine dyes known in the art. Some dyes of the invention exhibit very long wavelength excitation (at least 640 nm, but some greater than about 730 nm) and emission bands (at least 665 nm, and some greater than about 750 nm), so they are particularly useful for samples that are transparent to infrared wavelengths.

SUMMARY OF THE INVENTION AND DESCRIPTION OF PREFERRED EMBODIMENTS

Figure 1:
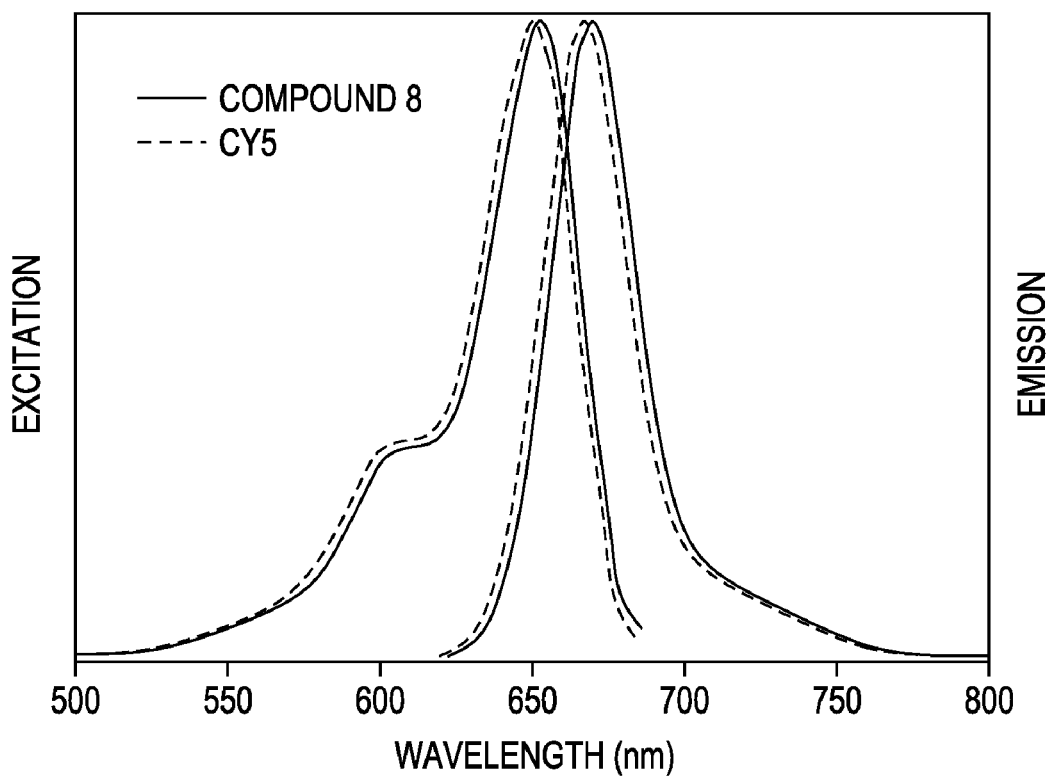
FIG. 1. Fluorescence excitation and emission spectra of 1.0 µM solutions (pH=7.5) of Cy5 and Compound 8 are shown. Both the excitation and emission characteristics of the Compound 8 are very similar to those of Cy5, when present as the free-acid.

The present invention describes modified carbocyanine dyes and their conjugates Preferred compounds have at least one substituted indolium ring system wherein the substituent on the 3-carbon of the indolium ring contains a chemically reactive group or a conjugated substance. Other preferred compounds incorporate an azabenzazolium ring moiety and at least one sulfonate moiety. The dyes and dye conjugates are used to locate or detect the interaction or presence of analytes or ligands in a sample. Kits incorporating such dyes or dye conjugates facilitate their use in such methods.

Dyes

The carbocyanine dyes of the invention typically comprise two heterocyclic ring systems bound together by a polymethine linker, according to the formula:

A-BRIDGE-B where A is a first heterocyclic ring system that is a substituted benzazolium ring that optionally incorporates one or more nitrogen atoms (azabenzazolium rings), B is a second heterocyclic ring system that is a substituted benzazolium or azabenzazolium ring, and BRIDGE is a polymethine linker that is optionally substituted. The first and second ring systems and polymethine linker are optionally further substituted by a variety of substituents or are fused to additional rings that are optionally further substituted. In one aspect of the invention, the carbocyanine dye contains a chemically reactive group or a conjugated substance that is attached at carbon 3 of an indolium ring system. In a preferred embodiment, the carbocyanine dye is further substituted one or more times by sulfo or sulfoalkyl.

By "sulfo" is meant sulfonic acid, or salt of sulfonic acid (sulfonate). Similarly, by "carboxy" is meant carboxylic acid or salt of carboxylic acid. "Phosphate", as used herein, is an ester of phosphoric acid, and includes salts of phosphate. "Phosphonate", as used herein, means phosphonic acid and includes salts of phosphonate. As used herein, unless otherwise specified, the alkyl portions of substituents such as alkyl, alkoxy, arylalkyl, alkylamino, dialkylamino, trialkylammonium, or perfluoroalkyl are optionally saturated, unsaturated, linear or branched, and all alkyl, alkoxy, alkylamino, and dialkylamino substituents are themselves optionally further substituted by carboxy, sulfo, amino, or hydroxy.

The A moiety has the formula:

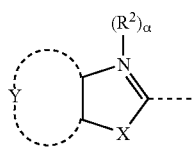

Formula I wherein Y represents the atoms necessary to form one to two fused aromatic rings having 6 atoms in each ring, which atoms are selected from —CH, —C, —CR$^1$, and —N(R$^2$)$_\beta$, where each $\beta$ is 0 or 1 (such that each ring nitrogen is either quaternized or not), and each R$^1$ is independently -L-R$_x$; or -L-S$_c$; or amino, sulfo, trifluoromethyl, or halogen; or C$_1$-C$_6$ alkyl, C$_1$-C$_6$ alkoxy, C$_1$-C$_6$ alkylamino, C$_2$-C$_{12}$ dialkylamino, optionally further substituted. Incorporation of one or more non-hydrogen substituents on the fused rings can be used to fine tune the absorption and emission spectrum of the resulting dye. In one embodiment, there is at least one non-hydrogen substituent, preferably sulfo, an alkoxy or halogen; preferably the halogen is bromine. In one embodiment, R$^1$ is independently -L-R$_x$; or -L-S$_c$; or amino, sulfo, trifluoromethyl, or halogen; or C$_1$-C$_6$ alkyl, which is optionally further substituted by carboxy, sulfo, amino, or hydroxy.

In one embodiment, X is one of O, S, Se or NR$^5$, where R$^5$ is H or an alkyl group having 1-22 carbons, that is optionally substituted one or more times by hydroxy, carboxy, sulfo, amino, alkylamino having 1-6 carbons or dialkylamino having 2-12 carbons. Alternatively, X is O, S, or —CR$^3$R$^4$, where R$^3$ and R$^4$, which may be the same or different, are alkyl or arylalkyl, and optionally further substituted. Preferably, R$^3$ is -L-R$_x$ or -L-S$_c$ (as defined below).

The substituents R$^2$, R$^4$, and R$^{12}$ are independently -L-R$_x$; or -L-S$_c$; or a C$_1$-C$_{22}$ alkyl or C$_7$-C$_{22}$ arylalkyl, each alkyl portion of which optionally incorporates up to six hetero atoms, selected from N, O and S, and each alkyl portion of which is optionally substituted one or more times by fluorine, chlorine, bromine, iodine, hydroxy, carboxy, sulfo, phosphate, amino, sulfate, phosphonate, cyano, nitro, azido, C$_1$-C$_6$ alkoxy, C$_1$-C$_6$ alkylamino, or C$_2$-C$_{12}$ dialkylamino, or C$_3$-C$_{18}$ trialkylammonium; or R$^3$ and R$^4$ taken in combination complete a five- or six-membered saturated or unsaturated ring that is substituted by -L-R$_x$; or -L-S$_c$. Preferably, R$^4$ is alkyl having 1-6 carbons, optionally substituted one or more times by fluorine, chlorine, bromine, iodine, hydroxy, carboxy, sulfo, or amino; more preferably R$^4$ is methyl or ethyl. In one aspect of the invention, R$^4$ is methyl. Alternatively, R$^4$ in combination with R$^{21}$ forms a 6-membered ring, as described below; or R$^4$ taken in combination with R$^3$ forms a saturated or unsaturated ring substituent, that is substituted by -L-R$_x$ or -L-S$_c$.

The substitutents R$^2$ and R$^{12}$ are typically independently -L-R$_x$; or -L-S$_c$; or a C$_1$-C$_6$ alkyl, which is optionally substituted one or more times by F, Cl, Br, I, hydroxy, carboxy, sulfo, or amino. Preferably R$^2$ and R$^{12}$ are independently alkyl with 1-6 carbon atoms that are unsubstituted or are substituted once by hydroxy, sulfo, carboxy or amino. Where either R$^2$ or R$^{12}$ is substituted by hydroxy, sulfo, carboxy or amino, the substituent is preferably separated from the indolium or other benzazolium nitrogen atom by 2-6 carbon atoms. Where R$^2$ and R$^{12}$ are unsubstituted alkyl groups, they are preferably methyl or ethyl, most preferably methyl. Typically R$^2$ and R$^{12}$ are the same and are methyl, ethyl, sulfopropyl or sulfobutyl.

The B moiety has the formula:

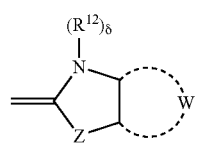

Formula VII where W represents the atoms necessary to form one to two fused aromatic rings having 6 atoms in each ring, which atoms are selected from —CH, —C, —CR$^{1'}$, and —N(R$^{12}$)$_{\beta'}$, where each β' is 0 or 1 (such that each ring nitrogen is either quaternized or not), and each R$^{1'}$ is independently -L-R$_x$; or -L-S$_c$; or amino, sulfo, trifluoromethyl, or halogen; or C$_1$-C$_6$ alkyl, C$_1$-C$_6$ alkoxy, C$_1$-C$_6$ alkylamino, C$_2$-C$_{12}$ dialkylamino, each of which is optionally further substituted by carboxy, sulfo, amino, or hydroxy. Where the six membered rings form an azabenzazole ring system, they typically incorporate 1-3 nitrogen atoms, more preferably 1-2 nitrogen atoms, typically incorporated in the first 6-membered aromatic ring fused to the azole ring. In one aspect of the invention, the ring system W contains only carbon atoms and is a benzazole ring system. In one embodiment, each R$^1$ is independently -L-R$_x$; or -L-S$_c$; or amino, sulfo, trifluoromethyl, or halogen; or C$_1$-C$_6$ alkyl, which is optionally further substituted by carboxy, sulfo, amino, or hydroxy.

Where A or B is an azabenzazolium, the fused aromatic rings typically incorporate 1-3 nitrogen atoms, more preferably 1-2 nitrogen atoms, typically incorporated in the first 6-membered aromatic ring fused to the azole ring. Preferred embodiments of the azabenzazole moiety include without limitation the following structures, (and the equivalent structures where the nitrogen is quaternized by R$^{12}$):

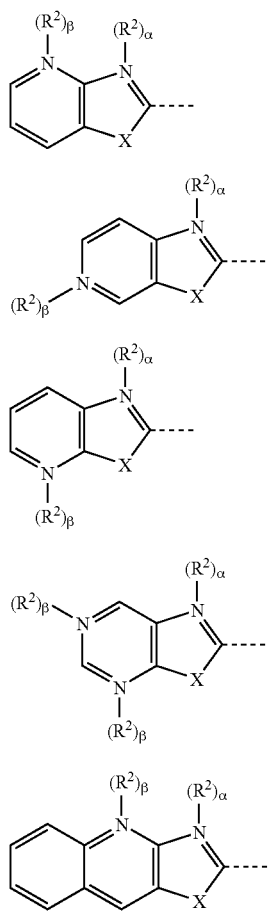

When Y or W includes a nitrogen atom, at least one of the azabenzazole nitrogen atoms is quaternized, resulting in a formal positive charge. In one embodiment, the azole nitrogen atom is quaternized, and the benzo nitrogen atom is unsubstituted. Preferably, the azole nitrogen atom is unsubstituted and at least one benzo nitrogen atom is quaternized. Typically, no more than one azole nitrogen on a given azabenzazole is quaternized, i.e. α is 0 or 1, β is 0 or 1, and α+all β=1; and δ is 0 or 1, β' is 0 or 1, and δ+all β'=1. The presence of additional fused 6-membered rings (as in Formula VI, above) shift the wavelength even further.

Choice of the X and Z moieties may also affect the dye's absorption and fluorescence emission properties. X and Z are optionally the same or different, and spectral properties of the resulting dye may be tuned by careful selection of X and Z. In one embodiment, Z is one of O, S, Se or NR$^{15}$, where R$^{15}$ is H or an alkyl group having 1-22 carbons, that is optionally substituted one or more times by hydroxy, carboxy, sulfo, amino, alkylamino having 1-6 carbons or dialkylamino having 2-12 carbons. Alternatively, Z is O, S, or —CR$^{13}$R$^{14}$, where R$^{13}$ and R$^{14}$, which may be the same or different, are alkyl or arylalkyl, and optionally further substituted. Typically X and Z are —CR$^3$R$^4$ and —CR$^{13}$R$^{14}$, respectively.

Where Z is —CR$^{13}$R$^{14}$, the substituents R$^{13}$ and R$^{14}$, which may be same or different, are independently -L-R$_x$; or -L-S$_c$; or a C$_1$-C$_{22}$ alkyl or C$_7$-C$_{22}$ arylalkyl, each alkyl portion of which optionally incorporates up to six hetero atoms, selected from N, O and S, and each alkyl portion of which is optionally substituted one or more times by fluorine, chlorine, bromine, iodine, hydroxy, carboxy, sulfo, phosphate, amino, sulfate, phosphonate, cyano, nitro, azido, C$_1$-C$_6$ alkoxy, C$_1$-C$_6$ alkylamino, or C$_2$-C$_{12}$ dialkylamino, or C$_3$-C$_{18}$ trialkylammonium. Alternatively, R$^{13}$ and R$^{14}$ in combination complete a five or six membered saturated or unsaturated ring that is optionally substituted by -L-R$_x$; or -L-S$_c$; or R$^{13}$ or R$^{14}$ combines with a methine substituent to form a ring, as described below. In one embodiment, one of R$^{13}$ and R$^{14}$ is a C$_1$-C$_6$ alkyl and the other of R$^{13}$ and R$^{14}$ is -L-R$_x$; or -L-S$_c$; or a C$_1$-C$_{22}$ alkyl, which is optionally substituted one or more times by F, Cl, Br, I, hydroxy, carboxy, sulfo, phosphate, amino, sulfate, phosphonate, cyano, nitro, azido, C$_1$-C$_6$ alkoxy, C$_1$-C$_6$ alkylamino, or C$_2$-C$_{12}$ dialkylamino. Preferably R$^{13}$ and R$^{14}$ are independently alkyl with 1-6 carbon atoms that are unsubstituted or are substituted once by hydroxy, sulfo, carboxy or amino. Where either R$^{13}$ or R$^{14}$ is substituted by hydroxy, sulfo, carboxy or amino, the substituent is preferably separated from the indolium or other benzazolium nitrogen atom by 2-6 carbon atoms. In one aspect of the invention, R$^{13}$ and R$^{14}$ are alkyls having 1-6 carbons, preferably methyls. In another aspect of the invention, one of R$^{13}$ and R$^{14}$ is methyl, and the other is alkyl having 1-6 carbons that is substituted by carboxy or by sulfo or by hydroxy, or by -L-R$_x$ or -L-S$_c$.

The BRIDGE moiety has the formula:

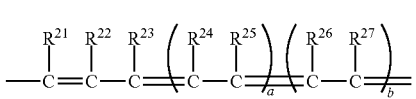

Formula VIII wherein a and b are independently 0 or 1. In a preferred aspect of the azacarbocyanine dyes, either a or b is 1, not both. The length of the polymethine bridge between the heterocyclic ring systems, also affects the dye's absorption and emission properties. Where Z is CR$^{13}$R$^{14}$, and a and b=0, and the indolium heterocycle is not fused to additional rings, the resulting "indocarbocyanine" dye typically exhibits an absorption maximum near 550 nm. Where a=1 and b=0, the "indodicarbocyanines" dyes typically absorb maximally near 650 nm. The "indotricarbocyanine" dyes, where a and b are both 1, typically absorbs maximally near 750 nm.

Each of $R^{21}$, $R^{22}$, $R^{23}$, $R^{24}$, $R^{25}$, $R^{26}$, and $R^{27}$, when present, is independently H, F, Cl, alkyl having 1-6 carbons, alkoxy having 1-6 carbons, aryloxy, a N-heteroaromatic moiety, or an iminium ion. Alternatively, two substituents $R^{21}$, $R^{22}$, $R^{23}$, $R^{24}$, $R^{25}$, $R^{26}$, and $R^{27}$, when taken in combination, form a 4-, 5-, or 6-membered saturated or unsaturated hydrocarbon ring that is unsubstituted or is optionally substituted one or more times by a saturated or unsaturated alkyl having 1-6 carbons, halogen, or a carbonyl oxygen, or thiocarbonyl. In yet another embodiment, $R^{21}$ combines with $R^4$ to form a 6-membered ring that is optionally substituted by alkyl having 1-6 carbons. Alternatively, $R^{23}$ (where a and b are both 0), $R^{25}$ (where a=1 and b=0), or $R^{26}$ (where a and b are both 1) taken in combination with one of $R^{13}$ and $R^{14}$ forms a 6-membered ring that is optionally substituted by alkyl having 1-6 carbons.

Examples of appropriate BRIDGE moieties have been previously described in the literature, including BRIDGE moieties that incorporate nonhydrogen substituents, ring structures, and rigidizing elements (U.S. Pat. Nos. 5,831,098 to Ollmann, Jr (1998); 6,086,737 to Patonay et al. (2000); 6,048,982 to Waggoner (2000); and 5,453,505 to Lee et al. (1995); 5,639,874 to Middendorf et al. (1997); 3,864,644 to Lincoln et al (1975); 4,011,086 to Simson (1977); all incorporated by reference).

Typically, each of $R^{21}$, $R^{22}$, $R^{23}$, $R^{24}$, $R^{25}$, $R^{26}$ and $R^{27}$, when present, is H. Where one of $R^{21}$, $R^{22}$, $R^{23}$, $R^{24}$, $R^{25}$, $R^{26}$, and $R^{27}$ is nonhydrogen, it is typically the substituent on the center carbon of BRIDGE, i.e., $R^{22}$ where a=0 and b=0, $R^{23}$ were a=1 and b=0, and $R^{24}$ where a=1 and b=1. Similarly, where BRIDGE incorporates a 4-, 5-, or 6-membered ring, it typically occurs at the center of the BRIDGE moiety, for instance as shown below for a pentamethine dye:

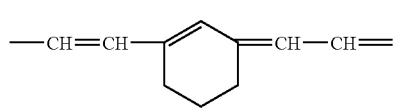

Formula IX

A preferred version of the invention is a compound of the formula:

Formula X

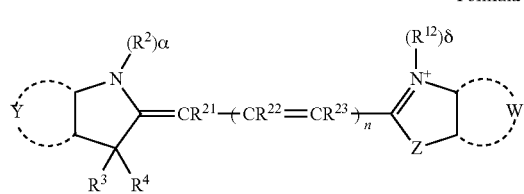

and its salts, where $R^2$, $R^3$, $R^4$, $R^{12}$, α, δ W, Y, and Z are as defined previously. For simplicity, $R^{21-23}$ are independently as defined previously for $R^{21-27}$, and n=1, 2, or 3. Where n is >3, the dyes have spectra even further shifted into the infrared region. More preferably, the dye has the formula:

Formula XI

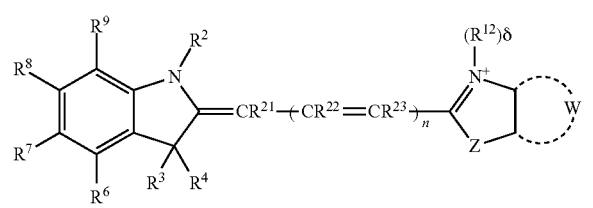

The substituents $R^6$-$R^9$ are independently selected from H, alkyl having from 1-6 carbons, alkoxy having 1-6 carbons, amino, alkylamino having 1-6 carbons, or dialkylamino having 2-12 carbons, sulfo, carboxy, perfluoroalkyl having 1-6 carbons, or halogen.

In one aspect of the invention, both A and B are benzazolium rings, according to the formula:

Formula XXI

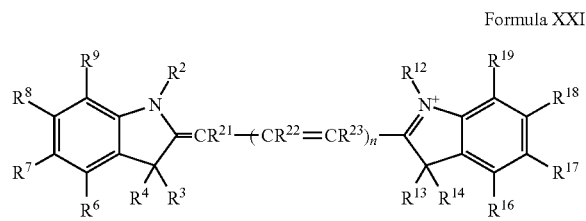

where the substituents $R^{16}$-$R^{19}$ are independently selected from H, alkyl having from 1-6 carbons, alkoxy having 1-6 carbons, amino, alkylamino having 1-6 carbons, or dialkylamino having 2-12 carbons, sulfo, carboxy, perfluoroalkyl having 1-6 carbons, or halogen.

Incorporation of one or more non-hydrogen substituents on either or both benzazolium rings are useful to fine-tune the absorption and emission spectrum. There is typically at least one non-hydrogen substituent on each of the benzazolium rings, preferably sulfo, an alkoxy or a halogen substituent. Typically, the substituents on the benzo rings are H or sulfo. In one embodiment, one of $R^6$, $R^7$, $R^8$, and $R^9$ or of $R^{16}$, $R^{17}$, $R^{18}$, and $R^{19}$ is a dialkylamino that is a saturated 5- or 6-membered nitrogen heterocycle, such as piperidine. Additionally, any two adjacent substituents of $R^6$-$R^9$ and $R^{16}$-$R^{19}$ are optionally taken in combination to form one or more fused aromatic rings. These additional rings are optionally further substituted as described above for $R^6$-$R^9$ and $R^{16}$-$R^{19}$, and in particular by sulfonic acids.

Selected examples of carbocyanine dyes of the invention possessing additional fused aromatic rings are given below (for simplicity, all but a few of the possible substituents are shown as hydrogen, with the shortest polymethine bridge):

Formula XII

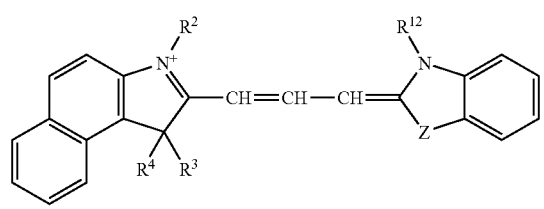

Formula XIII

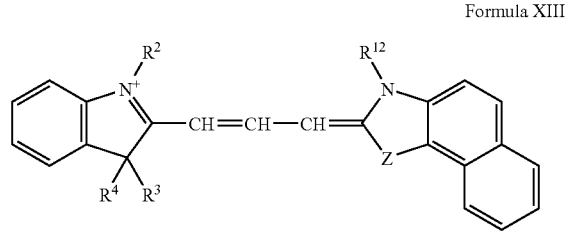

Formula XIV

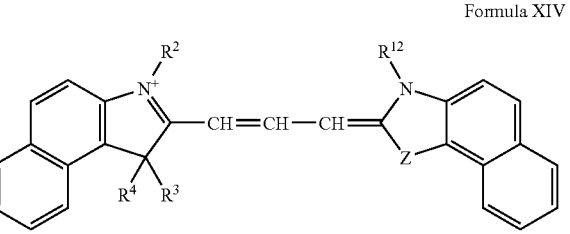

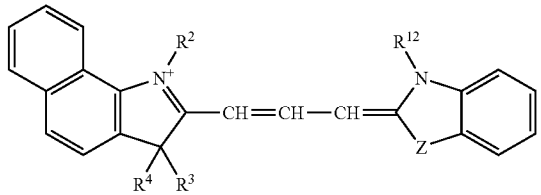

Formula XV

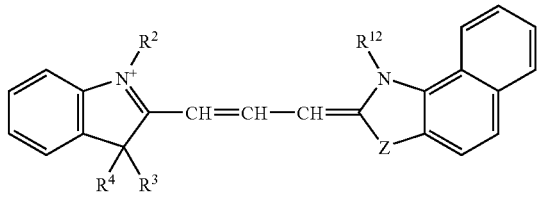

Formula XVI

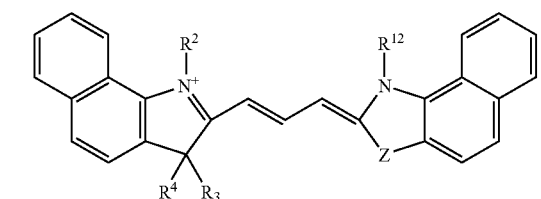

Formula XVII

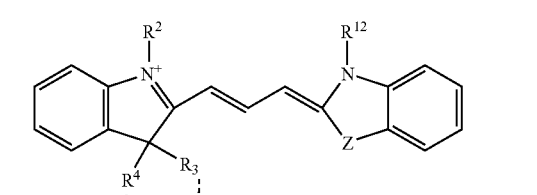

Formula XVIII

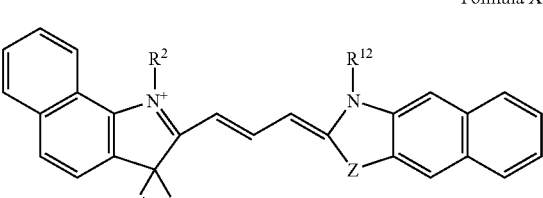

Formula XIX

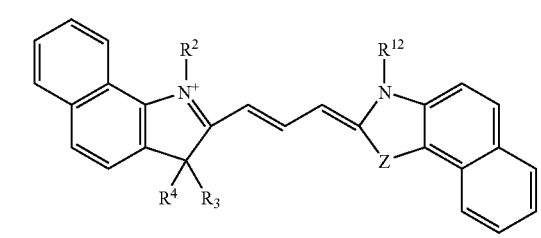

Formula XX

These basic structures, and their longer-wavelength analogs, are optionally further substituted as described in this section. Additional variants not specifically depicted above are also within the scope of the invention, e.g the "left-hand" indolium of Formula XVIII linked to a benzazolium of Formula XVII, XIX, or XX; azabenzazolium versions, such as:

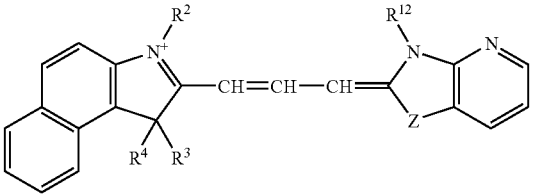

Formula XXIII and variations thereof, according to the formulas as above.

In another aspect of the invention, A is a benzazolium and B is an azabenzazolium, according to the formula:

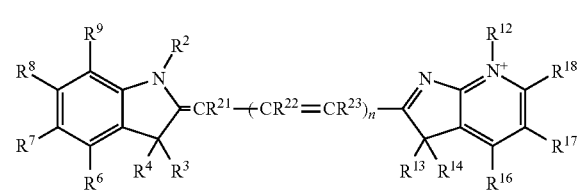

Formula XXII where the substituents $R^6$-$R^9$ and $R^{16}$-$R^{19}$ are as described previously. Preferred substitutents for $R^{16}$ through $R^{18}$ are independently H, -L-$R_x$; or -L-$S_c$; or amino, trifluoromethyl, or halogen; or $C_1$-$C_6$ alkyl, $C_1$-$C_6$ alkoxy, $C_1$-$C_6$ alkylamino, $C_2$-$C_{12}$ dialkylamino, each of which is optionally further substituted by carboxy, sulfo, amino, or hydroxy. Preferably, the only non-hydrogen substituent on the B side, when present, is a bromine at preferably bromine at $R^{17}$. Preferably n=2.

Figure 4:
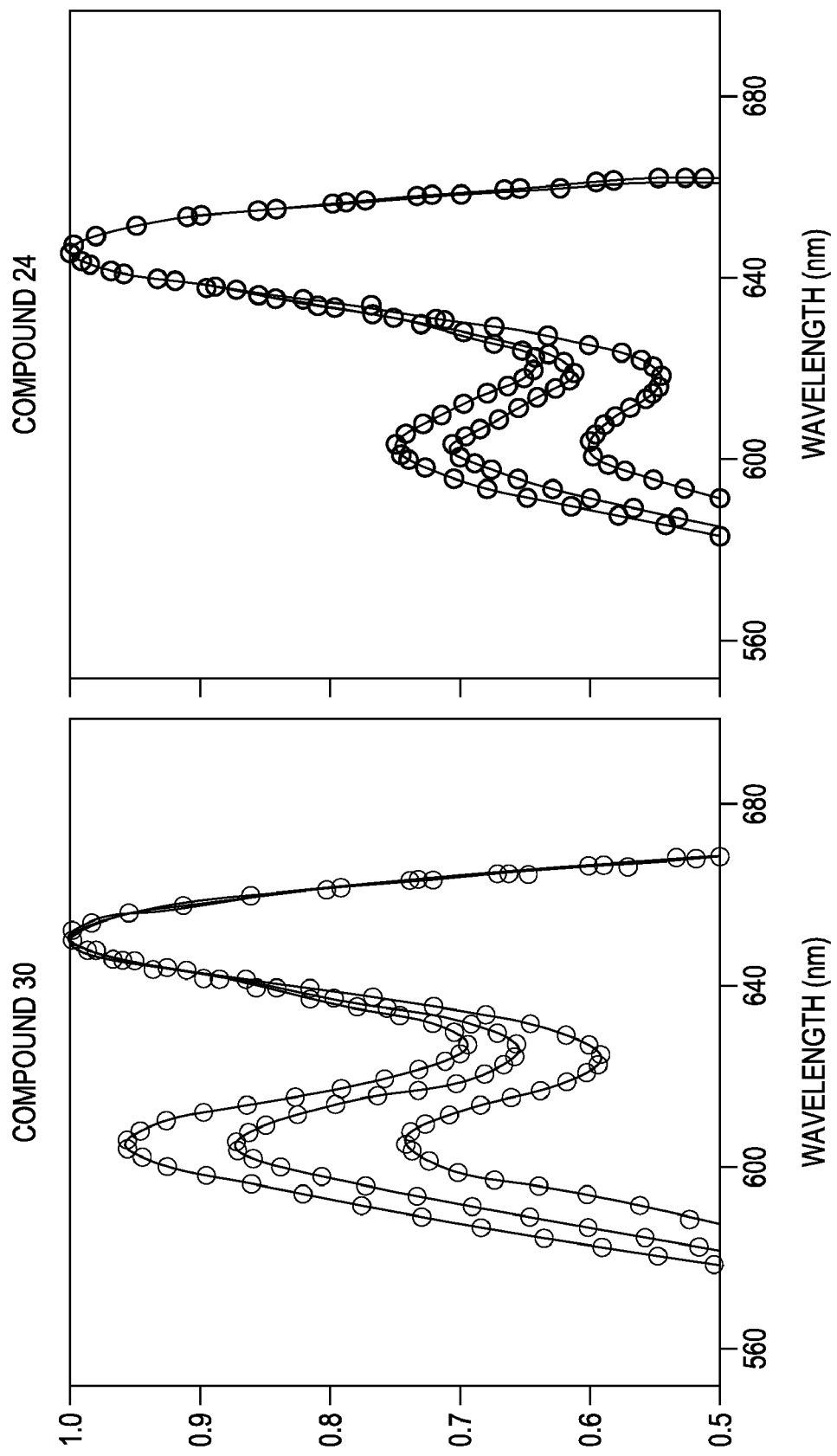
FIG. 4. Direct comparison of absorbance properties of Compound 30 (Cy5-type linkage, open circles) with Compound 24 (of the invention, closed circles) when conjugated to GAR at DOS's of approximately 2.8, 4.3, and 5.5 (600 nm absorbance bands increasing as a function of increasing DOS, 650 nm absorbance bands normalized to 1.0) (see Example 70).

In one aspect of the invention, the carbocyanine dyes of the invention are sulfonated one or more times. If the dye of the invention is substituted by sulfo, it is typically sulfonated at $R^7$ or $R^{17}$ or both, or sulfoalkylated at $R^2$ or $R^{12}$ or both, or is both sulfonated and sulfoalkylated. Typically, where the aromatic ring of Y or W contains one or more nitrogen atoms, the ring with the nitrogen is not sulfonated. Generally, commercially available reactive carbocyanine dyes are sulfonated up to two times (at positions corresponding to $R^7$ and $R^{17}$, and as sulfoalkyl at one of $R^2$ and $R^{12}$), leaving one of $R^2$ and $R^{12}$ for the location of the reactive group. In contrast, by attaching the reactive group (or conjugated substance) at $R^3$, certain carbocyanine dyes of the invention may be sulfonated at least four times (at $R^7$, at $R^{17}$, and as sulfoalkyl at $R^2$ and $R^{12}$). This extra sulfonation, as well as the change in attachment site, results in reactive dyes and dye conjugates that are brighter, more soluble in aqueous solutions, and more resistant to the fluorescence quenching that results from dye-dye stacking interactions. However, sulfonation by four or more sulfonic acids is not required for the dyes of the invention to have spectral properties that are superior to those of structurally similar dyes that are not linked through the 3 position of the indolium ring (FIG. 4).

In addition, the dyes of the invention are substituted by one or more chemically reactive groups (-L-$R_x$) or conjugated substances (-L-$S_C$), as described below. Typically, the -L-$R_x$ or -L-$S_C$ moieties are bound to the dye at an $R^2$, $R^3$, $R^4$, $R^{13}$ or $R^{14}$. Alternatively, -L-$R_x$ or -L-$S_C$ is bound to the dye at an aromatic carbon atom of the azabenzazolium ring, or the benzazolium ring. In a preferred embodiment, one or more of $R^2$ and $R^{12}$ is -L-$R_x$ or -L-$S_C$. In yet another preferred embodiment of the invention, one or more of $R^3$, $R^4$, $R^{13}$, and $R^{14}$ is -L-$R_x$ or -L-$S_C$. Alternatively, one or more of $R^{21}$, $R^{22}$, $R^{23}$, $R^{24}$, $R^{25}$, $R^{26}$, and $R^{27}$ is -L-$R_x$ or -L-$S_C$. In a preferred embodiment, the dye of the invention is substituted by only one -L-$R_x$ or -L-$S_C$.

Many embodiments of the compounds of the invention possess an overall electronic charge. It is to be understood that when such electronic charges are shown to be present, they are balanced by the presence of an appropriate counterion, which may or may not be explicitly identified. A biologically compatible counterion, which is preferred for some applications, is not toxic in biological applications, and does not have a substantially deleterious effect on biomolecules. Where the compound of the invention is positively charged, the counterion is typically selected from, but not limited to, chloride, bromide, iodide, sulfate, alkanesulfonate, arylsulfonate, phosphate, perchlorate, tetrafluoroborate, tetraarylboride, nitrate and anions of aromatic or aliphatic carboxylic acids. Where the compound of the invention is negatively charged, the counterion is typically selected from, but not limited to, alkali metal ions, alkaline earth metal ions, transition metal ions, ammonium or substituted ammonium or pyridinium ions. Preferably, any necessary counterion is biologically compatible, is not toxic as used, and does not have a substantially deleterious effect on biomolecules. Counterions are readily changed by methods well known in the art, such as ion-exchange chromatography, or selective precipitation.

It is to be understood that the dyes of the invention have been drawn in one or another particular electronic resonance structure. Every aspect of the instant invention applies equally to dyes that are formally drawn with other permitted resonance structures, as the electronic charge on the subject dyes are delocalized throughout the dye itself.

TABLE 1

Spectral properties of selected dyes of the invention

| Cpd No. | Excitation (nm, MeOH) | Emission (nm, MeOH) | Quantum Yield† (MeOH) |
|---|---|---|---|
| 63 | 665 | 694 | 0.55 |
| 64 | 653 | 695 | 0.15 |
| 65 | 664 | 693 | 0.4 |
| 66 | 686 | 706 | 0.35 |
| 68 | 664 | 696 | 0.4 |
| 70 | 570 | 592 | 0.44 |
| 72 | 663 | 694 | 0.42 |
| 73 | 664 | 697 | 0.48 |
| 76 | 685 | 705 | 0.46 |
| 81 | 750 | 800 | 0.12 |

†Relative to nile blue in ethanol and CY5 dye in methanol

Conjugates of Reactive Dyes

In one embodiment of the invention, the dye contains at least one group -L-$R_x$, where $R_x$ is the reactive group that is attached to the dye by a covalent linkage L. In certain embodiments, the covalent linkage attaching the dye to $R_x$ contains multiple intervening atoms that serve as a spacer. The dyes with a reactive group ($R_x$) label a wide variety of organic or inorganic substances that contain or are modified to contain functional groups with suitable reactivity, resulting in chemical attachment of the conjugated substance ($S_c$), represented by -L-$S_C$. As used herein, "reactive group" means moiety on the compound that is capable of chemically reacting with a functional group on a different compound to form a covalent linkage. Typically the reactive group is an electrophile or nucleophile that can form a covalent linkage through exposure to the corresponding functional group that is a nucleophile or electrophile, respectively. Alternatively, the reactive group is a photoactivatable group, and becomes chemically reactive only after illumination with light of an appropriate wavelength. Typically, the conjugation reaction between the reactive dye and the substance to be conjugated results in one or more atoms of the reactive group $R_x$ to be incorporated into a new linkage L attaching the dye to the conjugated substance $S_c$. Selected examples of reactive groups and linkages are shown in Table 2, where the reaction of an electrophilic group and a nucleophilic group yields a covalent linkage.

TABLE 2

Examples of some routes to useful covalent linkages

| Electrophilic Group | Nucleophilic Group | Resulting Covalent Linkage |
|---|---|---|
| activated esters* | amines/anilines | carboxamides |
| acrylamides | thiols | thioethers |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carbodiimides | carboxylic acids | N-acylureas or anhydrides |
| diazoalkanes | carboxylic acids | esters |
| epoxides | thiols | thioethers |
| haloacetamides | thiols | thioethers |
| haloplatinate | amino | platinum complex |
| haloplatinate | heterocycle | platinum complex |
| haloplatinate | thiol | platinum complex |
| halotriazines | amines/anilines | aminotriazines |
| halotriazines | alcohols/phenols | triazinyl ethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

*Activated esters, as understood in the art, generally have the formula —COΩ, where Ω is a good leaving group (e.g. succinimidyloxy (—$OC_4H_4O_2$) sulfosuccinimidyloxy (—$OC_4H_3O_2$—$SO_3H$), -1-oxybenzotriazolyl (—$OC_6H_4N_3$); or an aryloxy group or aryloxy substituted one or more times by electron withdrawing substituents such as nitro, fluoro, chloro, cyano, or trifluoromethyl, or combinations thereof, used to form activated aryl esters; or a carboxylic acid activated by a carbodiimide to form an anhydride or mixed anhydride —$OCOR^a$ or —$OCNR^aNHR^b$, where $R^a$ and $R^b$, which may be the same or different, are $C_1$-$C_6$ alkyl, $C_1$-$C_6$ perfluoroalkyl, or $C_1$-$C_6$ alkoxy; or cyclohexyl, 3-dimethylaminopropyl, or N-morpholinoethyl).
**Acyl azides can also rearrange to isocyanates The covalent linkage L binds the reactive group $R_x$ or conjugated substance $S_C$ to the compound, either directly (L is a single bond) or with a combination of stable chemical bonds, optionally including single, double, triple or aromatic carbon-carbon bonds, as well as carbon-nitrogen bonds, nitrogen-nitrogen bonds, carbon-oxygen bonds, carbon-sulfur bonds, phosphorus-oxygen bonds, phosphorus-nitrogen bonds, and nitrogen-platinum bonds. L typically includes ether, thioether, carboxamide, sulfonamide, urea, urethane or hydrazine moieties. In one embodiment, the covalent linkage incorporates a platinum atom, such as described in U.S. Pat. No. 5,714,327 (incorporated by reference). Preferred L moieties have 1-20 nonhydrogen atoms selected from the group consisting of C, N, O, P, and S; and are composed of any combination of ether, thioether, amine, ester, carboxamide, sulfonamide, hydrazide bonds and aromatic or heteroaromatic bonds. Preferably L is a combination of single carbon-carbon bonds and carboxamide or thioether bonds. The longest linear segment of the linkage L preferably contains 4-10 nonhydrogen atoms, including one or two heteroatoms. Examples of L include substituted or unsubstituted polymethylene, arylene, alkylarylene, arylenealkyl, or arylthio. In one embodiment, L contains 1-6 carbon atoms; in another, L comprises a thioether linkage. In yet another embodiment, L is or incorporates the formula $-(CH_2)_d(CONH(CH_2)_e)_{z'}-$, $(CH_2)_d(CONH(CH_2)_eNH_2)_{z'}-$, $-(CH_2)_d(CONH(CH_2)_eN-HCO)_{z'}$,

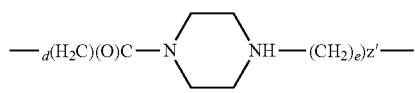

where d is 0-5, e is 1-5 and z' is 0 or 1. In one embodiment, -L is $-(CH_2)_d(CONH(CH_2)_e)_{z'}-$ and $-R_x$ is a carboxylic acid, or a succinimidyl ester of a carboxylic acid, a hydrazide, or a maleimide. In another embodiment, -L is $-(CH_2)_d(CONH(CH_2)_e)_{z'}-$, and $S_c$ is a conjugated substance that is an antibody or fragment thereof, a fluorescent protein, a lectin, an oligonucleotide, a small-molecule drug, an NTA, or a tyramide.

Choice of the reactive group used to attach the dye to the substance to be conjugated typically depends on the functional group on the substance to be conjugated and the type or length of covalent linkage desired. The types of functional groups typically present on the organic or inorganic substances include, but are not limited to, amines, amides, thiols, alcohols, phenols, aldehydes, ketones, phosphates, imidazoles, hydrazines, hydroxylamines, disubstituted amines, halides, epoxides, carboxylate esters, sulfonate esters, purines, pyrimidines, carboxylic acids, olefinic bonds, or a combination of these groups. A single type of reactive site may be available on the substance (typical for polysaccharides), or a variety of sites may occur (e.g. amines, thiols, alcohols, phenols), as is typical for proteins. A conjugated substance may be conjugated to more than one dye, which may be the same or different, or to a substance that is additionally modified by a hapten, such as biotin. Although some selectivity can be obtained by careful control of the reaction conditions, selectivity of labeling is best obtained by selection of an appropriate reactive dye.

Typically, $R_X$ will react with an amine, a thiol, an alcohol, an aldehyde or a ketone. Preferably $R_X$ reacts with an amine or a thiol functional group. In one embodiment, $R_X$ is an acrylamide, a reactive amine (including a cadaverine or ethylenediamine), an activated ester of a carboxylic acid (typically a succinimidyl ester of a carboxylic acid), an acyl azide, an acyl nitrile, an aldehyde, an alkyl halide, an anhydride, an aniline, an aryl halide, an azide, an aziridine, a boronate, a carboxylic acid, a diazoalkane, a haloacetamide, a halotriazine, a hydrazine (including hydrazides), an imido ester, an isocyanate, an isothiocyanate, a maleimide, a phosphoramidite, a reactive platinum complex, a sulfonyl halide, or a thiol group. In another embodiment, $R_x$ is a reactive group that is an activated ester of a carboxylic acid, an amine, a carboxylic acid, a halotriazine, a hydrazide, a maleimide, a reactive platinum complex. By "reactive platinum complex" is particularly meant chemically reactive platinum complexes such as described in U.S. Pat. Nos. 5,580,990; 5,714,327; 5,985,566 (all incorporated by reference).

Where the reactive group is a photoactivatable group, such as an azide, diazirinyl, azidoaryl, or psoralen derivative, the dye becomes chemically reactive only after illumination with light of an appropriate wavelength.

Where $R_x$ is an activated ester of a carboxylic acid, the reactive dye is particularly useful for preparing dye-conjugates of proteins, nucleotides, oligonucleotides, or haptens. Where $R_x$ is a maleimide or haloacetamide the reactive dye is particularly useful for conjugation to thiol-containing substances. Where $R_x$ is a hydrazide, the reactive dye is particularly useful for conjugation to periodate-oxidized carbohydrates and glycoproteins, and in addition is an aldehyde-fixable polar tracer for cell microinjection.

Preferably, $R_X$ is a carboxylic acid, a succinimidyl ester of a carboxylic acid, a haloacetamide, a hydrazine, an isothiocyanate, a maleimide group, an aliphatic amine, a perfluorobenzamido, an azidoperfluorobenzamido group, or a psoralen. More preferably, $R_X$ is a succinimidyl ester of a carboxylic acid, a maleimide, an iodoacetamide, or a reactive platinum complex. In a particular embodiment $R_X$ is a reactive platinum complex, or a succinimidyl ester of a carboxylic acid. Where $R_X$ is a reactive platinum complex, it is typically a haloplatinate or a platinum nitrate.

Figure 5:
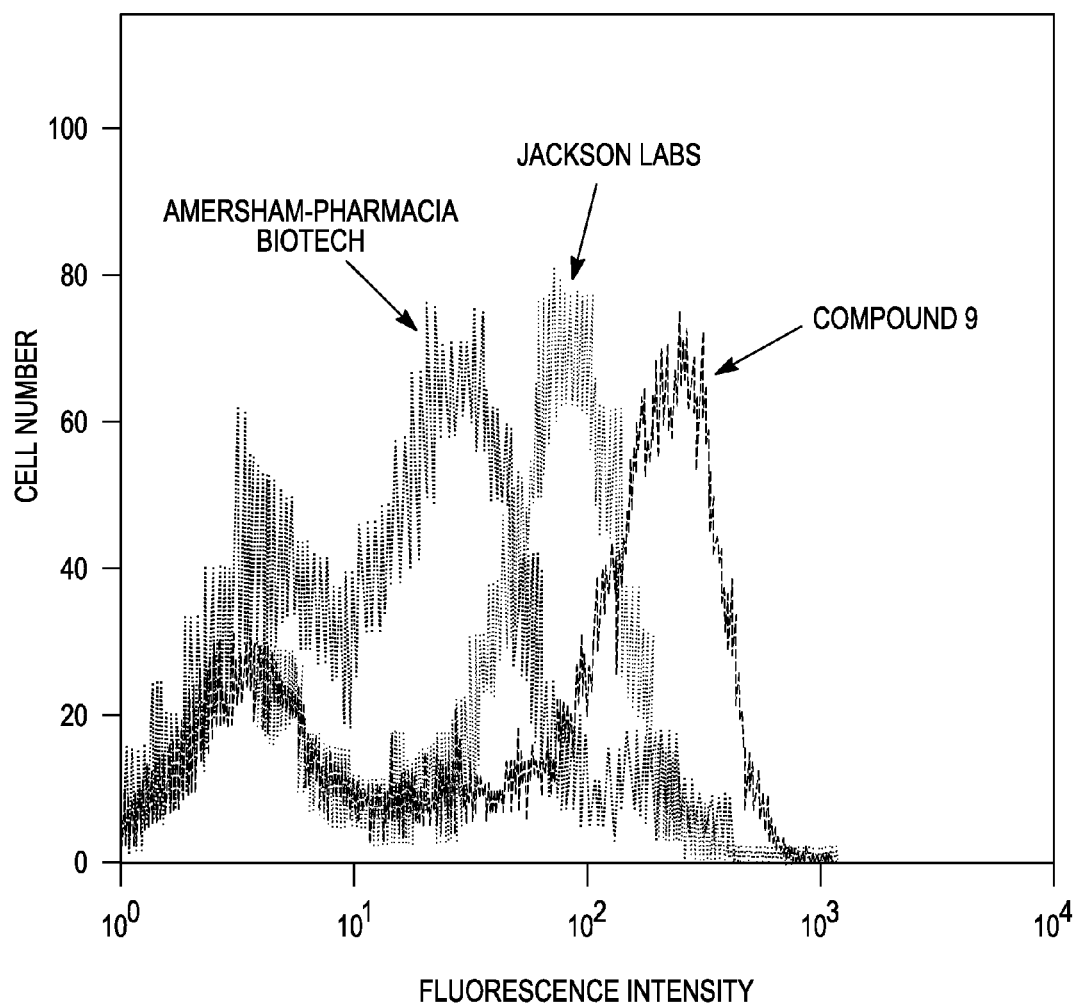
FIG. 5. Flow cytometric comparison of Compound-9 labeled GAM with the commercially available Cy5 GAM from Jackson Labs and Amersham-Pharmacia Biotech (see Example 72).
Figure 6:
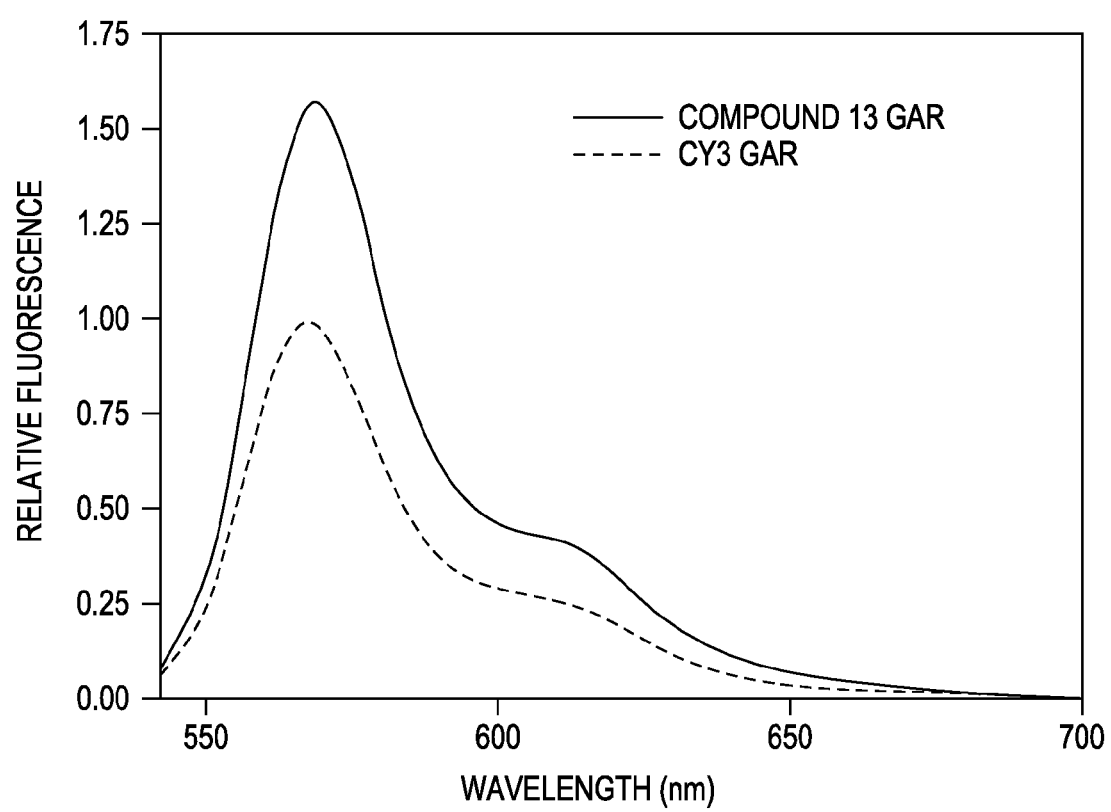
FIG. 6. Comparison of the fluorescence of goat anti-rabbit IgG (GAR) conjugates of Compound 13 (solid line) and those of the spectrally similar CY3 dye (dashed line) (see Example 73).
Figure 8:
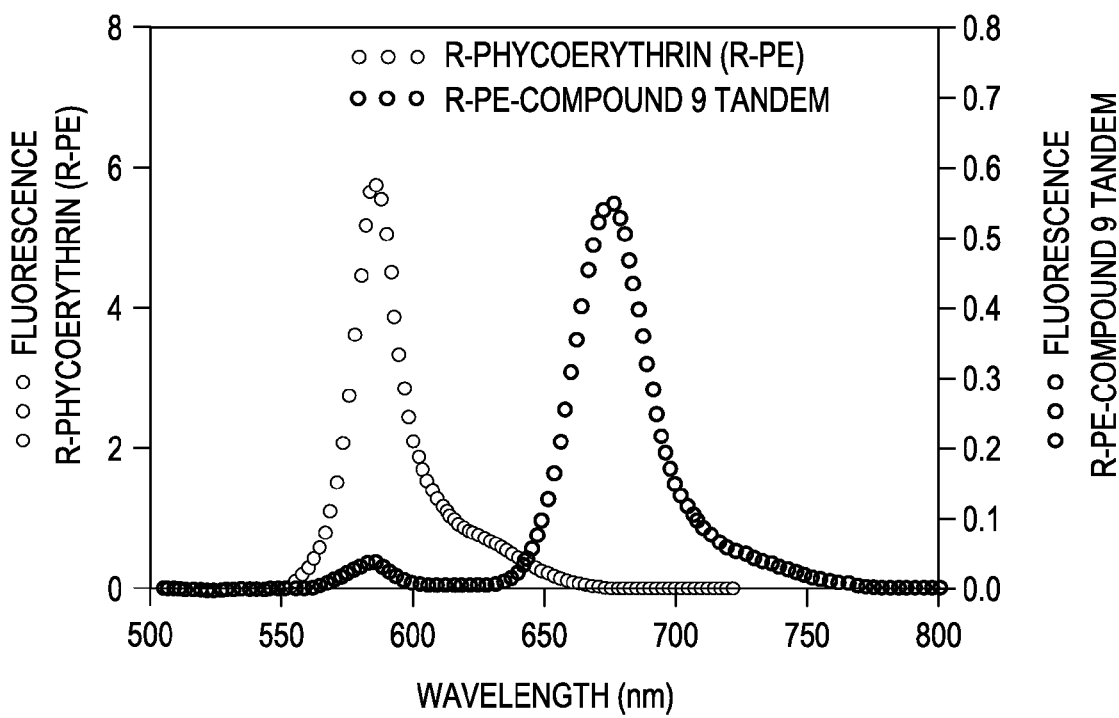
FIG. 8. Fluorescence energy-transfer from R-phycoerythrin to Compound 9 in a tandem conjugate (excitation=488 nm). Donor alone (open circles, left y-axis), donor-acceptor pair (closed circles, right y-axis) (see Example 76).
Figure 9:
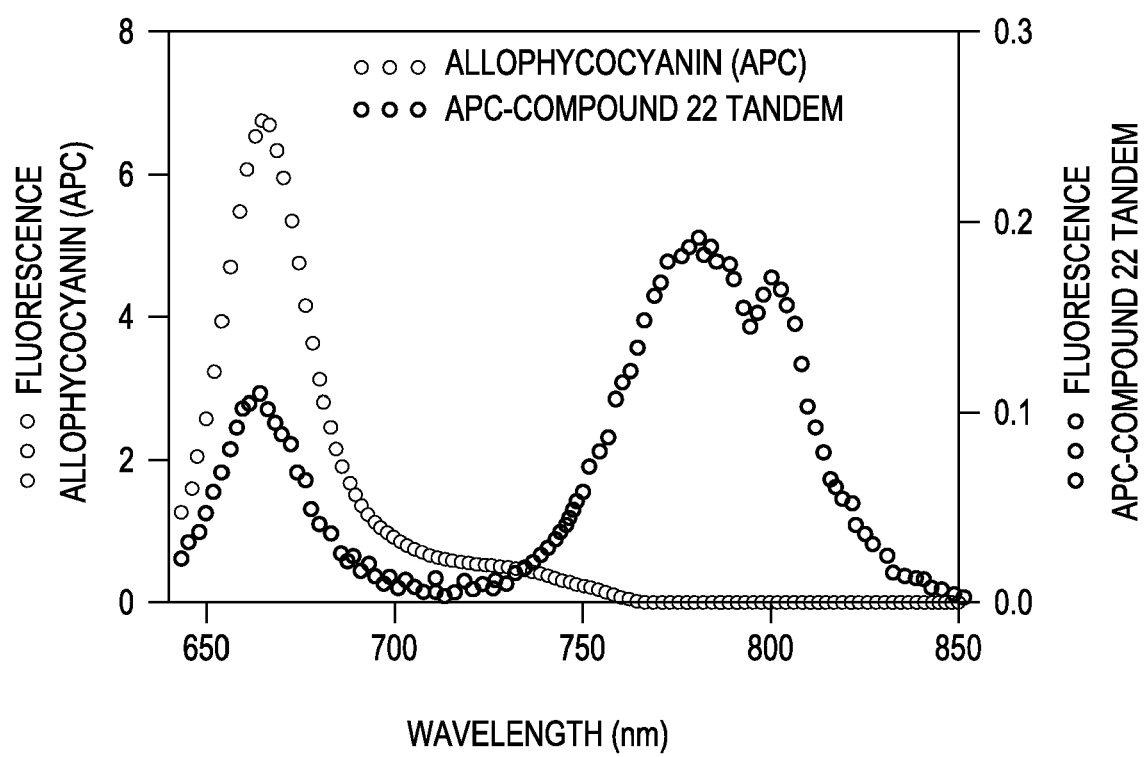
FIG. 9. Fluorescence energy-transfer from Allophycocyanin to Compound 22 in a tandem conjugate (excitation=633 nm). Donor alone (open circles, left y-axis), donor-acceptor pair (closed circles, right y-axis) (see Example 76).
Figure 10:
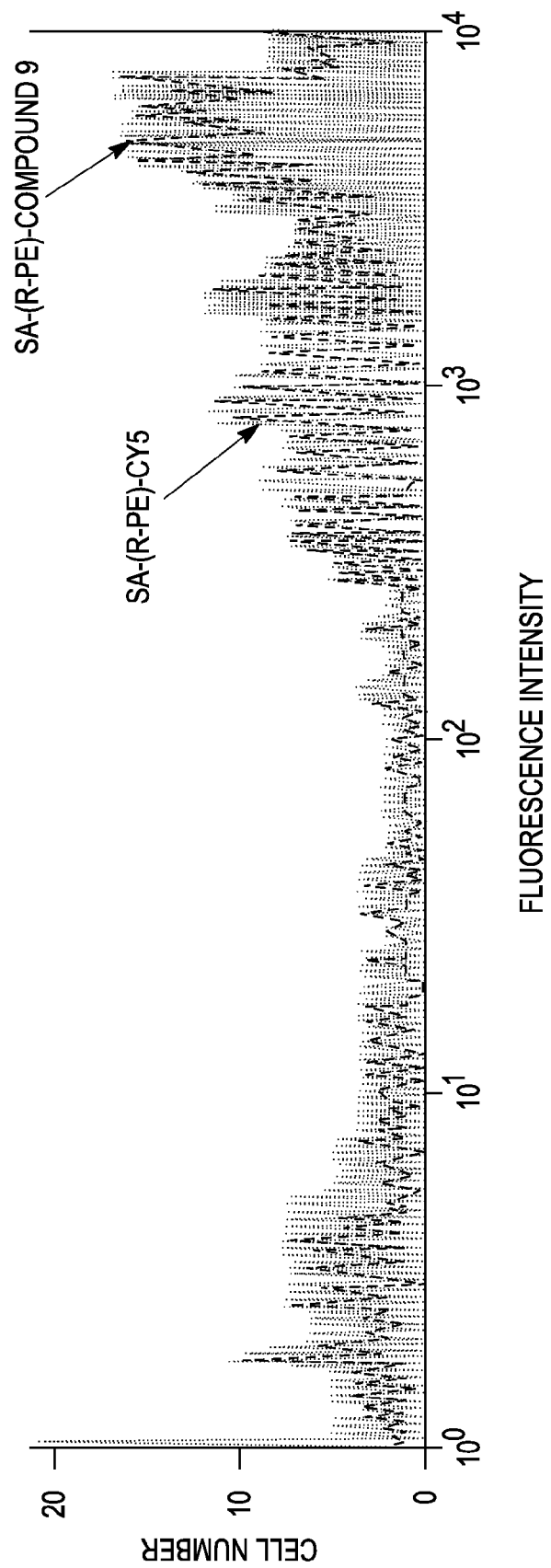
FIG. 10. Flow cytometric comparison of Streptavidin-(R-phycoerythrin) (SA-(R-PE)) conjugates of Compound 9 and Cy5 when targeted to a cell surface CD3 marker (see Example 77).
Figure 11:
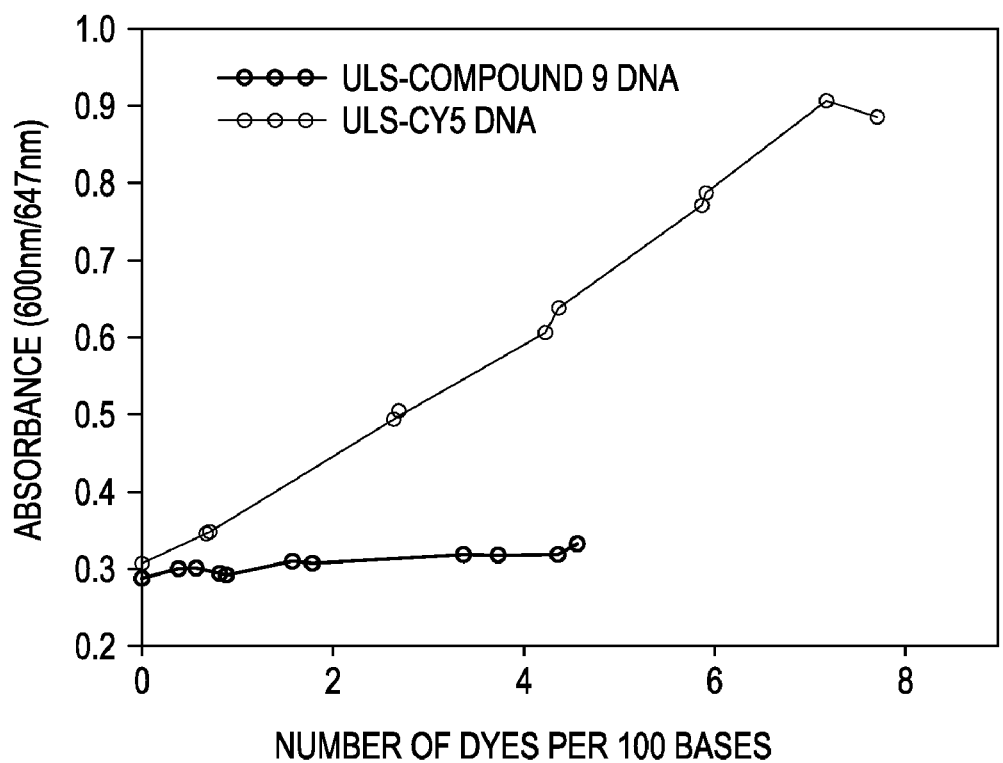
FIG. 11. Comparison of the change in absorbance of Compound 9 (closed circles) and Cy5 (open circles) upon DNA incorporation using ULS methodology (see Example 92).
Figure 12:
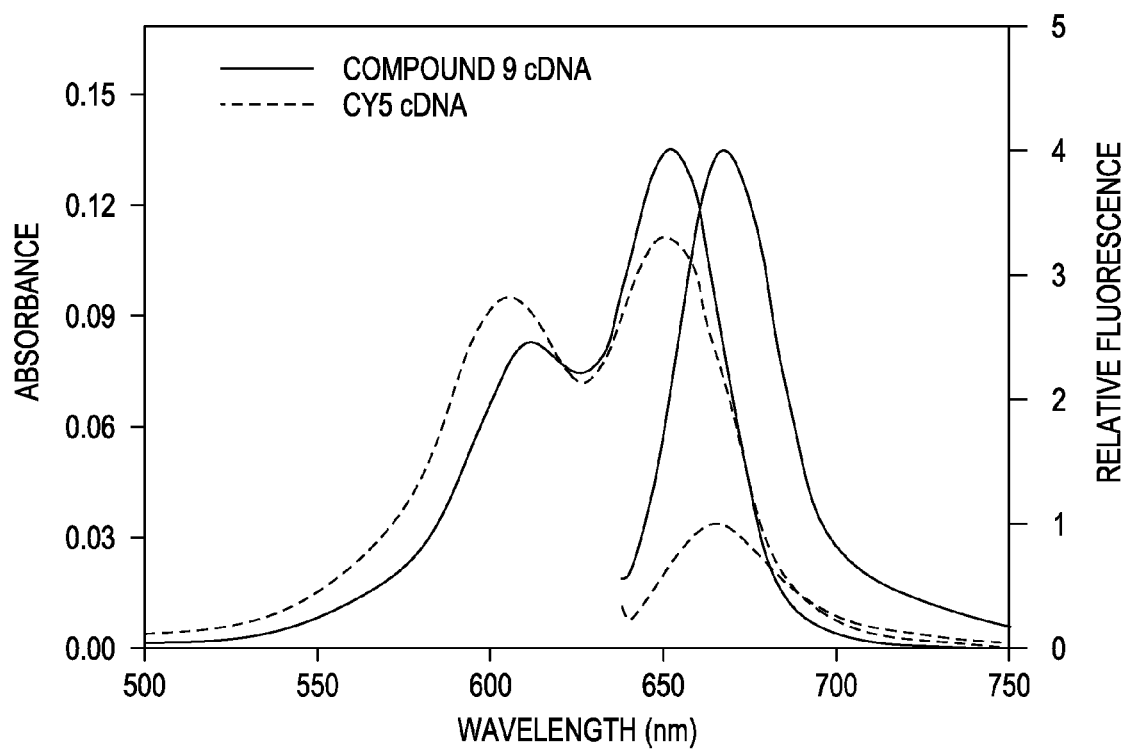
FIG. 12. Comparison of the absorption and fluorescence properties of identical concentrations of Compound 9 (solid line) and Cy5 (dashed line) labeled cDNA (see Example 94).
Figure 13:
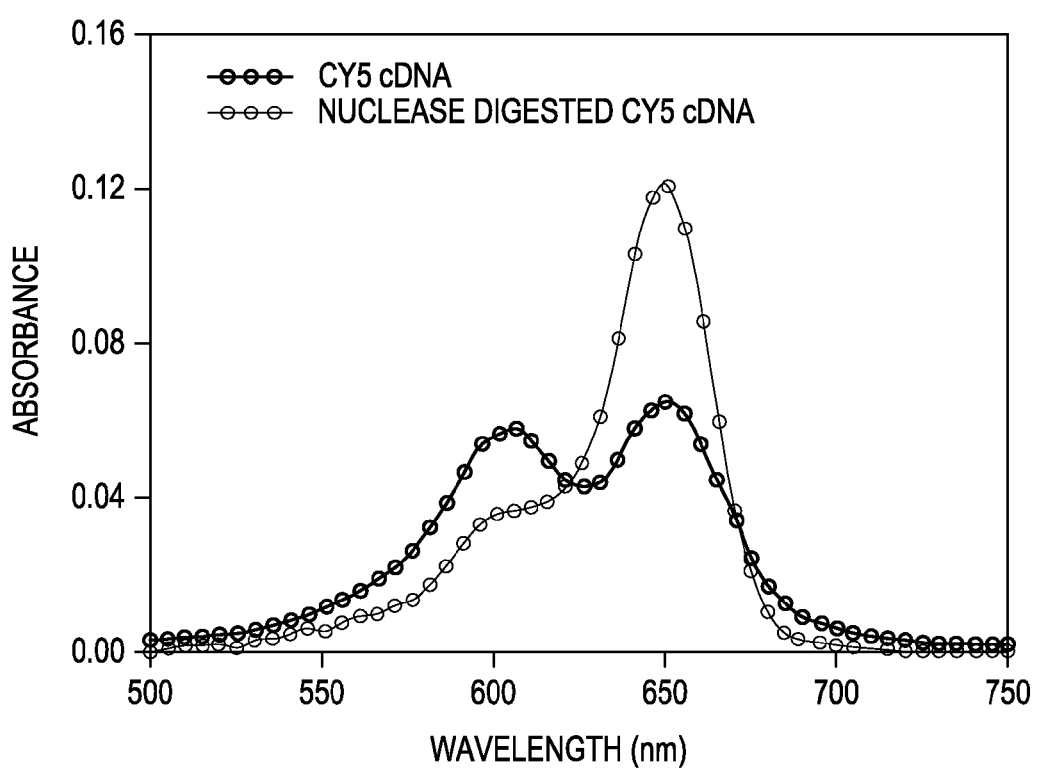
FIG. 13. Change in absorbance of Cy5 derivatives of cDNA upon digestion with micrococcal nuclease. Approximately one Cy5 dye for every 23 bases of DNA (see Example 94).

Based on the above-mentioned attributes, the appropriate reactive dye of the invention is selected for the preparation of the desired dye-conjugate, whose advantageous properties make them useful for a wide variety of applications. When compared to conjugates of widely used carbocyanine dyes for which the point of attachment is at the 1-position of the indolium moiety (e.g. Amersham's Cy Dyes™), the dye-conjugates of this invention have demonstrably superior optical properties. See, e.g. Example 73 and FIG. 6 comparing protein conjugates of Cy3 dye and spectrally similar conjugates of Compound 13 of the invention (wherein n=1); Tables 3 and 5 with an extensive comparison of protein conjugates of Cy5 dye with the spectrally similar conjugates of compound 9 of the invention (wherein n=2); Examples 68-69, 71-72, and 74; and FIGS. 2-3. See also, Example 76 and FIGS. 8 and 9 comparing dye-fluorophore conjugates; as well as Table 5, Examples 92-94, and FIGS. 11-13 comparing dye-nucleic acid conjugates; and Examples 72 and 77, and FIGS. 5 and 10 for flow-cytometric comparison of cell populations labeled with dye-conjugates. The desired dye-conjugate is selected based on the intended application.

Particularly useful dye-conjugates include, among others, conjugates where Sc is an antigen, steroid, vitamin, drug, hapten, metabolite, toxin, environmental pollutant, amino acid, peptide, protein, nucleic acid, nucleic acid polymer, carbohydrate, lipid, ion-complexing moiety, stable free radical or glass, plastic or other non-biological polymer. Alternatively, Sc is a cell, cellular system, cellular fragment, or subcellular particle, e.g. inter alia, a virus particle, bacterial particle, virus component, biological cell (such as animal cell, plant cell, bacteria, yeast, or protist), or cellular component. Reactive dyes typically label functional groups at the cell surface, in cell membranes, organelles, or cytoplasm.

Figure 2:
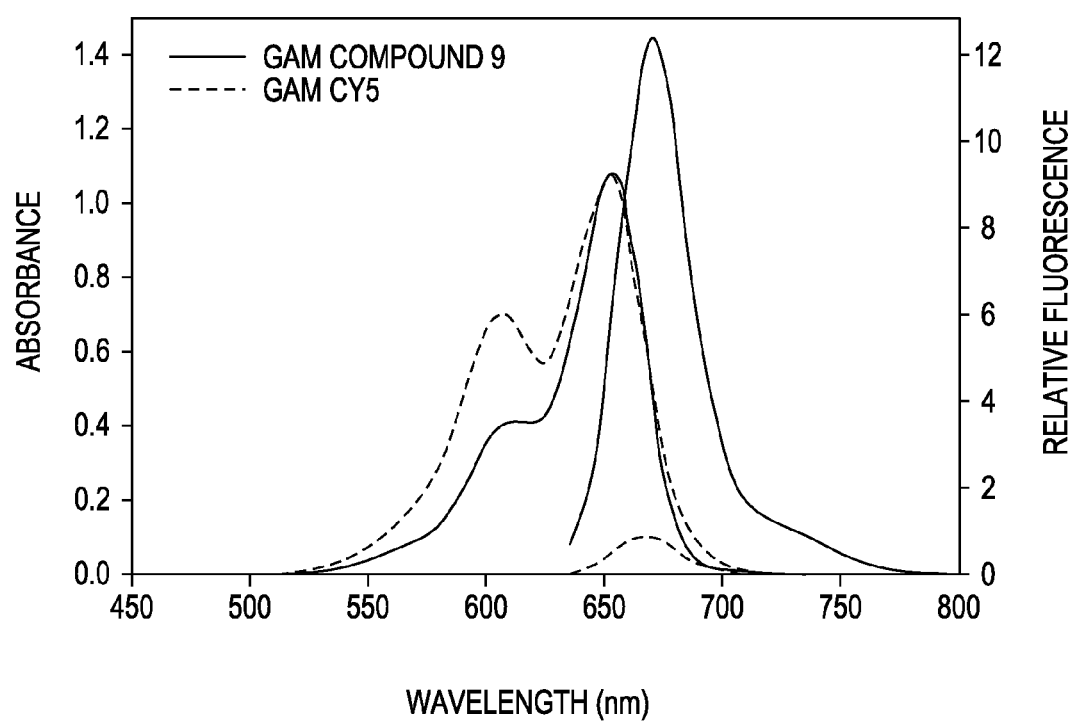
FIG. 2. Comparison of the absorption and emission spectra of Cy5 and Compound 9 when conjugated to Goat Anti-Mouse IgG (GAM) at DOS of ~4.8 and 4.2 respectively (see Example 68).

Typically Sc is an amino acid, peptide, protein, tyramine, polysaccharide, ion-complexing moiety, nucleoside, nucleotide, oligonucleotide, nucleic acid, hapten, psoralen, drug, hormone, lipid, lipid assembly, polymer, polymeric microparticle, biological cell or virus. More typically, Sc is a peptide, a protein, a nucleotide, an oligonucleotide, or a nucleic acid. When conjugating dyes of the invention to such biopolymers, it is possible to incorporate more dyes per molecule to increase the fluorescent signal. For example, it is possible to incorporate at least four molecules of such dyes per molecule of antibody without loss of total fluorescence, whereas fluorescence of the spectrally comparable Cy5 (wherein n=2) is strongly quenched when greater than approximately two Cy5 dyes are incorporated per antibody (Example 33 and 34, Table 3). These results confirm problems with Cy dye conjugates reported by others, e.g. BIOCONJUGATE CHEM. 11, 696 (2000). A comparison of commercially available Cy5 conjugates or conjugates of known dyes, and the optimally labeled conjugates of the invention are typically at least two-fold, usually more than three-fold and sometimes more than four-fold more fluorescent than conjugates of the Cy5 dye at the same antibody concentration (Table 3; FIGS. 2 and 5).

TABLE 3

| Protein | Source | Compound | DOS‡ | RQY† | TF§ |
|---|---|---|---|---|---|
| GAR IgG | Molecular Probes | 9 | 2.10 | 1.6 | 3.3 |
| GAR IgG | Molecular Probes | 9 | 3.0 | 1.4 | 4.3 |
| GAR IgG | Molecular Probes | 9 | 4.1 | 1.1 | 4.5 |
| GAR IgG | Molecular Probes | 9 | 5.2 | 0.9 | 4.7 |
| GAR IgG | Molecular Probes | 9 | 7.6 | 0.6 | 4.6 |
| GAR IgG | Molecular Probes | 9 | 8.2 | 0.5 | 4.1 |
| GAR IgG | Molecular Probes | Cy5 | 2.4 | 0.95 | 2.3 |
| GAR IgG | Molecular Probes | Cy5 | 4.1 | 0.5 | 2.1 |
| GAR IgG | Molecular Probes | Cy5 | 4.5 | 0.2 | 0.9 |
| GAR IgG | Molecular Probes | Cy5 | 5 | 0.3 | 1.5 |
| GAR IgG | Molecular Probes | Cy5 | 5.8 | 0.03 | 0.2 |
| GAR IgG | Jackson Labs | Cy5 | 2.2 | 1.1 | 2.4 |
| GAR IgG | Chemicon | Cy5 | 3.3 | 0.82 | 2.7 |
| GAR IgG | Zymed | Cy5 | 4.7 | 0.53 | 2.5 |
| GAR IgG | Amersham-Pharmacia Biotech | Cy5 | 5.7 | 0.22 | 1.3 |
| GAR IgG | Kirkegaard & Perry | Cy5 | 5.7 | 0.20 | 1.1 |
| GAR IgG | Rockland | Cy5 | 10.1 | 0.05 | 0.5 |
| GAR IgG | Molecular Probes | 30 | 2.7 | 0.7 | 1.9 |
| GAR IgG | Molecular Probes | 30 | 4.3 | 0.28 | 1.2 |
| GAR IgG | Molecular Probes | 30 | 5.4 | 0.10 | 0.5 |
| GAR IgG | Molecular Probes | 24 | 2.9 | 0.8 | 2.2 |
| GAR IgG | Molecular Probes | 24 | 4.3 | 0.33 | 1.4 |
| GAR IgG | Molecular Probes | 24 | 5.6 | 0.15 | 0.8 |
| GAR IgG | Molecular Probes | 25 | 2.0 | 0.7 | 1.4 |
| GAR IgG | Molecular Probes | 25 | 2.9 | 0.35 | 1.0 |
| GAR IgG | Molecular Probes | 25 | 3.9 | 0.13 | 0.5 |
| GAR IgG | Molecular Probes | 27 | 2.0 | 0.9 | 1.8 |
| GAR IgG | Molecular Probes | 27 | 3.2 | 0.52 | 1.6 |
| GAR IgG | Molecular Probes | 27 | 4.2 | 0.28 | 1.2 |
| GAR IgG | Molecular Probes | 26 | 1.4 | 0.58 | 0.81 |
| GAR IgG | Molecular Probes | 26 | 2.1 | 0.3 | 0.61 |
| GAR IgG | Molecular Probes | 26 | 2.9 | 0.1 | 0.29 |
| GAM IgG | Molecular Probes | 9 | 2.1 | 1.4 | 2.9 |
| GAM IgG | Molecular Probes | 9 | 2.2 | 1.4 | 3.1 |
| GAM IgG | Molecular Probes | 9 | 3.1 | 1.1 | 3.5 |
| GAM IgG | Molecular Probes | 9 | 4.2 | 1.2 | 5.0 |
| GAM IgG | Molecular Probes | 9 | 5.2 | 0.6 | 3.2 |
| GAM IgG | Jackson Labs | Cy5 | 1.9 | 1.0 | 1.9 |
| GAM IgG | Molecular Probes | Cy5 | 2 | 0.9 | 1.8 |
| GAM IgG | Molecular Probes | Cy5 | 3.3 | 0.5 | 1.6 |
| GAM IgG | Molecular Probes | Cy5 | 4.8 | 0.09 | 0.4 |
| Concanavalin A | Molecular Probes | 9 | 1.7 | 1.2 | 2.0 |
| Concanavalin A | Molecular Probes | 9 | 2.2 | 0.8 | 1.8 |
| Concanavalin A | Molecular Probes | 9 | 3.3 | 0.9 | 2.9 |
| Concanavalin A | Molecular Probes | 9 | 3.7 | 0.6 | 2.3 |
| Concanavalin A | Molecular Probes | 9 | 5.5 | 0.6 | 3.3 |
| Concanavalin A | Molecular Probes | 9 | 5.6 | 0.8 | 4.5 |
| Concanavalin A | Molecular Probes | Cy5 | 1.3 | 0.9 | 1.2 |
| Concanavalin A | Molecular Probes | Cy5 | 2.4 | 0.5 | 1.2 |
| Concanavalin A | Molecular Probes | Cy5 | 3.1 | 0.2 | 0.6 |
| Concanavalin A | Molecular Probes | Cy5 | 3.3 | 0.8 | 2.6 |
| Concanavalin A | Molecular Probes | Cy5 | 4.4 | 0.3 | 1.3 |
| Concanavalin A | Molecular Probes | Cy5 | 6.5 | 0.1 | 0.7 |
| Streptavidin | Molecular Probes | 9 | 2.2 | 2.4 | 5.4 |
| Streptavidin | Molecular Probes | 9 | 2.8 | 1.9 | 5.3 |
| Streptavidin | Molecular Probes | 9 | 3.4 | 1.9 | 6.5 |
| Streptavidin | Molecular Probes | 9 | 4.1 | 1.8 | 7.3 |
| Streptavidin | Molecular Probes | 9 | 4.5 | 1.7 | 7.6 |
| Streptavidin | Molecular Probes | 9 | 5.2 | 1.6 | 8.3 |
| Streptavidin | Molecular Probes | Cy5 | 1.6 | 1.8 | 2.8 |
| Streptavidin | Molecular Probes | Cy5 | 2.7 | 1.5 | 4.1 |
| Streptavidin | Jackson Labs | Cy5 | 3.3 | 1.8 | 6.0 |
| Streptavidin | Amersham-Pharmacia Biotech | Cy5 | 3.6 | 1.4 | 5.0 |
| Streptavidin | Molecular Probes | Cy5 | 3.6 | 1.4 | 5.0 |
| Transferrin | Molecular Probes | 9 | 1.8 | 1.5 | 2.7 |
| Transferrin | Molecular Probes | 9 | 2.7 | 1.3 | 3.5 |
| Transferrin | Molecular Probes | 9 | 3.7 | 1.2 | 4.4 |
| Transferrin | Molecular Probes | 9 | 4.2 | 1.1 | 4.4 |
| Transferrin | Molecular Probes | 9 | 5.8 | 0.7 | 4.1 |
| Transferrin | Molecular Probes | 9 | 5.9 | 0.6 | 3.5 |
| Transferrin | Molecular Probes | Cy5 | 0.8 | 1.1 | 0.9 |
| Transferrin | Molecular Probes | Cy5 | 1.4 | 0.8 | 1.1 |
| Transferrin | Molecular Probes | Cy5 | 2.7 | 0.5 | 1.4 |
| Transferrin | Molecular Probes | Cy5 | 3.0 | 0.7 | 2.1 |
| Transferrin | Molecular Probes | Cy5 | 5.3 | 0.1 | 0.5 |
| Transferrin | Molecular Probes | Cy5 | 5.8 | 0.02 | 0.1 |

†RQY (Relative Quantum Yield) is measured by matching absorbance between bioconjugate and DDAO (7-hydroxy-9H-(1,3-dichloro-9,9-dimethylacridine-2-one)), and comparing integrated fluorescence emission intensities.
‡DOS (Degree of Substitution) is the approximate molar ratio of the dye to protein following conjugation. DOS estimated using Molar Extinction coefficients of 250,000 $M^{-1}$ $cm^{-1}$ for Cy5 and 239,000 $M^{-1}$ $cm^{-1}$ for Compound 9 bioconjugates respectively, and protein extinction coefficients from the literature and a visible dye-correction term (at 280 nm) of 3-5%.
§TF (Total Fluorescence) is proportional to the overall brightness of the bioconjugate, and is defined as the product of the RQY and DOS: TF = RQY × DOS.

Alternatively, Sc is a ligand or a hapten, such as biotin. A preferred conjugate is a phenol such as a tyramine (e.g. as described in U.S. Pat. Nos. 5,196,306; 5,583,001; 5,731,158; all incorporated by reference), wherein the conjugate is useful as a substrate for horseradish peroxidase (Example 82).

In one embodiment, Sc is a biological polymer such as a peptide, protein, oligonucleotide, or nucleic acid polymer that is also labeled with at least a second non-fluorescent or fluorescent dye (optionally an additional dye of the present invention), to form an energy-transfer pair. In some aspects of the invention, the labeled conjugate functions as an enzyme substrate, and enzymatic hydrolysis disrupts the energy transfer. Alternatively, Sc is itself a fluorescent or nonfluorescent dye, optionally an additional dye of the present invention, which dye-conjugate forms a labeling complex that exhibits a large Stokes shift due to internal energy-transfer (as described in U.S. Pat. No. 6,008,373 above), which complex is useful to label an organic or inorganic substance (Examples 76-77; FIGS. 8-10).

In one embodiment, $S_C$ is an amino acid (including those that are protected or are substituted by phosphates, carbohydrates, or $C_1$ to $C_{22}$ carboxylic acids), or is a polymer of amino acids such as a peptide or protein. Preferred conjugates of peptides contain at least five amino acids, more preferably 5 to 36 amino acids. Preferred peptides include, but are not limited to, neuropeptides, cytokines, toxins, protease substrates, and protein kinase substrates. Preferred protein conjugates include enzymes, antibodies, lectins, glycoproteins, histones, albumins, lipoproteins, avidin, streptavidin, protein A, protein G, phycobiliproteins and other fluorescent proteins, hormones, toxins, chemokines and growth factors. In one preferred aspect, the conjugated protein is a phycobiliprotein, such as allophycocyanin, phycocyanin, phycoerythrin, allophycocyanin B, B-phycoerythrin, phycoerythrocyanin, and b-phycoerythrin (for example, see U.S. Pat. No. 5,714,386 to Roederer (1998), incorporated by reference).

Particularly preferred are conjugates of R-phycoerythrin and of allophycocyanin with selected dyes of the invention that serve as excited-state energy acceptors or donors. In these conjugates, excited state energy transfer results in long wavelength fluorescence emission when excited at relatively short wavelengths (Example 76, FIGS. 8 and 10). In another aspect of the invention, the conjugated protein is an antibody, an antibody fragment, avidin, streptavidin, a toxin, a lectin, a hormone, a chemokine, or a growth factor. Typically, where the conjugated substance is a toxin, it is a neuropeptide or a phallotoxin, such as phalloidin (Example 64).

In another embodiment, $S_C$ is a nucleic acid base, nucleoside, nucleotide (Example 87) or a nucleic acid polymer (Examples 88-93), including those that are modified to possess an additional linker or spacer for attachment of the dyes of the invention, such as an alkynyl linkage (U.S. Pat. No. 5,047,519), an aminoallyl linkage (U.S. Pat. No. 4,711,955), or a heteroatom-substituted linker (U.S. Pat. No. 5,684,142) (all patents incorporated by reference), or other linkage. In another embodiment, the conjugated substance is a nucleoside or nucleotide analog that links a purine or pyrimidine base to a phosphate or polyphosphate moiety through a noncyclic spacer. In a third embodiment, the dye is conjugated to the carbohydrate portion of a nucleotide or nucleoside, typically through a hydroxyl group but additionally through a thiol or amino group (U.S. Pat. No. 5,659,025, U.S. Pat. No. 5,668,268, U.S. Pat. No. 5,679,785; all incorporated by reference). Typically, the conjugated nucleotide is a nucleoside triphosphate or a deoxynucleoside triphosphate or a dideoxynucleoside triphosphate. Typically, the nucleotide is a cytidine or uridine or deoxy or dideoxy cytidine or uridine. Incorporation of methylene moieties or nitrogen or sulfur heteroatoms into the phosphate or polyphosphate moiety is also useful. Nonpurine and nonpyrimidine bases such as 7-deazapurines (U.S. Pat. No. 6,150,510, incorporate by reference) and nucleic acids containing such bases can also be coupled to dyes of the invention. Nucleic acid adducts prepared by reaction of depurinated nucleic acids with amine, hydrazide or hydroxylamine derivatives provide an additional means of labeling and detecting nucleic acids, e.g. "A method for detecting abasic sites in living cells: age-dependent changes in base excision repair." Atamna H, Cheung I, Ames B N. Proc Natl Acad Sci USA 97, 686-691 (2000); incorporated by reference.

Preferred nucleic acid polymer conjugates are labeled, single- or multi-stranded, natural or synthetic DNA or RNA, DNA or RNA oligonucleotides, or DNA/RNA hybrids, or incorporate an unusual linker such as morpholine derivatized phosphates (AntiVirals, Inc., Corvallis Oreg.), or peptide nucleic acids such as N-(2-aminoethyl)glycine units. When the nucleic acid is a synthetic oligonucleotide, it typically contains fewer than 50 nucleotides, more typically fewer than 25 nucleotides. Conjugates of peptide nucleic acids (PNA) (Nielsen et al U.S. Pat. No. 5,539,082, incorporated by reference) may be preferred for some applications because of their generally faster hybridization rates.

Fluorescent nucleic acid polymers are typically prepared from labeled nucleotides or oligonucleotides using oligonucleotide-primed DNA polymerization (Example 93), such as by using the polymerase chain reaction or through primer extension, or by terminal-transferase catalyzed addition of a labeled nucleotide to a 3'-end of a nucleic acid polymer. Fluorescent RNA polymers are typically prepared from labeled nucleotides by transcription. Typically, the dye is attached via one or more purine or pyrimidine bases through an amide, ester, ether or thioether bond; or is attached to the phosphate or carbohydrate by a bond that is an ester, thioester, amide, ether or thioether. Alternatively, dye conjugate of the invention is simultaneously labeled with a hapten such as biotin or digoxigenin, or to an enzyme such as alkaline phosphatase, or to a protein such as an antibody. Nucleotide conjugates of the invention are readily incorporated by DNA polymerase and can be used for in situ hybridization and nucleic acid sequencing (e.g., U.S. Pat. Nos. 5,332,666; 5,171,534; and 4,997,928, and WO Appl. 94/05688; all incorporated by reference). In another aspect of the invention, the oligonucleotide incorporates an aliphatic amine, which is subsequently conjugated to an amine-reactive dye of the invention or a thiol or thiophosphate, which is conjugated to a thiol-reactive dye of the invention. In yet another aspect of the invention, the purine bases of the oligonucleotide react with a reactive metal complex (preferably a platinum complex) bound to a dye of the invention, yielding a dye-conjugate (Example 92). Nucleic acid conjugates of dyes of the invention that are linked at the 3-position of the indolium ring unexpectedly have spectral properties that are superior to those of structurally similar carbocyanine dyes wherein the dye is not linked at the 3-position of the indolium ring (Examples 92-94, FIGS. 11-12, Table 8).

In one embodiment, the conjugated oligonucleotides of the invention are aptamers for a particular target molecule, such as a metabolite, dye, hapten, or protein. That is, the oligonucleotides have been selected to bind preferentially to the target molecule. Methods of preparing and screening aptamers for a given target molecule have been previously described and are known in the art (for example, U.S. Pat. No. 5,567,588 to Gold (1996), incorporated by reference).

In another embodiment, the conjugated substance ($S_c$) is a carbohydrate that is typically a polysaccharide, such as a dextran, FICOLL™, heparin, glycogen, amylopectin, mannan, inulin, starch, agarose and cellulose. Alternatively, the carbohydrate is a polysaccharide that is a lipopolysaccharide. Preferred polysaccharide conjugates are dextran, FICOLL™, or lipopolysaccharide conjugates.

In another embodiment, the conjugated substance ($S_c$), is a lipid (typically having 6-60 carbons), including glycolipids, phospholipids, sphingolipids, and steroids. Alternatively, the conjugated substance is a lipid assembly, such as a liposome. The lipophilic moiety may be used to retain the conjugated substances in cells, as described in U.S. Pat. No. 5,208,148 (incorporated by reference). Certain polar dyes of the invention may also be trapped within lipid assemblies.

Conjugates having an ion-complexing moiety serve as indicators for calcium, sodium, magnesium, zinc, potassium, or other biologically important metal ions. Preferred ion-complexing moieties are crown ethers (U.S. Pat. No. 5,405,975 and provisional patent application titled "Crown Ether Derivatives", filed Dec. 19, 2000 by Martin et al. U.S. Ser. No. 60/258,266, both incorporated by reference); derivatives of 1,2-bis-(2-aminophenoxyethane)-N,N,N',N'-tetraacetic acid (BAPTA chelators; U.S. Pat. No. 5,453,517, U.S. Pat. No. 5,516,911, and U.S. Pat. No. 5,049,673, all incorporated by reference); derivatives of 2-carboxymethoxyaniline-N,N-diacetic acid (APTRA chelators; AM. J. PHYSIOL. 256, C540 (1989), incorporated by reference); or pyridine- and phenanthroline-based metal ion chelators (U.S. Pat. No. 5,648,270, incorporated by reference); or derivatives of nitrilotriacetic acid (NTA), see e.g. "Single-step synthesis and characterization of biotinylated nitrilotriacetic acid, a unique reagent for the detection of histidine-tagged proteins immobilized on nitrocellulose", McMahan S A, Burgess R R. Anal Biochem 236, 101-106 (1996); incorporated by reference. Preferably, the ion-complexing moiety is a crown ether chelator, a BAPTA chelator, an APTRA chelator or a derivative of nitrilotriacetic acid.

Other conjugates of non-biological materials include dye-conjugates of organic or inorganic polymers, polymeric films, polymeric wafers, polymeric membranes, polymeric particles, or polymeric microparticles (Example 84); including magnetic and non-magnetic microspheres; iron, gold or silver particles; conducting and non-conducting metals and non-metals; and glass and plastic surfaces and particles. Conjugates are optionally prepared by copolymerization of a dye that contains an appropriate functionality while preparing the polymer, or by chemical modification of a polymer that contains functional groups with suitable chemical reactivity. Other types of reactions that are useful for preparing dye-conjugates of polymers include catalyzed polymerizations or copolymerizations of alkenes and reactions of dienes with dienophiles, transesterifications or transaminations. In another embodiment, the conjugated substance is a glass or silica, which may be formed into an optical fiber or other structure.

In one aspect of the invention, $S_c$ is a conjugated substance that is an antibody (including intact antibodies, antibody fragments, and antibody sera, etc.), an amino acid, blood vessel proliferation inhibition factors (including Angiostatin™, Endostatin™, etc.), an avidin or streptavidin, a biotin (e.g. an amidobiotin, a biocytin, a desthiobiotin, etc.), a blood component protein (e.g. an albumin, a fibrinogen, a plasminogen, etc.), a dextran, an enzyme, an enzyme inhibitor, an IgG-binding protein (e.g. a protein A, protein G, protein A/G, etc.), a fluorescent protein (e.g. a phycobiliprotein, an aequorin, a green fluorescent protein, etc.), a growth factor, a hormone, a lectin (e.g. a wheat germ agglutinin, a conconavalin A, etc.), a lipopolysaccharide, a metal-binding protein (e.g. a calmodulin, etc.), a microorganism or portion thereof (e.g. a bacteria, a virus, a yeast, etc.), a neuropeptide and other biologically active factors (e.g. a dermorphin, a deltropin, an endomorphin, an endorphin, a tumor necrosis factor etc.), a non-biological microparticle (e.g. of ferrofluid, gold, polystyrene, etc.), a nucleotide, an oligonucleotide, a peptide toxin (e.g. an apamin, a bungarotoxin, a phalloidin, etc.), a phospholipid-binding protein (e.g. an annexin, etc.), a small-molecule drug (e.g. a methotrexate, etc.), a structural protein (e.g. an actin, a fibronectin, a laminin, a microtubule-associated protein, a tublin, etc.), an NTA, or a tyramide. Typically, $S_c$ is a conjugated substance that is an antibody, an amino acid, an avidin or streptavidin, a biotin, blood vessel proliferation inhibition factor, a blood component protein, a dextran, an enzyme, an enzyme inhibitor, a hormone, an IgG-binding protein, a fluorescent protein, a growth factor, a lectin, a lipopolysaccharide, a metal-binding protein, a microorganism or portion thereof, a neuropeptide, a non-biological microparticle, a nucleotide, an oligonucleotide, a peptide toxin, a phospholipid-binding protein, a small-molecule drug, a structural protein, an NTA, or a tyramide Preferably, $S_c$ is a conjugated substance that is an actin, an antibody or fragment thereof, an avidin or streptavidin, a biotin, a dextran, an enzyme, a fluorescent protein, a lectin, a lipopolysaccharide, a microorganism, a non-biological microparticle, a nucleotide, an oligonucleotide, a peptide toxin, a phosphotidylserine-binding protein, a protein A or G, a small-molecule drug, an NTA, or a tyramide. In another embodiment, where $R^3$ is a reactive group, another substituent contains a conjugated substance $S_c$ that is an amino acid, peptide, polypeptide, protein, nucleotide, oligonucleotide, nucleic acid polymer, a sugar, a polysaccharide, an oligosaccharide, a fluorescent dye, or a microsphere.

In one embodiment, conjugates of biological polymers such as peptides, proteins, oligonucleotides, nucleic acid polymers are also labeled with at least a second fluorescent or nonfluorescent dye, that is optionally an additional dye of the present invention, to form an energy-transfer pair. In some aspects of the invention, the labeled conjugate functions as an enzyme substrate, and enzymatic hydrolysis disrupts the energy transfer. Alternatively, the conjugated substance is itself a fluorescent or nonfluorescent dye, optionally an additional dye of the present invention, that forms a labeling complex that exhibits a large Stokes shift due to internal energy-transfer (as described in U.S. Pat. No. 6,008,373 to Waggoner et al., (1999), incorporated by reference). In another embodiment of the invention, the energy-transfer pair that incorporates a dye of the invention is conjugated to an oligonucleotide that displays efficient fluorescence quenching in its hairpin conformation (the so-called "molecular beacons" of Tyagi et al., NATURE BIOTECHNOLOGY 16, 49 (1998) incorporated by reference) or fluorescence energy transfer.

The preparation of dye conjugates using reactive dyes is well documented, e.g. by R. Haugland, MOLECULAR PROBES HANDBOOK OF FLUORESCENT PROBES AND RESEARCH CHEMICALS, Chapters 1-3 (1996); and Brinkley, BIOCONJUGATE CHEM., 3, 2 (1992). Conjugates typically result from mixing appropriate reactive dyes and the substance to be conjugated in a suitable solvent in which both are soluble. The majority of the dyes of the invention are readily soluble in aqueous solutions, facilitating conjugation reactions with most biological materials. For those reactive dyes that are photoactivated, conjugation requires illumination of the reaction mixture to activate the reactive dye.

Labeled members of a specific binding pair are typically used as fluorescent probes for the complementary member of that specific binding pair, each specific binding pair member having an area on the surface or in a cavity that specifically binds to and is complementary with a particular spatial and polar organization of the other. Preferred specific binding pair members are proteins that bind non-covalently to low molecular weight ligands, such as biotin, drug-haptens and fluorescent dyes (such as an anti-fluorescein antibody). Representative specific binding pairs are shown in Table 4.

TABLE 4

Representative Specific Binding Pairs

| antigen | antibody |
|---|---|
| biotin | avidin (or streptavidin or anti-biotin) |
| IgG* | protein A or protein G |
| drug | drug receptor |
| toxin | toxin receptor |
| carbohydrate | lectin or carbohydrate receptor |
| peptide | peptide receptor |
| protein | protein receptor |
| enzyme substrate | enzyme |
| DNA (RNA) | aDNA (aRNA)† |
| hormone | hormone receptor |
| ion | chelator |
| psoralen | nucleic acid |
| target molecule | RNA or DNA aptamer |

*IgG is an immunoglobulin
†aDNA and aRNA are the antisense (complementary) strands used for hybridization Synthesis Synthesis of the carbocyanine dyes of the invention, where attachment is at the 3-position of the indolium, depends on initial preparation of certain key intermediates. The intermediates have the following general structure (for simplicity, all but a few of the possible substituents are shown as hydrogen):

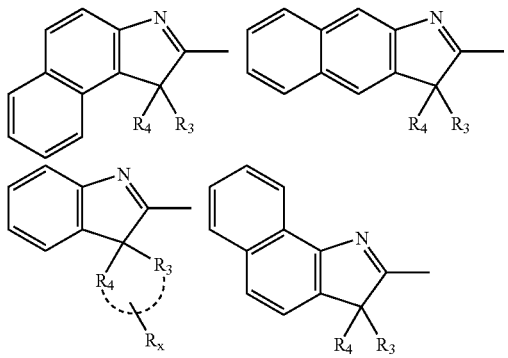

These basic structures are optionally further substituted, during or after synthesis, to give the corresponding dye substituents as defined above.

The novel key intermediates are readily synthesized by a reaction that is analogous to a Fischer indole synthesis (where X is a desired substituent on the resulting indolium, typically sulfo, and $R^3$ and $R^4$ are as defined above):

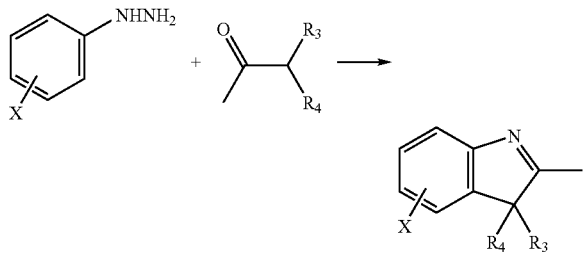

In this reaction, an appropriately substituted aryl hydrazine, which is typically a phenylhydrazine of an appropriately substituted naphthyl hydrazine, is reacted with an appropriately substituted methyl ketone to yield a 3,3-disubstituted 2-methylindoline derivative. One of the 3-position substituents is selected to be a chemically reactive moiety or a group that is converted to a chemically reactive moiety such as a carboxylic acid derivative (Examples 1, 2, 7), an alcohol (Example 16) or an amine (Example 17). It is particularly suitable to utilize a sulfonated phenylhydrazine derivative (as in Examples 1-3) or a sulfonated naphthylhydrazine derivative (as in Example 25) to increase the solubility of the final dye. The 3,3-disubstituted-2-methylindole is then quaternized on the nitrogen atom to an indolium derivative with an alkylating agent that is typically an alkyl halide such as ethyl iodide, an alkylsulfonate such as methyl p-toluenesulfonate (Example 7) or a cyclic sulfonate such as propanesultone or butanesultone (Examples 2-3). Typically, the key indolium or benzoindolium intermediates are sulfonated one or more times before or after quaternization at $R^2$ and subsequent condensation with the benzazolium moiety and polymethine moiety to form the subject dyes. Methods for synthesis of dyes wherein n=1, n=2 and n=3 are provided in Examples 12, 8, and 21, respectively. Variations on these methods are well known in the art that yield substituents on the polymethine bridge or on the indolium or benzolium portion of the dye precursor.

In one embodiment, the synthetic intermediate is a compound of the formula:

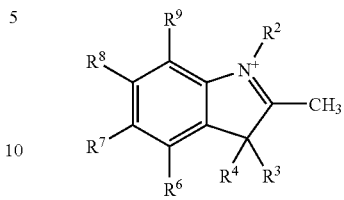

or its salts, wherein $R^3$ is $C_3$-$C_7$ carboxyalkyl; and $R^4$ is a $C_1$-$C_6$ alkyl; $R^2$ is H or a $C_1$-$C_6$ alkyl or $C_1$-$C_6$ alkyl substituted by sulfo; $R^6$ through $R^9$ are independently H, amino, sulfo, trifluoromethyl, or halogen; or $C_1$-$C_6$ alkyl, $C_1$-$C_6$ alkoxy, $C_1$-$C_6$ alkylamino, $C_2$-$C_{12}$ dialkylamino, each of which is optionally further substituted by carboxy, sulfo, amino, or hydroxy; or any two adjacent substituents of $R^6$ through $R^9$ form a fused benzo ring that is optionally substituted one or more times by amino, sulfo, trifluoromethyl, or halogen; or by $C_1$-$C_6$ alkyl, $C_1$-$C_6$ alkoxy, $C_1$-$C_6$ alkylamino, $C_2$-$C_{12}$ dialkylamino, each of which is optionally further substituted by carboxy, sulfo, amino, or hydroxy. In a preferred embodiment, $R^3$ is $C_5$-$C_6$ carboxyalkyl; and $R^4$ is methyl; $R^2$ is methyl or sulfopropyl; and $R^6$ and $R^7$ form a fused benzo ring that is optionally substituted one or more times by sulfo; or $R^7$ is independently H or sulfo, and $R^6$ is H; both $R^8$ and $R^9$ are H.

A useful synthetic route to the azacarbocyanine dyes of the present invention can be described in three parts, following the natural breakdown in the description of the compounds. In general, the synthesis of these dyes requires three precursors: the appropriate benzazolium or azabenzazolium salt (the "A" and "B" moieties), and a source for the polymethine spacer. Typically each component is selected so as to incorporate the appropriate chemical substituents, or functional groups that can be converted to the appropriate substituents. The chemistry that is required to prepare and combine these precursors so as to yield any of the subject derivatives is generally well understood by one skilled in the art. Although there are many possible variations that may yield an equivalent result, we provide herein some useful general methods for their synthesis and incorporation of chemical modifications.

Although the chemically reactive azabenzazolium dyes and their conjugates described herein have not previously been described, a variety of nonreactive azabenzazolium derivatives have been previously described (see, for example, Brooker, et al., J. AM. CHEM. SOC., 64, 199 (1942); Heravi, et al., INDIAN J. CHEM. 36B, 1025 (1997); Smith et al. SULFUR LETTERS 17, 197 (1994); Chu-Moyer et al. J. ORG. CHEM. 60, 5721 (1995); Turner, J. ORG. CHEM. 48, 3401 (1983); Couture et al. J. HETEROCYCLIC CHEM. 24, 1765 (1987); Petric et al. J. HETEROCYCLIC CHEM. 14, 1045, (1977); Barlin et al. AUST. J. CHEM., 37, 1729 (1984); Saikachi et al. CHEM. & PHARM. BULL. 9, 941 (1961); Barlin AUST. J. CHEM. 36, 983 (1983); Foye et al., J. PHARM. SCI. 64, 1371 (1975); Khanna et al. J. ORG. CHEM. 60, 960 (1995)); British Patent No. 870,753 to Ficken et al. (1961); Ficken et al., "Diazaindenes and Their Quaternary Salts-Part I" pp 3202-3212 (1959); Ficken et al., "Diazaindenes and Their Quaternary Salts-Part II" pp 584-588 (1961). Synthetic methods for preparing some azabenzazolium precursors have also been described in copending application Ser. No. 09/557,275 by Haugland et al., filed Apr. 24, 2000, hereby incorporated by reference.

The substituents on the aromatic carbons of the azabenzazolium moiety are typically incorporated in the parent aza- or polyazabenzazole molecule prior to quaternization with an alkylating agent. However, such substituents may also be incorporated during the synthesis of the azabenzazole moiety. $R^2/R^{12}$ is usually obtained by alkylation of the parent heterocycle with an alkylating agent that incorporates the desired $R^2/R^{12}$ moiety.

The B moiety intermediate is optionally an azabenzazolium precursor, as described above, or is a benzazolium precursor, as well known in the art (for example, U.S. Pat. No. 5,436,134 to Haugland et al., (1995), incorporated by reference). The B moiety is optionally fused to additional rings, resulting in dyes that absorb and emit at longer wavelengths (for example, see U.S. Pat. No. 6,027,709 to Little et al. (2000), incorporated by reference).

Alkyl, alkoxy, carboxyl, and halogen substituents at aromatic carbons are typically already present as substituents on the benzazole or azabenzazole precursors, or on compounds that are readily converted to such precursors using methods well-known in the art. Sulfonic acid groups are typically introduced on the precursors prior to condensation of the cyanine dye (for example, see U.S. Pat. No. 5,767,287 to Bobrow et al. (1998), incorporated by reference). Aminoalkyl groups are typically substituted by a protecting group when they are first introduced, typically by substitution onto the benzazole or azabenzazole precursor. The protecting group is then removed after condensation of the cyanine dye. Aromatic amino groups are typically prepared via the reduction of a nitro substituted benzazolium precursor, which in turn is prepared by the nitration of the benzazole precursor.

The BRIDGE moiety typically originates from the coupling agent used in the dye construction. For example, N,N'-diphenylformamidine and triethylorthoformate yields BRIDGE moieties wherein a and b are both zero. Malonaldehyde bis(phenylimine) hydrochloride, 1,1,3-trimethoxypropane, and 1,1,3,3-tetramethoxypropane yield dyes wherein one of a and b is 1, and glutaconaldehyde dianil monochloride yields dyes wherein both a and b are 1.

The methods for synthesis of dyes that contain a variety of reactive groups such as those described in Table 2 are well documented in the art. Particularly useful are amine-reactive dyes such as "activated esters" of carboxylic acids, which are typically synthesized by coupling a carboxylic acid to a relatively acidic "leaving group". Other preferred amine-reactive groups include sulfonyl halides, which are prepared from sulfonic acids using a halogenating agent such as $PCl_5$ or $POCl_3$; halotriazines, which are prepared by the reaction of cyanuric halides with amines; and isothiocyanates or isothiocyanates, which are prepared from amines and phosgene or thiophosgene, respectively.

Dyes containing amines and hydrazides are particularly useful for conjugation to carboxylic acids, aldehydes and ketones. Most often these are synthesized by reaction of an activated ester of a carboxylic acid or a sulfonyl halide with a diamine, such as cadaverine, or with a hydrazine. Alternatively, aromatic amines are commonly synthesized by chemical reduction of a nitroaromatic compound. Amines and hydrazines are particularly useful precursors for synthesis of thiol-reactive haloacetamides or maleimides by standard methods.

Nucleosides and nucleotides labeled with dyes of the invention are particularly useful for some applications of nucleic acid labeling. The use of carbocyanine-amidites for labeling nucleotides and nucleosides have been previously described (U.S. Pat. No. 5,986,086 to Bruch et al. (1999); U.S. Pat. No. 5,808,044 to Brush et al. (1998); U.S. Pat. No. 5,556,959 to Brush et al. (1996); all incorporated by reference).

Examples of some synthetic strategies for selected dyes of the invention, as well as their characterization, synthetic precursors, conjugates and method of use are provided in the examples below. Further modifications and permutations will be obvious to one skilled in the art.

Applications and Methods of Use

In one aspect of the invention, the dye compounds of the invention are used to directly stain or label a sample so that the sample can be identified or quantitated. For instance, such dyes may be added as part of an assay for a biological target analyte, as a detectable tracer element in a biological or non-biological fluid; or for such purposes as photodynamic therapy of tumors, in which a dyed sample is irradiated to selectively destroy tumor cells and tissues; or to photoablate arterial plaque or cells, usually through the photosensitized production of singlet oxygen. In one preferred embodiment, the dye conjugate is used to stain a sample that comprises a ligand for which the conjugated substance is a complementary member of a specific binding pair (e.g. Table 4).

Typically, the sample is obtained directly from a liquid source or as a wash from a solid material (organic or inorganic) or a growth medium in which cells have been introduced for culturing, or a buffer solution in which cells have been placed for evaluation. Where the sample comprises cells, the cells are optionally single cells, including microorganisms, or multiple cells associated with other cells in two or three dimensional layers, including multicellular organisms, embryos, tissues, biopsies, filaments, biofilms, etc.

Alternatively, the sample is a solid, optionally a smear or scrape or a retentate removed from a liquid or vapor by filtration. In one aspect of the invention, the sample is obtained from a biological fluid, including separated or unfiltered biological fluids such as urine, cerebrospinal fluid, blood, lymph fluids, tissue homogenate, interstitial fluid, cell extracts, mucus, saliva, sputum, stool, physiological secretions or other similar fluids. Alternatively, the sample is obtained from an environmental source such as soil, water, or air; or from an industrial source such as taken from a waste stream, a water source, a supply line, or a production lot.

In yet another embodiment, the sample is present on or in solid or semi-solid matrix. In one aspect of the invention, the matrix is a membrane. In another aspect, the matrix is an electrophoretic gel, such as is used for separating and characterizing nucleic acids or proteins, or is a blot prepared by transfer from an electrophoretic gel to a membrane. In another aspect, the matrix is a silicon chip or glass slide, and the analyte of interest has been immobilized on the chip or slide in an array (e.g. the sample comprises proteins or nucleic acid polymers in a microarray). In yet another aspect, the matrix is a microwell plate or microfluidic chip, and the sample is analyzed by automated methods, typically by various methods of high-throughput screening, such as drug screening.

The dye compounds of the invention are generally utilized by combining a dye compound of the invention as described above with the sample of interest under conditions selected to yield a detectable optical response. The term "dye compound" is used herein to refer to all aspects of the claimed dyes, including both reactive dyes and dye conjugates. The dye compound typically forms a covalent or non-covalent association or complex with an element of the sample, or is simply present within the bounds of the sample or portion of the sample. The sample is then illuminated at a wavelength selected to elicit the optical response. Typically, staining the sample is used to determine a specified characteristic of the sample by further comparing the optical response with a standard or expected response.

A detectable optical response means a change in, or occurrence of, an optical signal that is detectable either by observation or instrumentally. Typically the detectable response is a change in fluorescence, such as a change in the intensity, excitation or emission wavelength distribution of fluorescence, fluorescence lifetime, fluorescence polarization, or a combination thereof. The degree and/or location of staining, compared with a standard or expected response, indicates whether and to what degree the sample possesses a given characteristic. Some dyes of the invention may exhibit little fluorescence emission, but are still useful as chromophoric dyes. Such chromophores are useful as energy acceptors in FRET applications, or to simply impart the desired color to a sample or portion of a sample.

For biological applications, the dye compounds of the invention are typically used in an aqueous, mostly aqueous or aqueous-miscible solution prepared according to methods generally known in the art. The exact concentration of dye compound is dependent upon the experimental conditions and the desired results, but typically ranges from about one nanomolar to one millimolar or more. The optimal concentration is determined by systematic variation until satisfactory results with minimal background fluorescence are accomplished.

The dye compounds are most advantageously used to stain samples with biological components. The sample may comprise heterogeneous mixtures of components (including intact cells, cell extracts, bacteria, viruses, organelles, and mixtures thereof), or a single component or homogeneous group of components (e.g. natural or synthetic amino acid, nucleic acid or carbohydrate polymers, or lipid membrane complexes). These dyes are generally non-toxic to living cells and other biological components, within the concentrations of use.

The dye compound is combined with the sample in any way that facilitates contact between the dye compound and the sample components of interest. Typically, the dye compound or a solution containing the dye compound is simply added to the sample. Certain dyes of the invention, particularly those that are substituted by one or more sulfonic acid moieties, tend to be impermeant to membranes of biological cells, and once inside viable cells are typically well retained. Treatments that permeabilize the plasma membrane, such as electroporation, shock treatments or high extracellular ATP can be used to introduce selected dye compounds into cells. Alternatively, selected dye compounds can be physically inserted into cells, e.g. by pressure microinjection, scrape loading, patch clamp methods, or phagocytosis.

Dyes that incorporate an aliphatic amine or a hydrazine residue can be microinjected into cells, where they can be fixed in place by aldehyde fixatives such as formaldehyde or glutaraldehyde. This fixability makes such dyes useful for intracellular applications such as neuronal tracing.

Dye compounds that possess a lipophilic substituent, such as phospholipids, will non-covalently incorporate into lipid assemblies, e.g. for use as probes for membrane structure; or for incorporation in liposomes, lipoproteins, films, plastics, lipophilic microspheres or similar materials; or for tracing. Lipophilic dyes are useful as fluorescent probes of membrane structure.

Chemically reactive dye compounds will covalently attach to a corresponding functional group on a wide variety of materials, forming dye conjugates as described above. Using dye compounds to label reactive sites on the surface of cells, in cell membranes or in intracellular compartments such as organelles, or in the cell's cytoplasm, permits the determination of their presence or quantity, accessibility, or their spatial and temporal distribution in the sample. Photoreactive dyes can be used similarly to photolabel components of the outer membrane of biological cells or as photo-fixable polar tracers for cells.

Preferred compounds used for methods of the invention include those where $R_x$ is a carboxylic acid, an activated ester of a carboxylic acid, an amine, an azide, a hydrazide, a haloacetamide, an alkyl halide, an isothiocyanate, or a maleimide group; and those where $S_c$ is an antibody, a peptide, a lectin, a polysaccharide, a nucleotide, a nucleoside, an oligonucleotide, a nucleic acid polymer, an ion-complexing moiety, a lipid, or a non-biological organic polymer or polymeric microparticle, that is optionally bound to one or more additional fluorophores that are the same or different.

Optionally, the sample is washed after staining to remove residual, excess or unbound dye compound. The sample is optionally combined with one or more other solutions in the course of staining, including wash solutions, permeabilization and/or fixation solutions, and solutions containing additional detection reagents. An additional detection reagent typically produces a detectable response due to the presence of a specific cell component, intracellular substance, or cellular condition, according to methods generally known in the art. Where the additional detection reagent has, or yields a product with, spectral properties that differ from those of the subject dye compounds, multi-color applications are possible. This is particularly useful where the additional detection reagent is a dye or dye-conjugate of the present invention having spectral properties that are detectably distinct from those of the staining dye.

The compounds of the invention that are dye conjugates are used according to methods extensively known in the art; e.g. use of antibody conjugates in microscopy and immunofluorescent assays; and nucleotide or oligonucleotide conjugates for nucleic acid hybridization assays and nucleic acid sequencing (e.g., U.S. Pat. Nos. 5,332,666 to Prober, et al. (1994); 5,171,534 to Smith, et al. (1992); 4,997,928 to Hobbs (1991); and WO Appl. 94/05688 to Menchen, et al.; all incorporated by reference). Dye-conjugates of multiple independent dyes of the invention possess utility for multi-color applications.

At any time after or during staining, the sample is illuminated with a wavelength of light selected to give a detectable optical response, and observed with a means for detecting the optical response. Equipment that is useful for illuminating the dye compounds of the invention includes, but is not limited to, hand-held ultraviolet lamps, mercury arc lamps, xenon lamps, lasers and laser diodes. These illumination sources are optionally integrated into laser scanners, fluorescence microplate readers, standard or minifluorometers, or chromatographic detectors. Preferred embodiments of the invention are dyes that are be excitable at or near the wavelengths 633-636 nm, 647 nm, 660 nm, 680 nm and beyond 700 nm, as these regions closely match the output of relatively inexpensive excitation sources.

The optical response is optionally detected by visual inspection, or by use of any of the following devices: CCD cameras, video cameras, photographic film, laser-scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is examined using a flow cytometer, examination of the sample optionally includes sorting portions of the sample according to their fluorescence response.

Kits

One aspect of the instant invention is the formulation of kits that facilitate the practice of various assays using any of the dyes of the invention, as described above. The kits of the invention typically comprise a colored or fluorescent dye of the invention, either present as a chemically reactive label useful for preparing dye-conjugates, or present as a dye-conjugate where the conjugated substance is a specific binding pair member, or a nucleoside, nucleotide, oligonucleotide, nucleic acid polymer, peptide, or protein. The kit optionally further comprises one or more buffering agents, typically present as an aqueous solution. The kits of the invention optionally further comprise additional detection reagents, a purification medium for purifying the resulting labeled substance, luminescence standards, enzymes, enzyme inhibitors, organic solvent, or instructions for carrying out an assay of the invention.

Preferred kits of the invention include those that include a dye solution comprising a compound of the formula

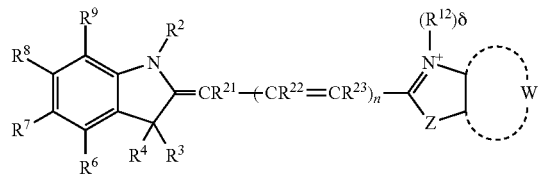

or its salts, wherein $R^3$ is -L-$R_x$; or -L-$S_c$; and $R^4$ is $C_1$-$C_6$ alkyl; and L is a covalent linkage that is linear or branched, cyclic or heterocyclic, saturated or unsaturated, having 1-16 nonhydrogen atoms selected from the group consisting of C, N, P, O, and S, and incorporating the formula —$(CH_2)_d$ $(CONH(CH_2)_e)_{z'}$—, where d is 0-5, e is 1-5 and z' is 0 or 1, such that the linkage contains any combination of ether, thio-ether, amine, ester, amide bonds; or single, double, triple or aromatic carbon-carbon bonds; or phosphorus-oxygen, phosphorus-sulfur, nitrogen-nitrogen, nitrogen-oxygen, or nitrogen-platinum bonds; or aromatic or heteroaromatic bonds; $R_x$ is a reactive group that is an activated ester of a carboxylic acid, an amine, a carboxylic acid, a halotriazine, a hydrazide, a maleimide, a reactive platinum complex; $S_c$ is a conjugated substance that is an antibody, an amino acid, an angiostatin or endostatin, an avidin or streptavidin, a biotin, a blood component protein, a dextran, an enzyme, an enzyme inhibitor, a hormone, an IgG-binding protein, a fluorescent protein, a growth factor, a lectin, a lipopolysaccharide, a metal-binding protein, a microorganism or portion thereof, a neuropeptide, a non-biological microparticle, a nucleotide, an oligonucleotide, a peptide toxin, a phospholipid-binding protein, a small-molecule drug, a structural protein, an NTA, or a tyramide; and $R^7$ is sulfo, and $R^6$, $R^8$, and $R^9$ are H; or $R^6$ and $R^7$ combine to form a fused benzo ring that is substituted one or more times by sulfo, and $R^8$ and $R^9$ are H; the atoms of W are selected from —CH, —C, —$CR^{1'}$, and —$N(R^{12})_{\beta'}$, where each $\beta'$ is 1, but no more than one of such atoms is —$N(R^{12})_{\beta'}$, where each $R^{1'}$ is sulfo or Br; $R^2$ and $R^{12}$ are independently a $C_1$-$C_6$ alkyl or $C_1$-$C_6$ alkyl substituted by sulfo; δ is 0 or 1, and δ+all δ'=1; and δ is 1 only when W contains no ring nitrogen atoms; $R^{13}$ and $R^{14}$ are independently $C_1$-$C_6$ alkyl; each of $R^{21}$, $R^{22}$, and $R^{23}$ are H; or any two adjacent substituents of $R^{21}$, $R^{22}$, $R^{23}$, when taken in combination, forms a 4-, 5-, or 6-membered saturated or unsaturated hydrocarbon ring that is optionally substituted one or more times by $C_1$-$C_6$ alkyl, halogen, or a carbonyl oxygen.

The examples below are given so as to illustrate the practice of this invention. They are not intended to limit or define the entire scope of this invention. See also, U.S. Patent application Ser. No. 60/236,637, filed Sep. 29, 2000, incorporated by reference; and U.S. Patent application Ser. No. 60/276,870, filed Mar. 16, 2001, incorporated by reference.

Example 1

Preparation of 3-(5-carboxypentyl)-2,3-dimethyl-5-sulfoindolium, inner salt (Compound 1)

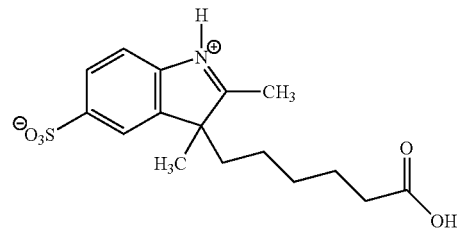

Compound 1

A mixture of 25 g of ethyl 2-methylacetoacetate, 64 mL of a 21% sodium ethoxide solution in ethanol and 34 mL of ethyl 6-bromohexanoate is refluxed in 200 mL of ethanol overnight. The mixture is filtered and solvent is evaporated. The residue is partitioned between 1 M HCl and chloroform. The organic layer is dried over magnesium sulfate and purified on silica gel using 1:10 ethyl acetate/hexanes as eluant to yield 22 g of ethyl 2-(5-carbethoxypentyl)-2-methylacetoacetate.

The acetoacetate thus obtained is dissolved in 300 mL of methanol. A solution of 10 g NaOH in 100 mL water is added. The mixture is heated at 50° C. overnight. The solution is reduced to ~50 mL, acidified to ~pH 1, and extracted with ethyl acetate. The organic layer is dried over $MgSO_4$ and evaporated to yield 13.5 g of 7-methyl-8-oxononanoic acid. The nonanoic acid is refluxed in 110 mL of acetic acid with 13.5 g of 4-hydrazinobenzenesulfonic acid for 5 hours. The acetic acid is evaporated and the product is purified on silica gel to yield 23 g of the product.

Example 2

Preparation of 2,3-dimethyl-3-(5-carboxypentyl)-5-sulfo-1-(3-sulfopropyl)indolium, sodium salt (Compound 2)

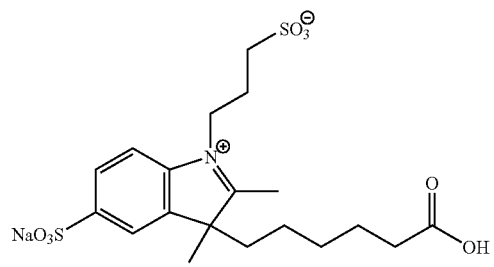

Compound 2

To a methanol solution of 11 g of Compound 1 is added 34 g of anhydrous sodium acetate. The mixture is stirred for five minutes. The solvent is evaporated. The resulting sodium salt is heated with 24.4 g of propanesultone at 110° C. for 1 hour to generate the product.

Example 3

Preparation of 5-sulfo-1-(3-sulfopropyl)-2,3,3-trimethylindolium, sodium salt (Compound 3A) and 5-sulfo-1-(3-sulfopropyl-1,2,3,3-tetramethylindolium, sodium salt (Compound 3B)

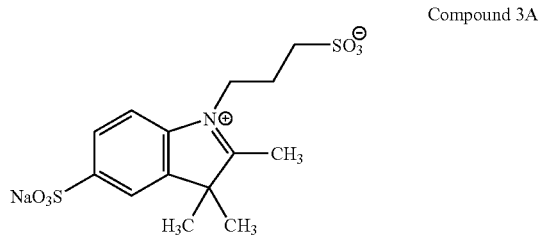
Compound 3A

To 15 g of 5-sulfo-2,3,3-trimethylindolium, inner salt (Mujumdar, et al BIOCONJUGATE CHEMISTRY 4, 105 (1993)) in 60 mL of methanol is added 5.67 g sodium acetate. After 5 minutes at room temperature, the solution is evaporated. The foamy solid is pulverized, dissolved in 60 mL acetonitrile and stirred with 23 g propanesultone for 15 min. Following evaporation of the solvent, the residue is dried at 110° C. to yield 5-sulfo-1-(3-sulfopropyl)-2,3,3-trimethylindolium, sodium salt (Compound 3A). 5-sulfo-1,2,3,3-tetramethylindolium (Compound 3B) is prepared similarly except that methyl p-toluenesulfonate is used instead of propanesultone.

Example 4

Preparation of 2-(4-anilinobutadienyl)-3,3-dimethyl-5-sulfo-1-(3-sulfopropyl)indolium, sodium salt (Compound 4)

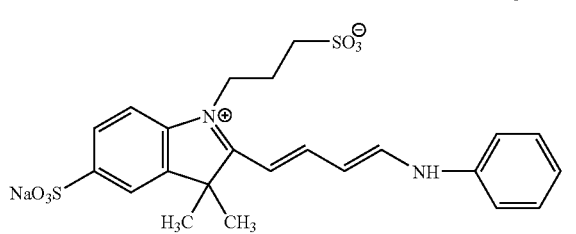
Compound 4

Compound 3A (15 g) is heated with 215 g malonaldehyde dianil hydrochloride and 0.4 mL triethylamine in 200 mL of acetic acid at 110° C. for one hour. The solvent is evaporated and the residue is purified on silica gel to yield 1.39 g of the product.

Example 5

Preparation of 2-(anilinovinyl)-3,3-dimethyl-5-sulfo-1-(3-sulfopropyl)indolium, sodium salt (Compound 5)

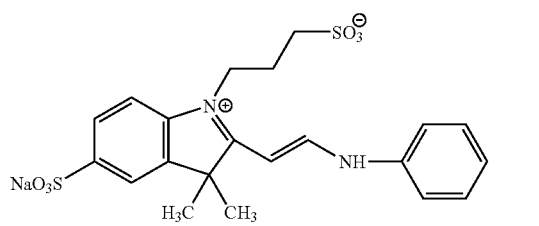
Compound 5

A mixture of 5 g of Compound 3A, 272 g of N,N'-diphenylformamidine and 0.52 mL of acetic anhydride is heated at 150° C. for 30 minutes, then evaporated and the residue purified on silica gel.

Example 6

Preparation of 2-(4-anilinobutadienyl)-5-sulfo-1,3,3-trimethylindolium, inner salt (Compound 6)

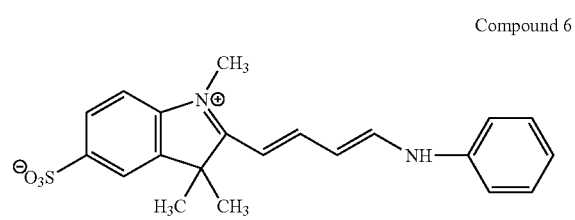
Compound 6

The procedure is the same as used to prepare Compound 4, except that Compound 3B is used instead of Compound 3A.

Example 7

Preparation of 3-(5-carboxypentyl)-5-sulfo-1,2,3-trimethylindolium, inner salt (Compound 7)

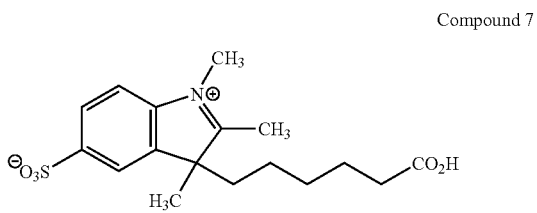
Compound 7

The compound is prepared by heating Compound 1 with 6 equivalents of methyl p-toluenesulfonate at 100° C. for 1.5 hours. The crude product is precipitated with ethyl acetate.

Example 8

Preparation of Compound 8

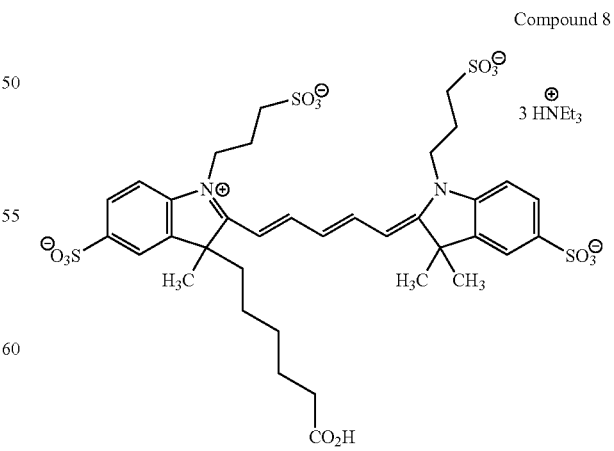
Compound 8

Compound 2 (1 g) and Compound 4 (15 g) are combined with 0.84 mL triethylamine and 0.5 mL acetic anhydride. The mixture is stirred at room temperature for 1 hour, then evaporated and the residue is purified by HPLC.

Example 9

Preparation of Compound 9

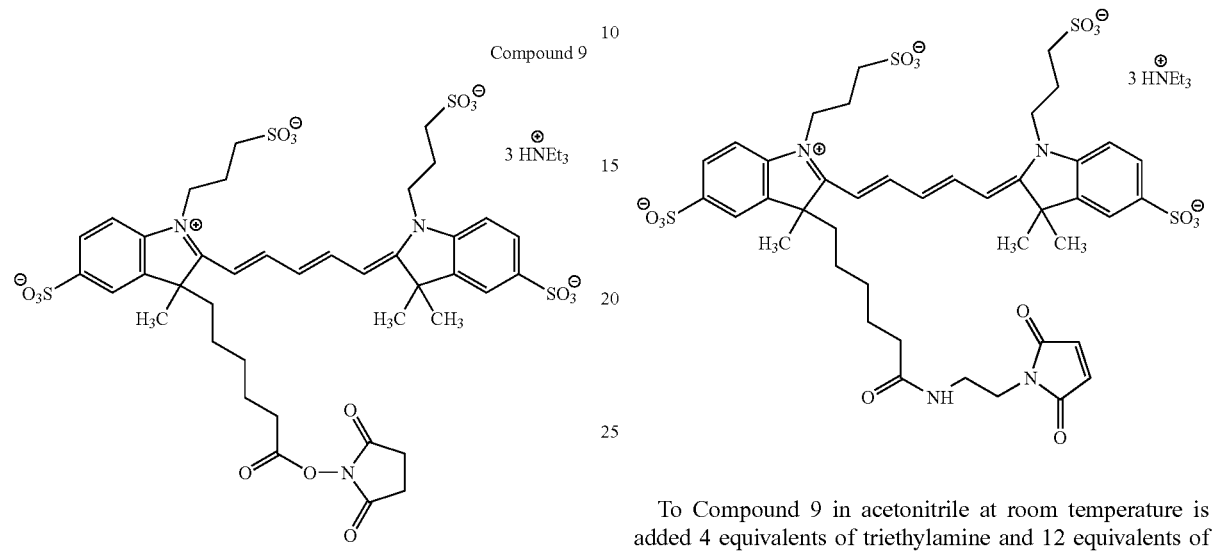

To 55 mg of Compound 8 in 1 mL of DMF is added 0034 mL of triethylamine and 21 mg of 2-succinimido-1,1,3,3-tetramethyluronium tetrafluoroborate. The mixture is stirred at room temperature for 30 minutes and evaporated to yield the succinimidyl ester.

Example 10

Preparation of Compound 10

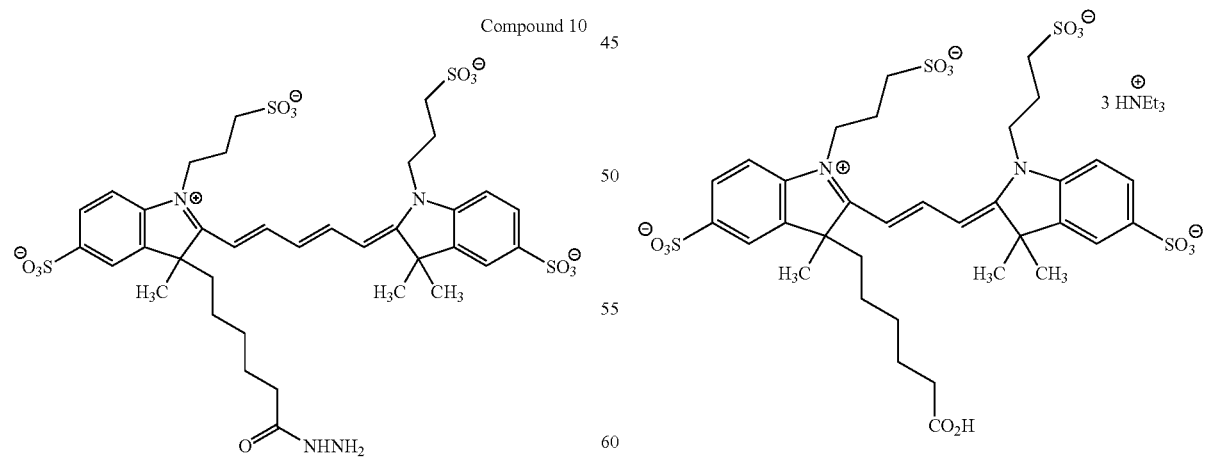

To Compound 9 in acetonitrile is added 3 equivalents of triethylamine and 12 equivalents anhydrous hydrazine. The mixture is stirred at ambient temperature for 15 minutes. The product is precipitated with 4 volumes of ethyl acetate and purified by HPLC.

Example 11

Preparation of Compound 11

To Compound 9 in acetonitrile at room temperature is added 4 equivalents of triethylamine and 12 equivalents of N-(2-aminoethyl)maleimide, trifluoroacetic acid salt. The mixture is stirred at ambient temperature for 15 minutes. The product is precipitated with 4 volumes of ethyl acetate and purified by HPLC.

Example 12

Preparation of Compound 12

To 6 mmole of Compound 2 is added 2 g of Compound 5 in 20 mL DMF, 42 mL triethylamine, and 1.8 mL of acetic anhydride. The reaction is stirred at room temperature for one hour, then evaporated and the residue is purified by HPLC.

Example 13

Preparation of Compound 13

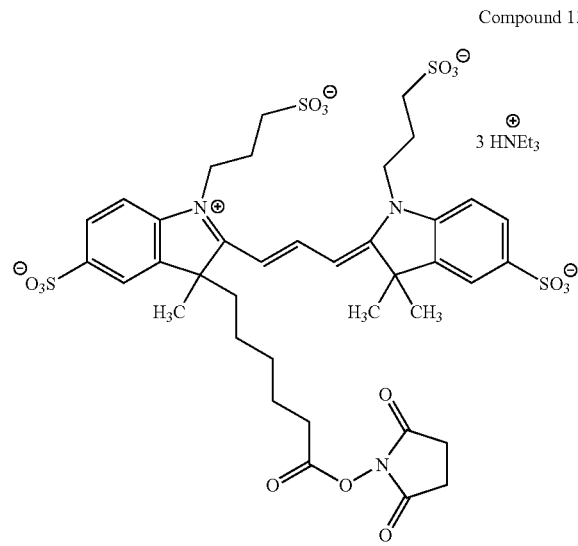

Compound 13

The procedure is similar to that used to prepare Compound 9, using Compound 12 in place of Compound 8

Example 14

Preparation of Compound 14

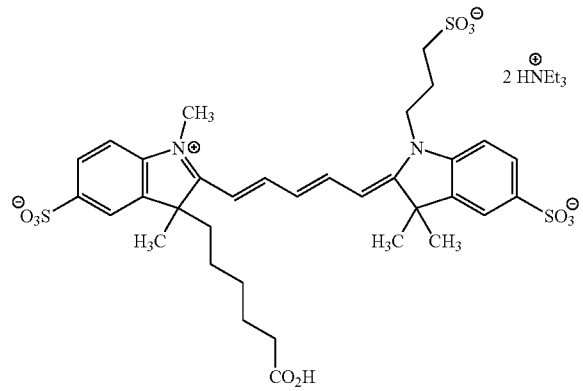

Compound 14

The compound is prepared in DMF by mixing one equivalent each of Compound 4 and Compound 7, followed by addition of four equivalents of triethylamine and 15 equivalents of acetic anhydride. After stirring at room temperature for 2 hours and evaporation, the residue is purified by HPLC.

Example 15

Preparation of Compound 15

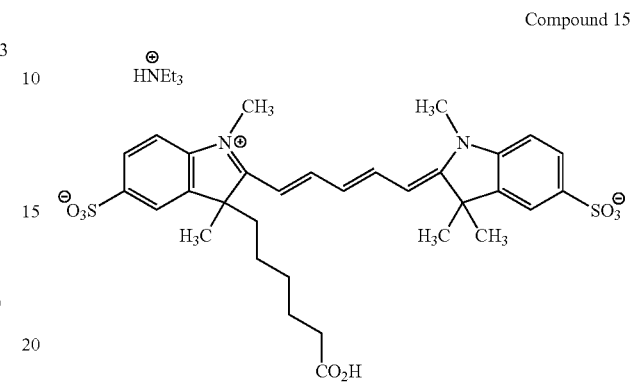

Compound 15

To a mixture of 0.27 g Compound 6 and 0.6 mmoles Compound 7 in 8 mL of DMF is added 0.42 mL triethylamine and 0.1 mL acetic anhydride. The mixture is stirred at room temperature for two hours then evaporated and the residue is purified by HPLC.

Example 16

Preparation of Compound 16

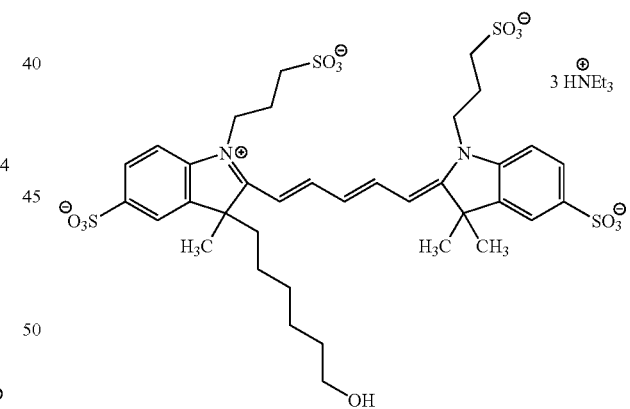

Compound 16

Ethyl 2-methylacetoacetate is alkylated with 6-benzoyloxy-1-bromohexane in the presence of 12 equivalents of sodium hydride in THF and the resulting product was hydrolyzed and decarboxylated in aqueous NaOH as in example 1 to generate the desired 9-hydroxy-3-methyl-2-nonanone. The nonanone is then heated at reflux with 1 equivalent of 4-hydrazinebenzenesulfonic acid in acetic acid to generate 3-(6-hydroxyhexyl)-2,3-dimethyl-5-sulfoindolium, inner salt. The hydroxy again is protected as an benzoyloxy group and this intermediate is then transformed to the protected form of target compound as in example 8. The benzoyl protecting group is then removed by dilute NaOH.

Example 17

Preparation of Compound 17

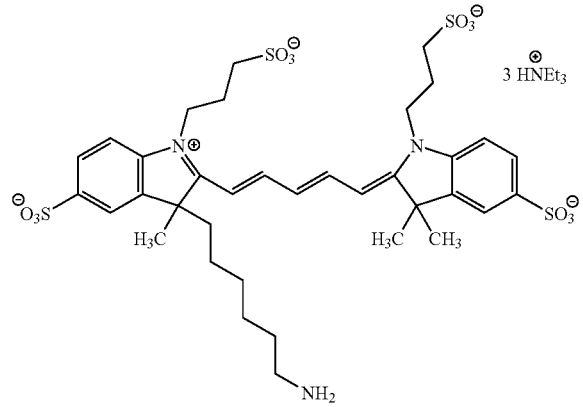

Compound 17

The intermediate is prepared as in Example 16, except that 6-t-butoxycarbonyloxy-1-bromohexane is used instead of 6-benzoyloxy-1-bromohexane The t-BOC protecting group is removed with trifluoroacetic acid at room temperature after formation of the target dye.

Example 18

Preparation of Compound 18

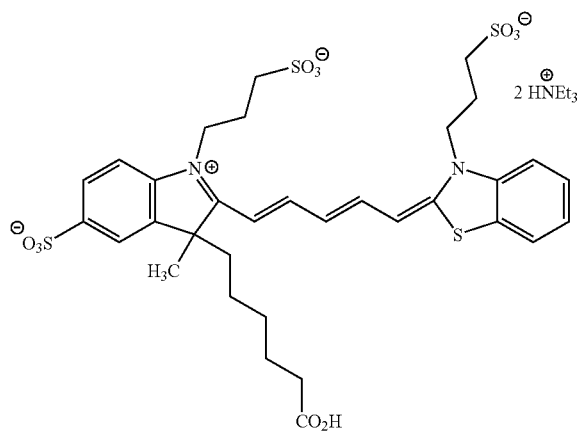

Compound 18

To 1 mmole 2-methyl-1-(3-sulfopropyl)-benzothiazolium, inner salt (from heating of one equivalent each of propanesultone and 2-methylbenzothiazole at 110° C. for one hour) and 150 mg of Compound 31 in 5 mL of DMF is added 0.28 mL of triethylamine and 0.1 mL acetic anhydride. The reaction is stirred at room temperature for one hour, then evaporated and the residue is purified by HPLC.

Example 19

Preparation of Compound 19

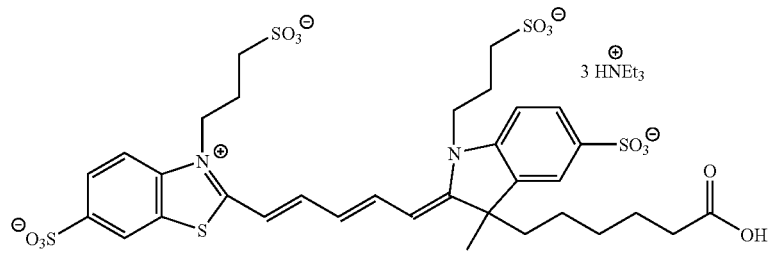

Compound 19

Compound 19 is prepared in the same manner as Compound 18 except starting with 2-methyl-6-sulfobenzothiazole, which is prepared by reaction of sulfuric acid and 2-methylbenzothiazole at room temperature.

Example 20

Synthesis of 2-(6-anilinohexatrienyl)-3,3-dimethyl-5-sulfo-1-(3-sulfopropylindolium), inner salt (Compound 20)

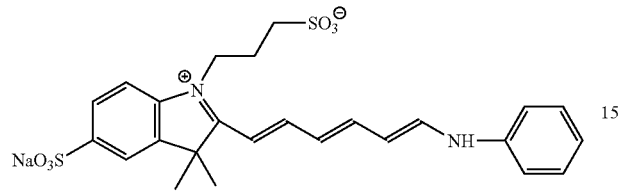

Compound 20

A mixture of 1.9 g of Compound 3A and 2.85 g of N-(5-anilino-2,4-pentadienylidene)aniline hydrochloride in 30 mL of acetic anhydride is heated at 120° C. for 30 minutes. At the end of the period, 90 mL of ethyl acetate is added and the product is filtered and used as is.

Example 21

Synthesis of Compound 21

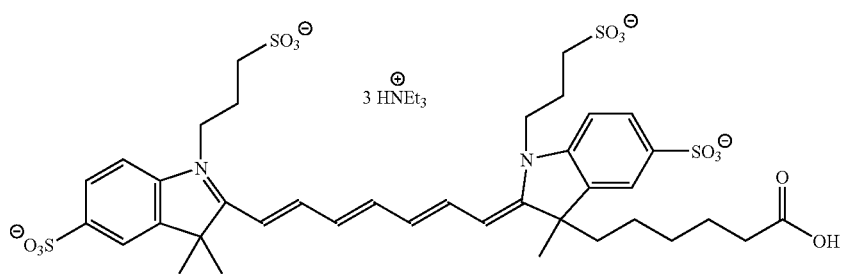

Compound 21

A mixture of 1.05 g of Compound 20, 2 mmoles of Compound 2, 10 mL of DMF, 1.7 mL of triethylamine and 0.6 mL of acetic anhydride is stirred at room temperature overnight and then at 35° C. for an additional 1.5 hour. 40 mL of ethyl acetate is added and the precipitate is purified by HPLC.

Example 22

Synthesis of Compound 22

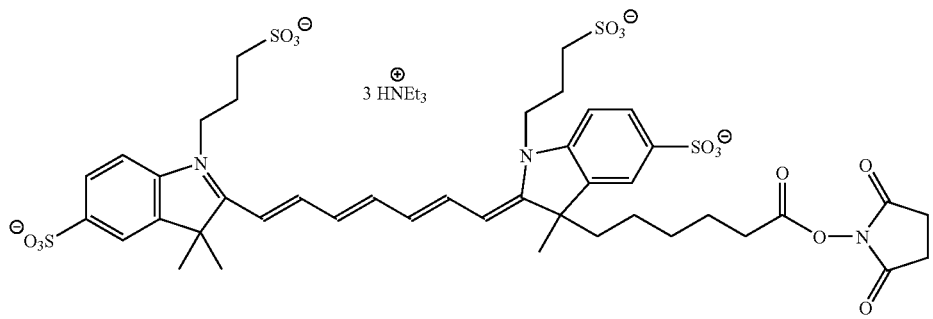

Compound 22

The succinimidyl ester of Compound 21 (Compound 22) is prepared as described in Example 9.

Example 23

Synthesis of Compound 23

Compound 23

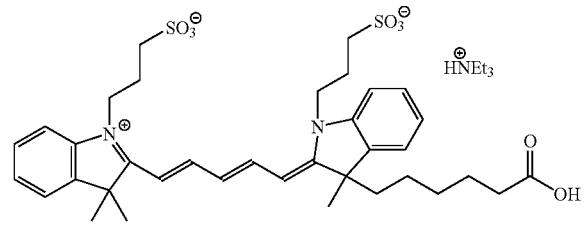

A mixture of 0.37 g of 2-(4-anilinobutadienyl)-3,3-dimethyl-1-(3-sulfopropyl)indolium (prepared by the reaction of trimethylindoline and propanesultone as in Example 3 followed by reaction with malonaldehyde dianil hydrochloride as in Example 4), 1.35 mmoles of 3-(5-carboxypentyl)-3-methyl-1-(3-sulfopropyl)indolium (prepared by the reaction of 7-methyl-8-oxononanoic acid and phenyl hydrazine, as in Example 1), 7 mL DMF, 0.42 mL triethylamine and 0.1 mL of acetic anhydride is stirred at room temperature for one hour. Ethyl acetate (30 mL) is added and the precipitate is purified on silica gel to yield 55 mg of Compound 23.

Example 24

Synthesis of Corresponding Activated Esters from Free Acids

The following activated esters are prepared from the corresponding free acids, according to the method in Example 9:

Compound 24, prepared from Compound 15

Compound 24

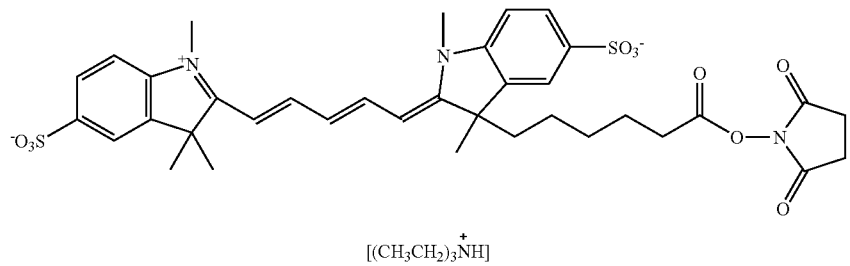

Compound 25, prepared from Compound 23

Compound 25

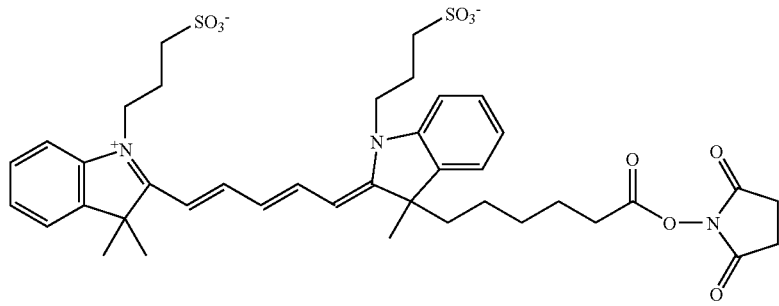

Compound 26, prepared from Compound 18

Compound 26

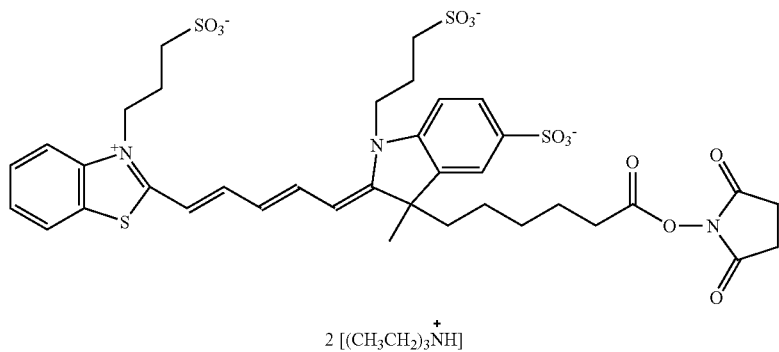

Compound 27, prepared from Compound 19

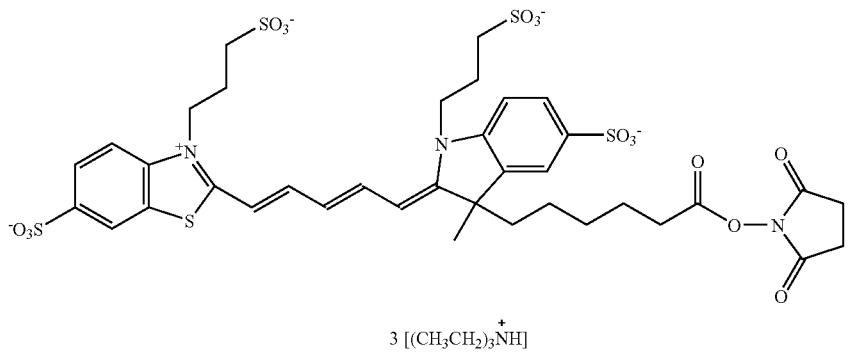
Compound 27

Example 25
Preparation of Compound 28

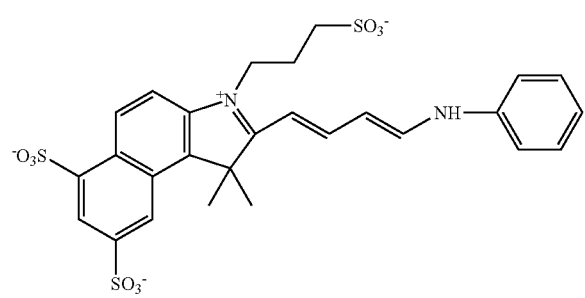
Compound 28

The compound is prepared by quarternization of 1,1,2 tri-methylbenzindoleninium 1,3-disulfonate (Bioconjugate Chem, 356-362 (1996)) with propanesultone and then heated with 2 equivalents of malonaldehyde dianil hydrochloride in acetic acid with catalytic amount of triethylamine to yield Compound 28.

Example 26
Preparation of Compound 29

The compound is prepared by stirring one equivalent each of Compound 28 and 3-(5-carboxypentyl)-2,3-dimethyl-5-sulfo-1-(3-sulfopropyl)-indoleninium inner salt, sodium salt in the presence of 3 equivalents of triethylamine and one equivalent of acetic anhydride in DMF at room temperature for one hour to yield Compound 29.

Compound 29 is optionally converted to its corresponding succinimidyl ester as described in Examples 9 and 24.

Example 27

Preparation of Compound 30

For purposes of comparison with dyes of the invention (See FIG. 4), Compound 30 is prepared according to BIOCONJUGATE CHEM. 4, 105-111 (1993).

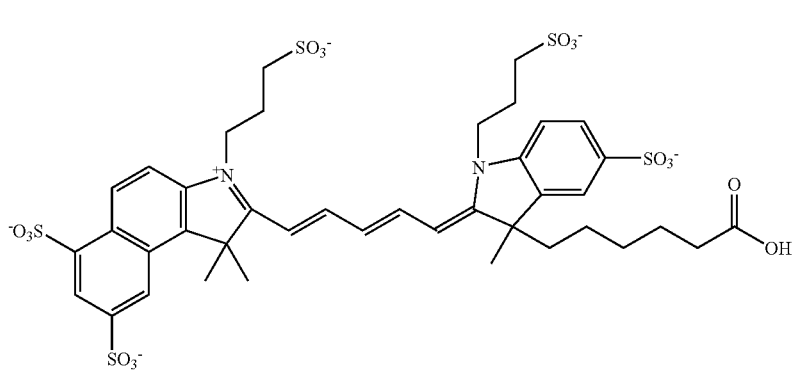
Compound 29

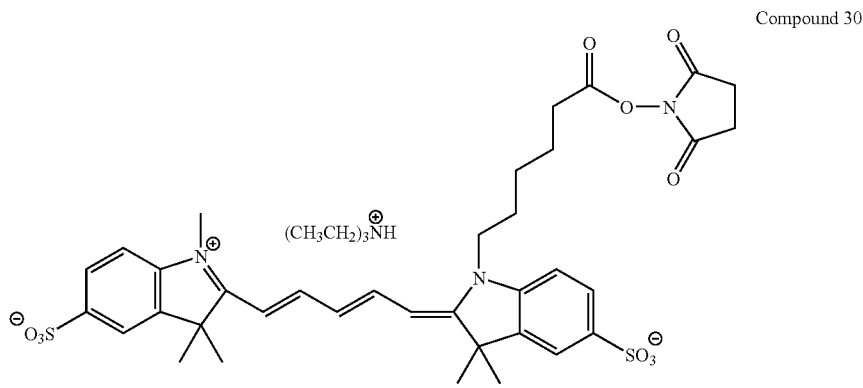

Compound 30

Example 28

Preparation of Compound 31

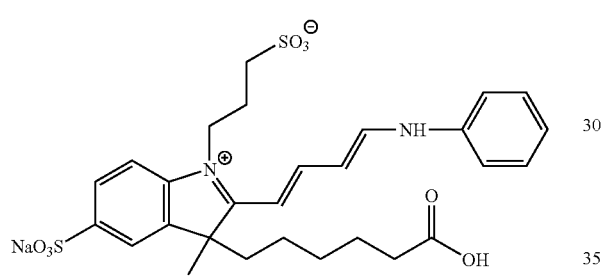

Compound 31

A mixture of 45 mmoles of Compound 2 and 23 g of malonaldehyde dianil hydrochloride is heated to reflux in 400 mL of acetic acid with 0.65 mL of triethylamine for 1 hour. The solvent is evaporated and the residue is purified on silica gel to yield 2.4 g of the product.

Example 29

Preparation of 2,4-dimethyloxazolo[415-b]pyridinium tosylate (Compound 41)

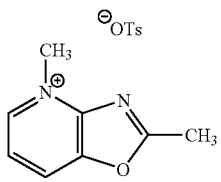

Compound 41

2-Amino-3-hydroxypyridine (1448 g) is triacetylated by heating with 3 equivalents of acetic anhydride at 120-130° C. for 4 hours to yield, after silica gel column purification, 10.3 g of 3-acetoxy-2,2-diacetylimidopyridine. This compound is heated for 2 days at 65° C. with 3 equivalents of methyl tosylate to yield 7 g of 3-acetoxy-1-methyl-2-acetimido-1,2-dihydropyridine, p-toluenesulfonic acid salt. The 2-methyloxazolo[4,5-b]pyridine is then generated in situ when this dihydropyridine is treated with triethylamine.

Example 30

Preparation of 2-methyl-4-(3-sulfopropyl)-oxazolo [4,5-b]pyridinium, inner salt (Compound 42)

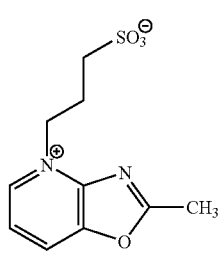

Compound 42

Compound 42 is prepared analogously to Compound 41 (Example 30), except that propanesultone is used rather than methyl tosylate.

Example 31

Preparation of Compounds 43-46

3-Methyl-2-methylthiooxazolopyridinium tosylate is prepared by heating the corresponding 2-methylthiooxazolopyridines (M. Y. Chu-Moyer and R. Berger, J. Org. Chem., 60, 5721-5725 (1995)) with one equivalent of methyl tosylate at 100-110° C. for one hour. Derivatives prepared similarly include:

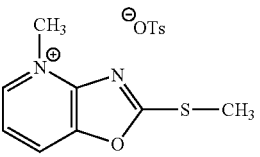

Compound 43

4-methyl-2-methylthiooxazolo[4,5-b]pyridinium tosylate

Compound 44

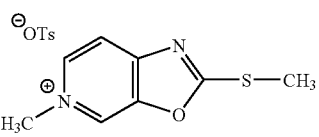

6-methyl-2-methyothiooxazolo[5,4-c]pyridinium tosylate

Compound 45

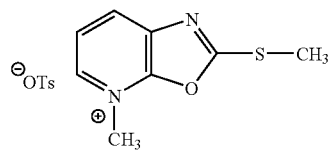

7-methyl-2-methylthiooxazolo[5,4-b]pyridinium tosylate

Compound 46

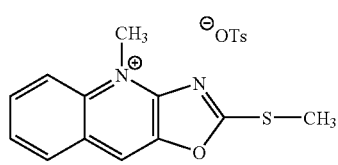

4-methyl-2-methylthiooxazolo[4,5-b]quinolinium tosylate

Example 32

Preparation of 2,4-dimethyl-5-methoxyoxazolo[4,5-b]quinolinium tosylate (Compound 47)

Compound 47

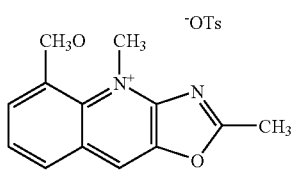

2-Amino-3-hydroxy-8-methoxyquinoline is prepared according to M. Y. Chu-Moyer (as above) starting from 2-amino-8-methoxyquinoline. This compound is treated with 3 equivalents of acetic anhydride in pyridine, and the reaction mixture is heated from room temperature to 120° C. and stirred overnight. The 2-methyl-5-methoxyoxazolo[4,5-b]quinoline thus generated is then heated with 3 equivalents of methyl tosylate at 70° C. for 8 hours to give the desired product.

Example 33

Preparation of 2,4-dimethyloxazolo[4,5-b]quinolinium tosylate (Compound 48)

Compound 48

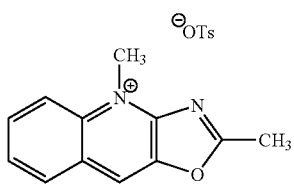

A mixture of 0.6 g of 2-amino-3-hydroxyquinoline, 3.8 mL of trimethylorthoacetate and 0.1 g of p-toluenesulfonic acid is heated at 60° C. for 7 hours. The reaction mixture is then diluted with ethyl acetate, washed with sodium bicarbonate, and purified by column chromatography on silica gel to yield 0.28 g of 2-methyloxazolo[4,5-b]quinoline. The quinoline is heated with one equivalent of methyl tosylate at 70° C. for one hour to generate the product.

Example 34

Preparation of 3-methyl-2-methylthiothiazolo[4,5-b]pyridinium tosylate (Compound 49)

Compound 49

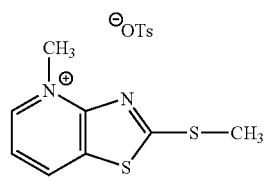

To 0.626 g of 2-methylthiothiazolo[4,5-b]pyridine (Smith, et al. SULFUR LETTERS, 17, 197-216 (1994)) is added 0.71 g of methyl tosylate and the mixture is heated at 120° C. for one hour. After cooling to room temperature, 10 mL of ethyl acetate is added and the mixture is stirred for 30 minutes. The supernatant liquid is decanted and the product is recovered as an oily layer.

Example 35

Preparation of 2,3,3,7-tetramethyl-3H-pyrrolo[2,3-b]pyridinium tosylate (Compound 50)

Compound 50

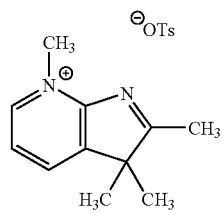

The compound is prepared according to a literature procedure (Ficken et al, J CHEM. SOC. 3202 (1949)).

Example 36

Preparation of 7-(3-sulfopropyl)-2,3,3-trimethyl-3H-pyrrolo[2,3-b]pyridinium, inner salt (Compound 51)

Compound 51

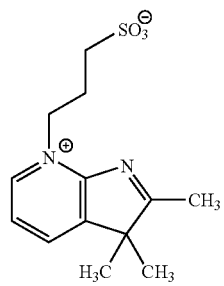

A mixture of 9 g of 2,3,3-trimethyl-3H-pyrrolo[2,3-b]pyridine and 20.6 g of propanesultone is heated at 60° C. for 3 hours. The reaction mixture is then dissolved in 100 mL of acetonitrile and 300 mL of ethyl acetate is added. The resulting sticky solid is again stirred in 300 mL of ethyl acetate to yield 22 g of the product.

Example 37

Preparation of 5-bromo-2,3,3-trimethyl-3H-pyrrolo[2,3-b]pyridine (Compound 52)

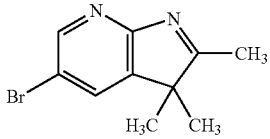

Compound 52

To 40 g of 2,5-dibromopyridine in 200 mL of 2-methoxyethanol is added 53 mL of anhydrous hydrazine and the mixture is heated at 110° C. for 3 hours to generate the 5-bromo-2-hydrazinopyridine. A mixture of 10 g of this hydrazinopyridine is heated at reflux overnight with 11 mL of 3-methyl-2-butanone in 40 mL of benzene equipped, using a condenser equipped with a Dean-Stark trap. All of the volatile components are removed under reduced pressure and the resulting residue is heated in 62 g of polyphosphoric acid at 140° C. for 45 minutes. The reaction mixture is poured into water, neutralized with sodium hydroxide and extracted with ethyl acetate. The resulting crude residue is purified by chromatography on silica gel, eluting with 1:1 ethyl acetate/hexanes, to yield 1.44 g of the product.

Example 38

Preparation of 5-bromo-7-(3-sulfopropyl)-2,3,3-trimethyl-3H-pyrrolo[2,3-b]pyridinium, inner salt (Compound 53)

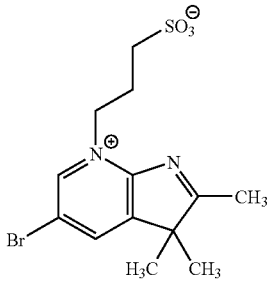

Compound 53

A mixture of 1 g of 5-bromo-2,3,3-trimethyl-3H-pyrrolo[2,3-b]pyridine and 1.54 g of propanesultone is heated at 65° C. for 2 hours. Ethyl acetate is added and the resulting mixture is stirred at room temperature overnight to yield 2.26 g of the product.

Example 39

Preparation of Compounds 54 and 55

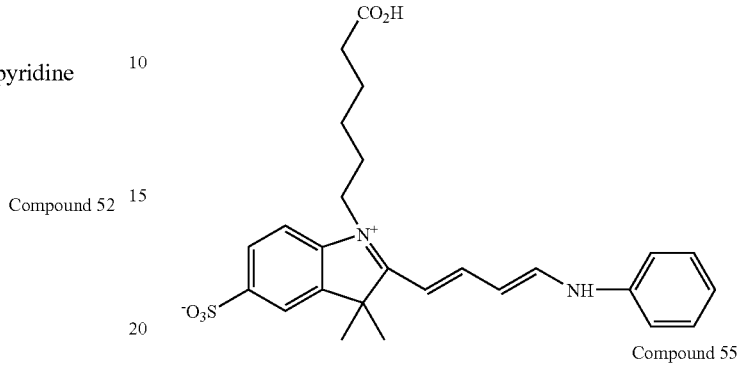

Compound 54

Compound 55

2-(4-Anilinobutadienyl)-1-(5-carboxypentyl)-3,3-dimethyl-5-sulfoindolinium, inner salt and 2-(4-anilinobutadienyl)-1-(3-sulfopropyl)-3,3-dimethyl-5-sulfoindolinium, potassium salt (Compounds 54 and 55, respectively) are prepared according to a literature procedure (Mujumdar, et al, BIOCONJUGATE CHEMISTRY 4, 105-111 (1993))

Example 40

Preparation of 2-(4-anilinobutadienyl)-3-carboxypentyl-benzothiazolium bromide (Compound 58)

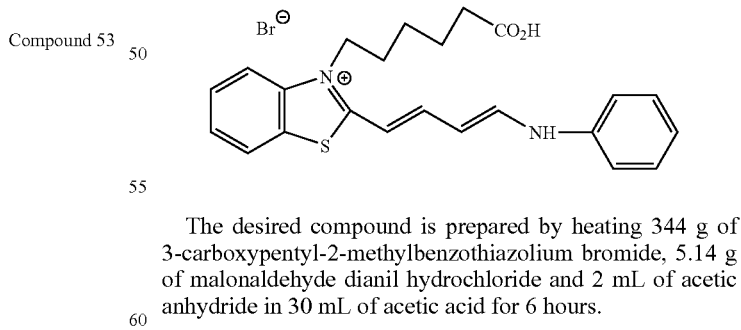

Compound 58

The desired compound is prepared by heating 344 g of 3-carboxypentyl-2-methylbenzothiazolium bromide, 5.14 g of malonaldehyde dianil hydrochloride and 2 mL of acetic anhydride in 30 mL of acetic acid for 6 hours.

Example 41

Preparation of Succinimidyl Esters of Carboxylic Acids

Succininimidyl ester derivatives are typically prepared from the corresponding carboxylic acids using the 2-succinimido-1,1,3,3-tetramethyl uronium tetrafluoroborate (Bannwarth et al. TETRAHEDRON LETT. 1157-1160 (1991)) and either triethylamine or diisopropylethylamine. Succinimidyl ester derivatives are also readily prepared by coupling a carboxylic acid derivative to N-hydroxysuccinimide using an activating agent such as a carbodiimide.

Example 42

Preparation of 7-(carboxypentyl)-2,3,3-trimethyl-3H-pyrrolo[2,3-b]pryridinium bromide (Compound 59)

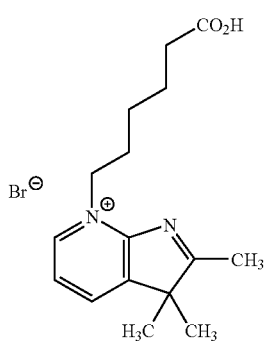

Compound 59

A mixture of 0.54 g of 2,3,3-trimethyl-3H-pyrrolo[2,3-b]pyridine and 1.32 g of 6-bromohexanoic acid is heated at 120° C. for one hour. Ethyl acetate (10 mL) is added, and the reaction mixture is heated at reflux for 15 minutes, then cooled to room temperature. The supernatant liquid is decanted to yield the product.

Example 43

Preparation of Compound 60

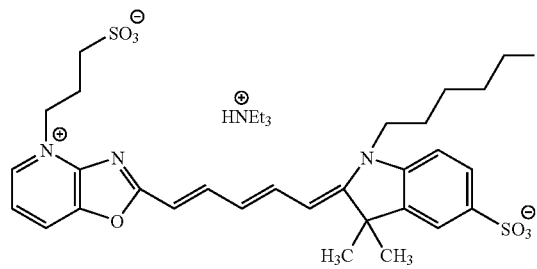

Compound 60

To one equivalent each of 2-methyl-4-(3-sulfopropyl)-oxazolo[4,5-b]pyridinium, inner salt (Compound 42) and 2-(4-anilinobutadienyl)-1-(5-carboxypentyl)-3,3-dimethyl-5-sulfoindolinium, inner salt (Compound 54) in DMF are added 4 equivalents of triethylamine and 2 equivalents of acetic anhydride. After stirring at room temperature for 2 hours, ethyl acetate is added to precipitate the crude product, which is purified by chromatography on silica gel.

Example 44

Preparation of Compound 61

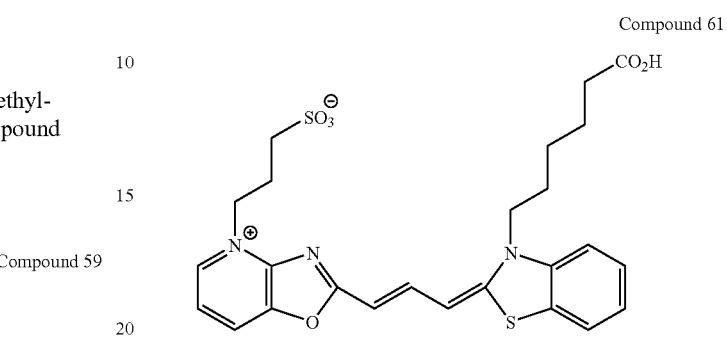

Compound 61

To 0.32 g of 3-acetoxy-2-acetimido-1-(sulfopropyl)-1,2-dihydropyridine, inner salt and 0.4 g of 2-(anilinovinyl)-3-(carboxypentyl)benzothiazolium tosylate in 5 mL of methylene chloride are added 0.14 g of triethylamine and 0.1 mL of acetic anhydride. The reaction mixture is stirred at room temperature for two hours. Ethyl acetate (8 mL) is added and the supernatant solution is decanted. The sticky residue is recrystallized from a mixture of DMF and ethyl acetate to yield the desired product.

Example 45

Preparation of Compound 62

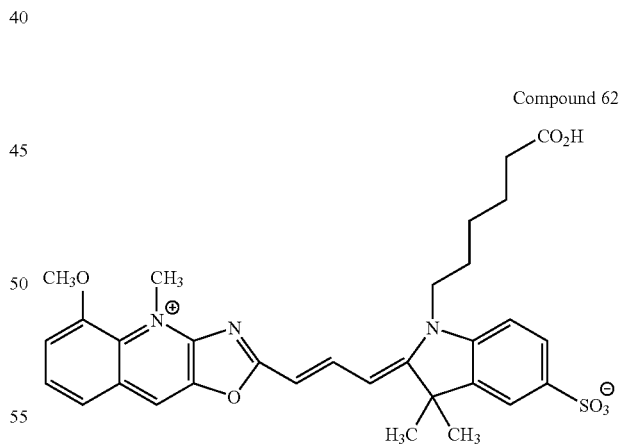

Compound 62

To a 005 mmole solution of 2,4-dimethyl-5-methoxyoxazolo[4,5-b]quinolinium tosylate in 2.5 mL of acetonitrile is added 20 mg of 2-(anilinovinyl)-3,3-dimethyl-1-(carboxypentyl)-5-sulfoindolenium iodide, 0.014 mL of triethylamine and 5 μL of acetic anhydride. The reaction mixture is heated at 60° C. overnight. The product is purified on a silica gel column.

Example 46

Preparation of Compound 63

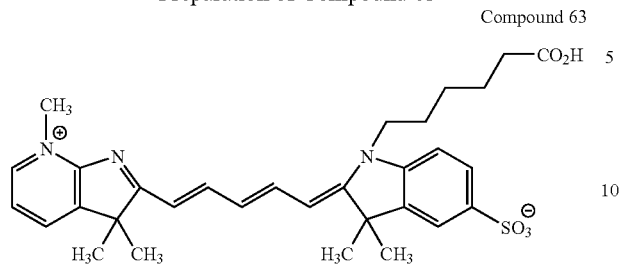

Compound 63

To 0.28 g of 2,3,3,7-tetramethyl-H-pyrrolo[2,3-b]pyridinium iodide and 0.3 g of 2-(4-anilinobutadienyl)-1-(5-carboxypentyl)-3,3-dimethyl-5-sulfoindolinium, inner salt in 3 mL of DMF at room temperature are added 0.2 mL of acetic anhydride and 0.42 mL of triethylamine. The reaction mixture is stirred at room temperature for 2 hours then the crude product is purified on a silica gel column.

Example 47

Preparation of Compound 64

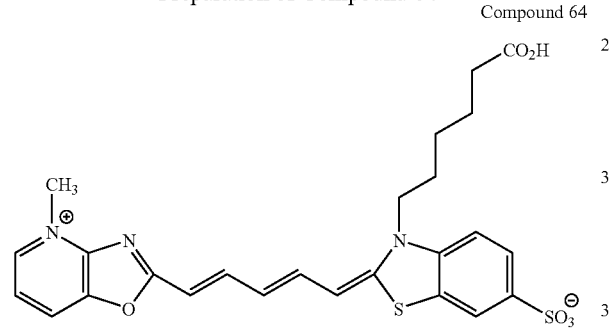

Compound 64

To an equivalent each of 3-acetoxy-1-methyl-2-acetimido-1,2-dihydropyridine, p-toluenesulfonic acid salt and 2-(4-anilinobutadienyl)-3-(5-carboxypentyl)-6-sulfobenzothiazolium, inner salt in DMF are added 3 equivalents of triethylamine and one equivalent of acetic anhydride to generate the desired product, which is chromatographically purified.

Example 48

Preparation of Compound 65

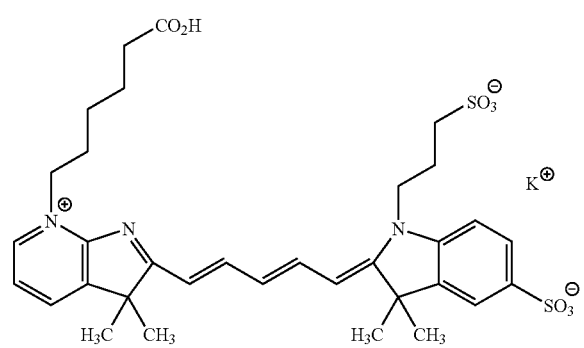

Compound 65

To a mixture of 0.35 g of 7-(carboxypentyl)-2,3,3-trimethyl-3H-pyrrolo[2,3-b]pyridinium bromide and 92 mg of 2-(4-anilinobutadienyl)-1-(3-sulfopropyl)-3,3-dimethyl-5-sulfoindolinium, potassium salt in 5 mL of DMF is added 0.28 mL of triethylamine and 0.06 mL of acetic anhydride. The mixture is stirred at room temperature for 1.5 hour. Ethyl acetate (20 mL) is added and the crude precipitate is purified on a silica gel column.

Example 49

Preparation of Compound 66 and Compound 67

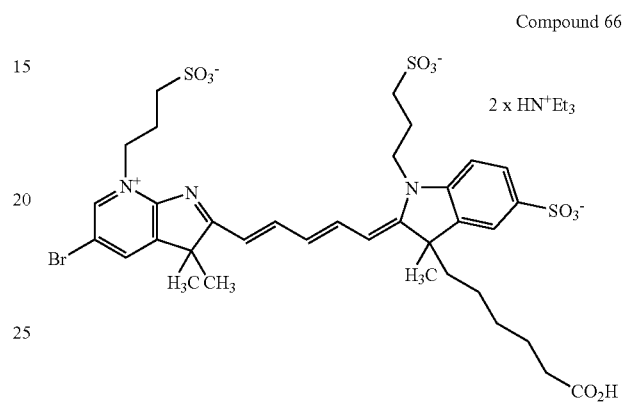

Compound 66

A mixture of 0.32 g of 2-(4-anilinobutadienyl)-3-carboxypentyl-3-methyl-5-sulfo-1-sulfopropylindolinium, sodium salt, 0.75 g of 5-bromo-7-(3-sulfopropyl)-2,3,3-trimethyl-3H-pyrrolo[2,3-b]pyridinium, inner salt, 0.36 mL of triethylamine and 0.1 mL of acetic anhydride is stirred in 13 mL of DMF at room temperature for 1 h. 50 mL of ethyl acetate is added then the crude solid is filtered and purified by HPLC. A succinimidyl ester derivative (Compound 67) is prepared according to the methods provided in Example 41.

Example 50

Preparation of Compound 68 and Compound 69

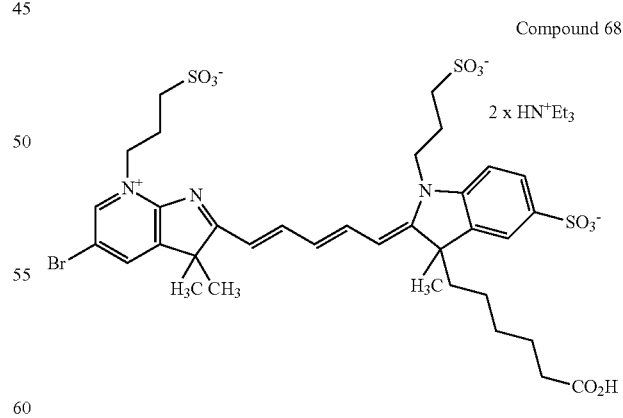

Compound 68

The compound is prepared in a similar manner as Compound 66 except that 7-(3-sulfopropyl)-2,3,3-trimethyl-3H-pyrrolo[2,3-b]pyridinium, inner salt is used. The crude product is purified by HPLC. A succinimidyl ester derivative (Compound 69) is prepared according to the methods provided in Example 41.

Example 51

Preparation of Compound 70 and Compound 71

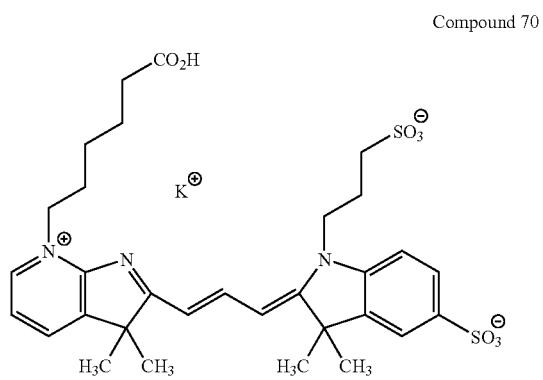

Compound 70

A mixture of 100 mg of 2-(anilinovinyl)-3,3-dimethyl-5-sulfo-1-sulfopropylindolenium, inner salt, potassium salt, 2 mmole of 7-(5-carboxypentyl)-2,3,3-trimethyl-3H-pyrrolo[2,3-b]pyridinium bromide, 5 mL of DMF, 0.2 mL of triethylamine and 0.12 mL of acetic anhydride is stirred at room temperature for 2 hours. At the end of the period, 20 mL of ethyl acetate is added and the crude precipitate is further purified on a silica gel column. The succinimidyl ester of this dye (Compound 71) is prepared as in Example 41.

Example 52

Preparation of Compound 72

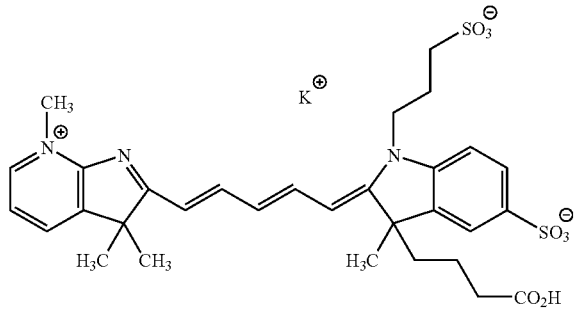

Compound 72

A mixture of 150 mg of 2-(anilinobutadienyl)-3-(3-carboxypropyl)-5-sulfo-1-sulfopropylindolenium, inner salt, potassium salt, 160 mg of 2,3,3,7-tetramethyl-3H-pyrrolo[2,3-b]pyridinium tosylate, 2 mL of DMF, 0.13 mL of triethylamine and 0.08 mL of acetic anhydride is heated at 40° C. for 30 minutes. Volatile components are evaporated and the crude residue is purified on a silica gel column.

Example 53

Preparation of Compound 73 and Compound 74

Compound 73

A solution of 32 g of 7-(3-sulfopropyl)-2,3,3-trimethyl-3H-pyrrolo[2,3-b]pyridinium, inner salt and 4 g of 2-(4-anilinobutadienyl)-1-(5-carboxypentyl)-3,3-dimethyl-5-sulfoindolinium, inner salt in 40 mL of DMF, 3.4 mL of triethylamine and 2 mL of acetic anhydride is stirred at room temperature for 4 hours. At the end of the period, 700 mL of acetonitrile is added and the crude solid is recovered by filtration and purified by HPLC. The succinimidyl ester derivative (Compound 74) is generated by the methods provided in Example 41.

Example 54

Preparation of Compound 75

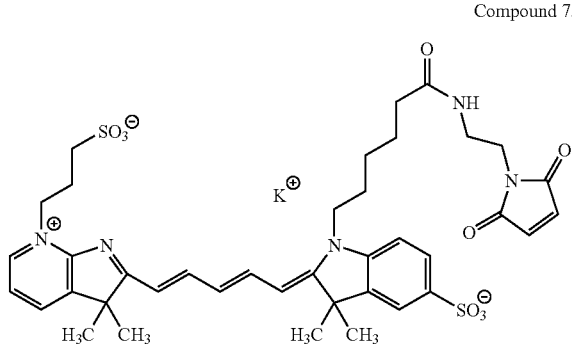

Compound 75

To a mixture of 30 mg of the succinimidyl ester Compound 74 (Example 53) and 10 mg of N-(2-aminoethyl)maleimde, trifluoroacetic acid salt in 2 mL of acetonitrile is added 0.015 mL of triethylamine is added and the mixture stirred at room temperature for 30 minutes. Then 6 mL of ethyl acetate is added and the solid filtered to yield the product.

Example 55

Preparation of Compound 76 and Compound 77

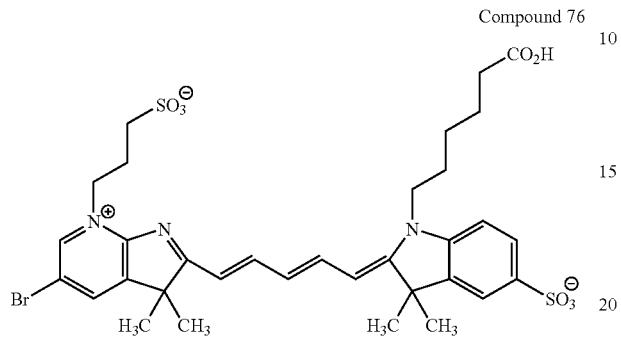

Compound 76

To 5 g of 5-bromo-7-(3-sulfopropyl)-2,3,3-trimethyl-3H-pyrrolo[2,3-b]pyridinium, inner salt and 25 g of 2-(4-anilinobutadienyl)-1-(5-carboxypentyl)-3,3-dimethyl-5-sulfoindolinium, inner salt in 20 mL of DMF at room temperature are added 5.8 mL of triethylamine and 3.5 mL of acetic anhydride. The reaction mixture is stirred at room temperature for 5 hours. At the end of the period, 140 mL of ethyl acetate is added, and the crude solid is collected by filtration and then purified by HPLC. The succinimidyl ester derivative (Compound 77) is generated by the methods provided in Example 41.

Example 56

Preparation of Compound 78

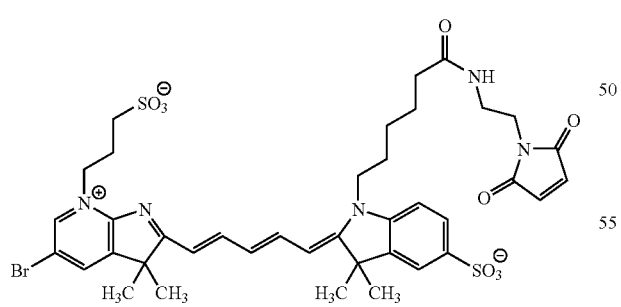

Compound 78

A mixture of 60 mg of the succinimidyl ester Compound 77 (Example 55) and 18 mg of N-(2-aminoethyl)maleimide, trifluoroacetic acid in 2 mL of acetonitrile at room temperature and 0.027 mL of triethylamine is stirred at ambient temperature for 30 minutes. Then 6 mL of ethyl acetate is added and the product is collected by filtration.

Example 57

Preparation of Compound 79

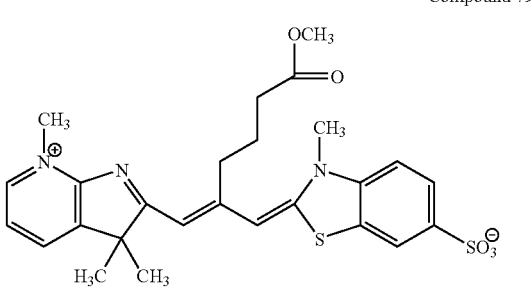

Compound 79

To 1.7 g of 2,3-dimethyl-6-sulfobenzothiazolium tosylate in 20 mL of pyridine at room temperature is added 1.03 mL of methyl 5-chloro-5-oxovalerate. The mixture is heated at 50-60° C. for 3 hours. The pyridine solvent is removed under reduced pressure, and the reaction is worked up with chloroform and brine, and purified by silica gel column to yield 0.92 g of 2-(5-methoxycarbonyl-2-oxopentylidene)-3-methyl-3H-benzothiazole. A mixture of 0.45 g of this benzothiazole and 0.45 g of phosphorous oxychloride in 5 mL of dichloroethane is heated at reflux for 2 hours to generate 2-(2-chloro-2-methoxycarbonylpropylvinyl)-3-methylbenzothiazolium chloride. The volatile components are evaporated and the crude chloride is used without further purification. The crude chloride and 0.45 g of 2,3,3,7-tetramethyl-3H-pyrrolo[2,3-b]pyridinium tosylate is stirred in 5 mL of dichloroethane in the presence of 0.45 mL of triethylamine for 2 hours. The volatile components are removed under reduced pressure, and the residue is dissolved in 5 mL of methanol and added dropwise to a solution of 4.5 g of sodium iodide in 30 mL water. The sticky solid is purified on a silica gel column to yield Compound 79.

Example 58

Preparation of Compound 80

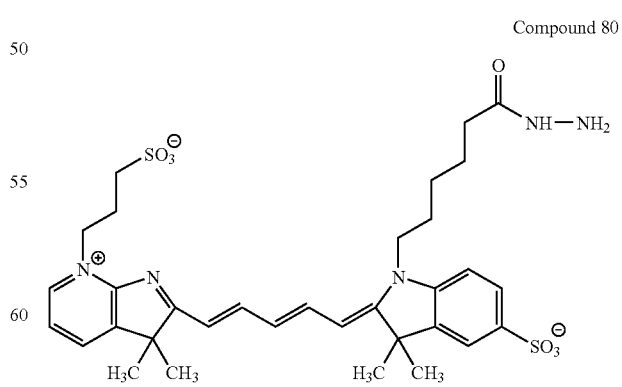

Compound 80

To 30 mg of the succinimidyl ester Compound 74 (Example 53) in 3 mL of acetonitrile, 001 mL of triethylamine and 107 mg of anhydrous hydrazine are added. The reaction mixture is stirred for 15 minutes then 12 mL of ethyl acetate is added to precipitate the product.

Example 59

Preparation of Compound 81

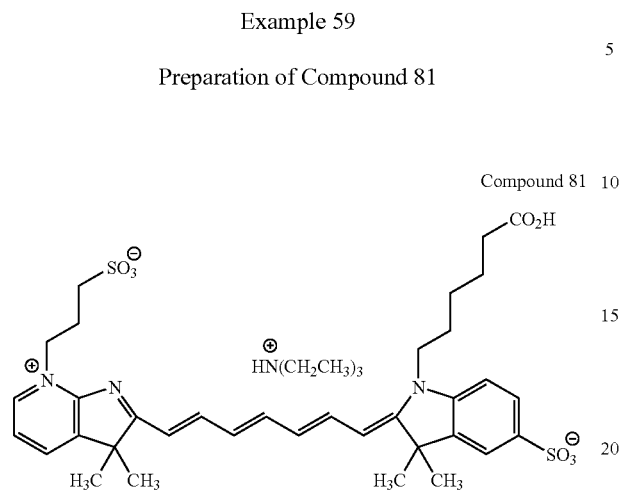

Compound 81

The intermediate 2-(6-anilinohexatrienyl)-1-5-(5-carboxypentyl)-3,3-dimethyl-5-sulfoindolinium, inner salt is prepared according to literature procedure (Licha et al. TET. LETT., 1711-1715 (2000)). To 0.1 g of 7-(3-sulfopropyl)-2,3,3-trimethyl-3H-pyrrolo[2,3-b]pyridinium, inner salt and 1 equivalent of 2-(6-anilinohexatrienyl)-1-5-(5-carboxypentyl)-3,3-dimethyl-5-sulfoindolinium, inner salt in 3 mL of DMF, 0.2 mL of triethylamine and 2 equivalents of acetic anhydride are introduced. The mixture is stirred at room temperature overnight and 30 mL of ethyl acetate is then added to precipitate the crude product. Purification by column chromatography on silica gel produces the pure product (Ex/Em (MeOH) 750 nm/800 nm, quantum yield=0.12).

Example 60

Preparation of Compound 82 and Compound 86

6-Hydrazinonaphthalene 1,3-disulfonate (Bioconj Chem., 356-362 (1996)) is heated with 7-methyl-8-oxononanoic acid in acetic acid to generate the 1-carboxypentyl-1,2-dimethyl-6,8-disulfobenzindoline. The benzindoline is quarternized with propane sultone and chain elongated with malonaldehyde dianil hydrochloride to yield the 2-(4-anilinobutadienyl) derivative (Compound 82) which is then reacted with compound 53 in the presence of acetic anhydride and triethylamine to yield the desired product.

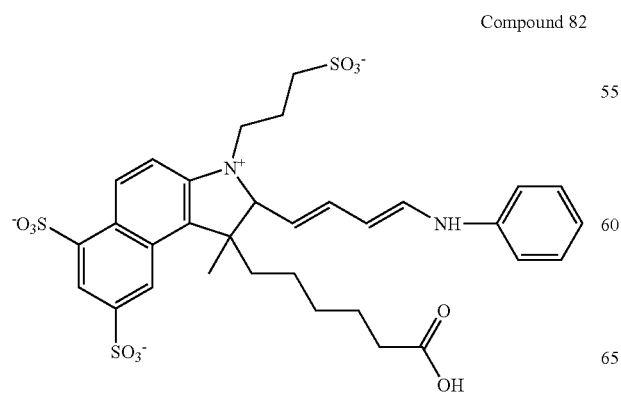

Compound 82

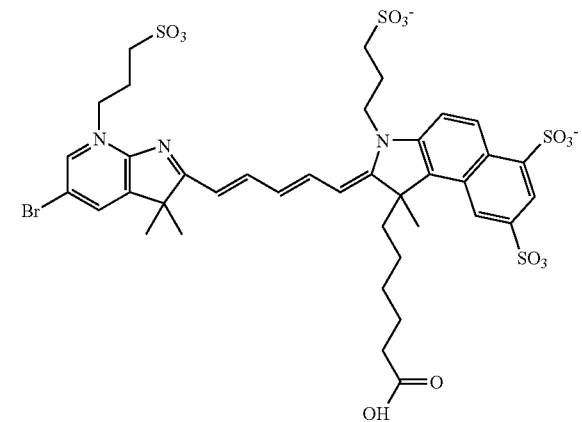

Compound 86

Example 61

Preparation of Compound 83

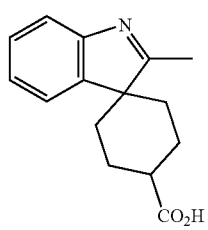

Compound 83

A mixture of 100 mg of 4-acetylcyclohexanecarboxylic acid and 120 mg of hydrazinobenzenesulfonic acid is refluxed in 5 mL of acetic acid to obtain the desired compound.

Example 62

Preparation of Compound 84

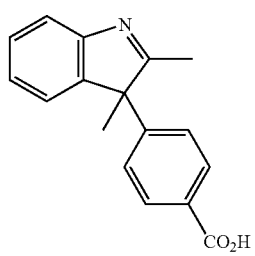

Compound 84

A mixture of 2-(4-carboxyphenyl)-butan-2-one and hydrazinobenzenesulfonic acid in acetic acid is refluxed for 3 hours to obtain the desired product.

Example 63

Preparation of Compound 85

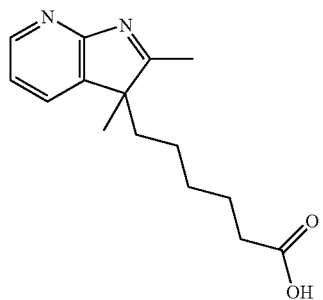

Compound 85

A mixture of 0.85 g of 2-hydrazinopyridine and 1.6 g of 7-methyl-8-oxononanoic acid is refluxed in 10 mL of benzene overnight. The volatile components are evaporated and the residue is heated with 0.2 g of zinc chloride at 250° C. for one hour to obtain the desired product.

Example 64

Preparation of a Phalloidin Dye-Conjugate

To aminophalloidin p-toluenesulfonate (35 mg, 4 μmol) and the succinimidyl ester derivative Compound 9 or 69 (6.0 mg, 5 μmol) in DMF is added N,N-diisopropylethylamine (2 μL, 11 μmol). The mixture is stirred at room temperature for 3 hours. To this solution is added 7 mL of diethyl ether. The solid is collected by centrifugation. The crude product is purified on SEPHADEX LH-20, eluting with water, followed by preparative HPLC to give the pure phalloidin conjugate. The product is an effective stain for F-actin filaments in fixed-cell preparations.

Example 65

Preparation of a Drug Dye-Conjugate

A fluorescent dopamine $D_2$ antagonist is prepared as follows: To 10 mg of N-(p-aminophenethyl)spiperone (Amlalky et al, FEBS LETT 176, 436 (1984)), and 10 μL N,N-diisopropylethylamine in 1 mL of DMF is added 15 mg of Compound 24 or 69. After 3 hours, the reaction mixture is poured into 5 mL ether. The precipitate is centrifuged, then purified by chromatography on silica gel using 10-30% methanol in chloroform.

Example 66

Preparation of Protein Dye-Conjugates

A series of dye conjugates of goat anti-mouse IgG (GAM), goat anti-rabbit IgG (GAR), streptavidin, transferrin and other proteins, including Conconavalin A, R-phycoerythrin (R-PE) and allophycocyanin (APC) are prepared by standard means (Haugland et al., METH. MOL. BIOL. 45, 205 (1995); Haugland, METH. MOL. BIOL. 45, 223 (1995); Haugland, METH. MOL. BIOL. 45, 235 (1995); Haugland, CURRENT PROTOCOLS IN CELL BIOLOGY 16.5.1-16.5.22 (2000)) using Compound 9 or 74 and a mono-succinimidyl ester derivative of the Cy5 dye (Amersham-Pharmacia Biotech).

The typical method for protein conjugation with succinimidyl esters of the invention is as follows. Variations in ratios of dye to protein, protein concentration, time, temperature, buffer composition and other variables that are well known in the art are possible that still yield useful conjugates. A solution of the protein is prepared at ~10 mg/mL in 0.1 M sodium bicarbonate. The labeling reagents are dissolved in a suitable solvent such as DMF at ~10 mg/mL. Water is a suitable solvent for many dyes of the invention. Predetermined amounts of the labeling reagents are added to the protein solutions with stirring. A molar ratio of 10 equivalents of dye to 1 equivalent of protein is typical, though the optimal amount varies with the particular labeling reagent, the protein being labeled and the protein's concentration, and is determined empirically.

When optimizing the fluorescence yield and determining the effect of degree of substitution (DOS) on this brightness, it is typical to vary the ratio of reactive dye to protein over a several-fold range. The reaction mixture is incubated at room temperature for one hour or on ice for several hours. The dye-protein conjugate is typically separated from free unreacted reagent by size-exclusion chromatography, such as on BIO-RAD P-30 resin equilibrated with phosphate-buffered saline (PBS). The initial, protein-containing colored band is collected and the degree of substitution is determined from the absorbance at the absorbance maximum of each fluorophore, using the extinction coefficient of the free fluorophore. The dye-protein conjugate thus obtained can be subfractionated to yield conjugates with higher, lower or more uniform DOS.

A solution of the desired protein is prepared at 10 mg/mL in 0.1 M sodium bicarbonate. The labeling reagents are dissolved in DMF at 10 mg/mL. Predetermined amounts of the labeling reagents are added to the protein solutions with stirring. A molar ratio of 10 equivalents of dye to 1 equivalent of protein is typical, though the optimal amount varies with the particular labeling reagent, the protein being labeled and the protein's concentration, and is determined empirically. The reaction mixture is incubated at room temperature for one hour, or on ice for several hours. The dye-protein conjugate is typically separated from free unreacted reagent by size-exclusion chromatography on BIO-RAD P-30 resin equilibrated with PBS. The initial, protein-containing colored band is collected and the degree of substitution is determined from the absorbance at the absorbance maximum of each fluorophore, using the extinction coefficient of the free fluorophore.

TABLE 5

| Fluorescence of Protein Conjugates of Compound 69 | | |
|---|---|---|
| Protein | DOS* | Quantum Yield† |
| Goat anti-Mouse IgG | 3.7 | 0.47 |
| Streptavidin | 4.5 | 0.85 |
| Wheat Germ Agglutinin | 3.1 | 0.32 |
| Goat anti-Rabbit IgG (highly cross-absorbed) | 4.4 | 0.5 |
| Goat anti-Chicken IgG | 4.5 | 0.33 |
| Rabbit anti-Mouse IgG | 3.0 | 0.67 |
| Goat anti-Mouse IgG (highly cross-absorbed | 4.4 | 0.63 |
| Goat anti-Guinea Pig IgG | 5.1 | 0.33 |
| Protein A (MR = 4)‡ | 2.1 | 0.64 |
| Protein A (MR = 8)‡ | 4.9 | 0.39 |

*Extinction coefficients are determined for the free carboxylic acid in aqueous solution
†Quantum yield measured relative to DDAO (7-hydroxy-9H-(1,3-dichloro-9,9-dimethylacridine-2-one)
‡MR is the approximate molar ratio of the dye to protein following conjugation

TABLE 6

Fluorescence of Protein Conjugates of Compound 67

| Protein | DOS* | Quantum Yield |
|---|---|---|
| Goat anti-Mouse IgG | 5.9 | 0.15 |
| Streptavidin | 4.8 | 0.66 |
| Goat anti-Rabbit IgG (highly cross-absorbed) | 4.9 | 0.26 |
| Goat anti-Chicken IgG | — | — |
| Rabbit anti-Mouse IgG | 6.0 | 0.31 |

*Extinction coefficients are determined for the free carboxylic acid in aqueous solution Protein conjugates of antibody fragments, of other avidins and of other proteins are prepared and analyzed similarly.

Example 67

Fluorescent Labeling of Periodate-Oxidized Proteins

Two samples of 5 mg each of goat IgG antibody in 1 mL of 0.1 M acetate, 0.135 M NaCl, pH 5.5, are treated with 2.1 mg of sodium metaperiodate on ice, for 1 and 2 hours, respectively. The reactions are stopped by addition of 30 µL ethylene glycol. The antibodies are purified on a MATREX GH 25 column (1 cm×30 cm) packed in PBS pH 7.2. One-tenth volume of 1 M sodium bicarbonate is added to raise the pH and Compound 17 or 80 is added at a molar ratio of dye to protein of 50:1. The reaction is stirred for 2 hours at room temperature. Sodium cyanoborohydride is added to a final concentration of 10 mM and the reaction is stirred for 4 hours at room temperature. The antibody conjugates are purified by dialysis and on CELLUFINE MATREX GH 25 columns as described above. Antibodies that are oxidized for 1 hour typically yield a degree of substitution of 1 mole of dye per mole of IgG. Antibodies that are oxidized for 2 hours typically yield a DOS of approximately 2 mole of dye per mole of IgG. Periodate-oxidized proteins in gels and on blots can also be labeled, essentially as described in Estep T. N. and Miller T J., (*Anal Biochem* 157, 100-105 (1986))

Example 68

Total Fluorescence of Selected Dye-Protein Conjugates as a Function of Degree of Substitution (DOS)

The conjugates of Compound 9 exhibit equal or greater fluorescence than the conjugates of Cy5 dye at similar DOS when conjugated to a wide variety of proteins (Table 3). Protein conjugates are prepared (as described in Example 66) at varying DOS and compared for brightness (total-fluorescence, TF) and relative quantum yield (RQY; definition at bottom of Table 3). Total fluorescence is proportional to the overall brightness of the bioconjugate, and is defined as the product of the RQY and DOS: TF=RQY X DOS.

Example 69

Total Fluorescence of Selected Dye-Protein Conjugates as a Function of Degree of Substitution Table 3 confirms the report of Gruber et al (BIOCONJUGATE CHEM. 11, 696 (2000)) of heavy quenching of the fluorescence of Cy5 conjugates (at even moderate DOS). For instance, comparing GAM IgG Compound 9 at ~DOS 4.2 with a GAM IgG Cy5 at DOS ~4.8 (see Table 3), reveal that the Compound 9 bioconjugate is approximately 5.0/0.4 brighter (12.5×) than the Cy5 bioconjugate. This type of pattern is observed for all of the proteins in Table 3. In general, the higher the DOS, the brighter Compound 9 bioconjugates are relative to the Cy5 bioconjugates, although, as can be seen, the Compound 9 bioconjugates are brighter at all DOS tested.

The decrease in the RQY of the Cy5 bioconjugates is found to be accompanied by an increase in the 600-nm absorbance band relative to the 650-nm absorbance band. This effect is true for all of the bioconjugates listed in Table 3. FIG. 2 shows a direct comparison of the absorption and fluorescence emission of the Compound 9 and Cy5 conjugate of GAM IgG at nearly equivalent DOS (Compound 9-GAM DOS ~4.2, Cy5-GAM DOS ~4.8). The 600 nm absorbance band is always much lower in extinction for Compound 9 than for an equivalently labeled Cy5 derivative. One can clearly see the increase in 600 nm absorbance for the Cy5 bioconjugate relative to the Compound 9 bioconjugate (FIG. 2) for all of the bioconjugates tested (Table 3). The increase in extinction of the 600 nm band is always associated with a large quenching of the fluorescence. This result is completely supportive of the work of Gruber et. al. (BIOCONJUGATE CHEM. 11, 696 (2000) who observed a similar correlation of an increased absorbance at 600 nm and a large decrease in fluorescence intensity. This general observation has now been confirmed with several other proteins (Table 3).

Figure 3:
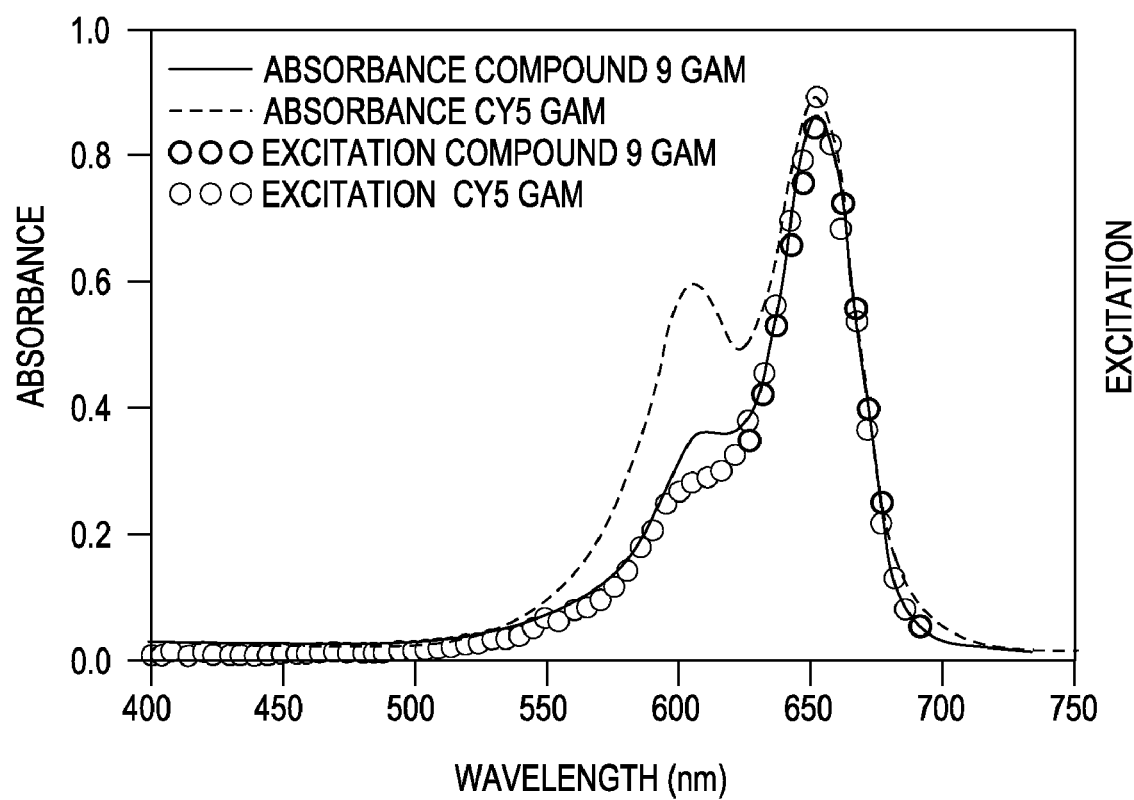
FIG. 3. Comparison of the absorption/excitation spectra of Compound 9 GAM and Cy5 derivatized GAM. Excitation spectra (emission wavelength=725 nm) normalized to absorbance spectra at 660 nm (see Example 69).

The Cy5 and Compound 9 derivatives of GAM (from FIG. 2) are examined using both absorbance spectroscopy and fluorescence excitation spectroscopy (FIG. 3). The fluorescence excitation spectra (emission wavelength=725 nm) of each derivative is normalized to its absorbance spectra at 660 nm. Dramatically clear in this figure is how the Cy5 GAM 600 nm absorbance band does not emit fluorescence, as evidenced by the large difference between the excitation and absorbance in this region of the spectrum. These data support the work of Gruber et al. (BIOCONJUGATE CHEM. 11, 696 (2000)), who saw similar changes in absorbance for Cy5 derivatized antibodies. The absorbance and excitation spectra of Compound 9 nearly overlap in this region. When this same Cy5-GAM antibody is dissolved in 6.0 M guanidinium hydrochloride (pH=7.5), the 600 nm absorbance band greatly decreases, the 650 nm absorbance band increases, and the overall fluorescence intensity increases dramatically. This result indicates that it is the behavior of the Cy5 derivative on the bioconjugate native structure, that causes the large decrease in fluorescence. A similar result was obtained for Cy5 derivatives of nuclease-digested DNA (Example 94, FIG. 13). Compound 9 bioconjugates have absorbance and excitation spectra that are much more closely aligned (e.g., FIG. 3), and hence show a drastically reduced amount of fluorescence quenching.

Example 70

Comparison of Two Structural "Cy5-Like" Isomers (Compound 30 and Compound 24), which Reveal the Origin of the Shift in Extinction from the 650 nm to 600 nm Bands on Bioconjugates of Cy5

In order to better understand the origin of the anomalous absorption effects of Cy5 bioconjugates and the much smaller effect with Compound 9, two isomers of Cy5 were synthesized and conjugated to GAR at various DOS (Compound 30 and Compound 24). FIG. 4 is a direct comparison of absorbance properties of these two isomers at DOS's of approximately 2.8, 4.3, and 5.5 on GAR. The only difference between the chemical structures of Compounds 30 and 24 is the change in position of the reactive moiety from position 1 (Cy5 position) to position 3 (shared by all dyes of the invention) of the indolium ring. One can see that this chemical change has resulted in a drastic improvement of the behavior of the absorbance of Compound 24 over Compound 30. Compound 24 has a brighter fluorescence emission than Compound 30 at all of these tested DOS's (Table 3).

Example 71

Comparison of the Total Fluorescence of GAM Conjugates of Compound 9 with Commercially Available Conjugates of the Cy5 Dye Conjugates of the Cy5 dye with GAM were purchased from several sources (Table 3) Absorption spectra of each of these conjugates confirm the general observations made in FIGS. 2 and 3, in that the Cy5 GAM conjugates all had much larger absorbances at 600 nm (relative to the 650 nm band) than the corresponding Compound 9-GAM conjugates. For fluorescence brightness comparisons, the proteins are adjusted to approximately the same concentration as measured by the absorption at 280 nm corrected for the contribution of dye absorption at 280 nm. For some commercial Cy5 bioconjugates, the protein concentration supplied by the vendor was utilized due to the presence of 280 nm-absorbing stabilizers. The conjugates are excited at 633 nm and the fluorescence emission spectrum measured. The results in Table 3 confirm the superior fluorescence brightness (TF) of GAM conjugates of Compound 9 compared with the commercially available Cy5 conjugates of GAM.

Example 72

Comparison of the Total Fluorescence of GAM Conjugates of Compound 9 with Commercially Available Conjugates of the Cy5 Dye with GAM Using Flow Cytometry The fluorescence intensity comparisons from Examples 68 and 69 confirm spectroscopically the greater fluorescence emission of bioconjugates of Compound 9 compared with the comparable Cy5 bioconjugates. The fluorescence intensity comparisons described in this example, reveal that the increased brightness is also apparent in experiments performed on a flow cytometer. The flow cytometer intensity comparisons do not rely on the same type of RQY, DOS, and TF calculations required for the spectroscopically based fluorescence intensity comparisons.

Human peripheral blood is drawn in a sodium heparin tube. One hundred μL of blood is added to a Falcon tube. The blood is blocked with 5 μL of mouse monoclonal antibodies to both human CD16 and CD32 (Caltag) for 15 minutes at room temperature. The cells are washed with PBS and resuspended to 100 μL. The blood is then incubated with mouse monoclonal antibody to mouse anti-CD3 (Caltag) at the recommended concentration of 0.50 μg for 30 minutes at 37 degrees Celsius. After incubation with the primary antibody, the cells are washed and resuspended. The blood is then incubated with GAM conjugates of Compound 9 (prepared as in Example 66) and the commercial GAM conjugates of Cy5 from Jackson Laboratories (DOS ~1.9) and Amersham-Pharmacia (DOS ~11) at a concentration of 0.50 μg for 30 minutes at 37 degrees Celsius. The red blood cells are lysed with a cell lysis buffer and centrifuged to remove the lysed red blood cells. The cell pellet is washed once with PBS and resuspended to a final volume of 500 μL. The samples are analyzed on a FACScan flow cytometer (BD Biosciences) exciting with a 488 nm argon-ion laser and a long-pass (>650 nm) filter. A direct comparison of GAM conjugates of Compound 9 with the commercially available labeled GAM conjugates of Cy5 is shown in FIG. 5. The geometric mean of the background subtracted fluorescence intensity for the Compound 9 conjugates of GAM is 164, whereas the Cy5-GAM conjugates prepared by Jackson Laboratories and Amersham-Pharmacia are 71, and 30, respectively.

Flow cytometry studies are performed as a function of DOS for this antibody, and it is found that at all DOS's, the conjugate of Compound 9 with GAM is from 1.4× to 5.9× brighter than the commercially available Cy5 conjugates of GAM (see Table 7). The flow cytometric results support the conclusion from the spectroscopic characterizations (Examples 68 and 69) that Compound 9 bioconjugates are brighter than the corresponding Cy5 bioconjugates.

TABLE 7

| DOS | (Compound 9 GAM)/ (Amersham Cy5 GAM)† | (Compound 9 GAM)/ (Jackson Cy5 GAM)‡ |
|---|---|---|
| 1.83 | 4.84 | 1.92 |
| 2.36 | 5.7 | 2.26 |
| 3.94 | 5.8 | 2.26 |
| 4.36 | 5.86 | 2.33 |
| 7.25 | 3.6 | 1.4 |

†, ‡, The geometric mean of the background subtracted fluorescence intensities obtained from Compound 9-labeled GAM divided by the intensity of Amersham-Pharmacia Biotech (†) or the Jackson Laboratories (‡) Cy5 version of this same antibody.

Example 73

Comparison of the Fluorescence of Goat Anti-Rabbit IgG (GAR) Conjugates of Compound 13 and Those of the Spectrally Similar Cy3 Dye GAR is labeled with Compound 13 and the CY3 reactive dyes at a variety of degrees of substitution ranging from 1.0-12. In all cases, the GAR conjugates of Compound 13 are superior in brightness to the Cy3 dye-labeled GAR (at equivalent DOS). A typical example is shown in FIG. 6 (DOS ~6.3). Excitation wavelength=532 nm.

Example 74

The Photostability of Compound 9 is Greater than that of Cy5 Reactive Dye

Figure 7:
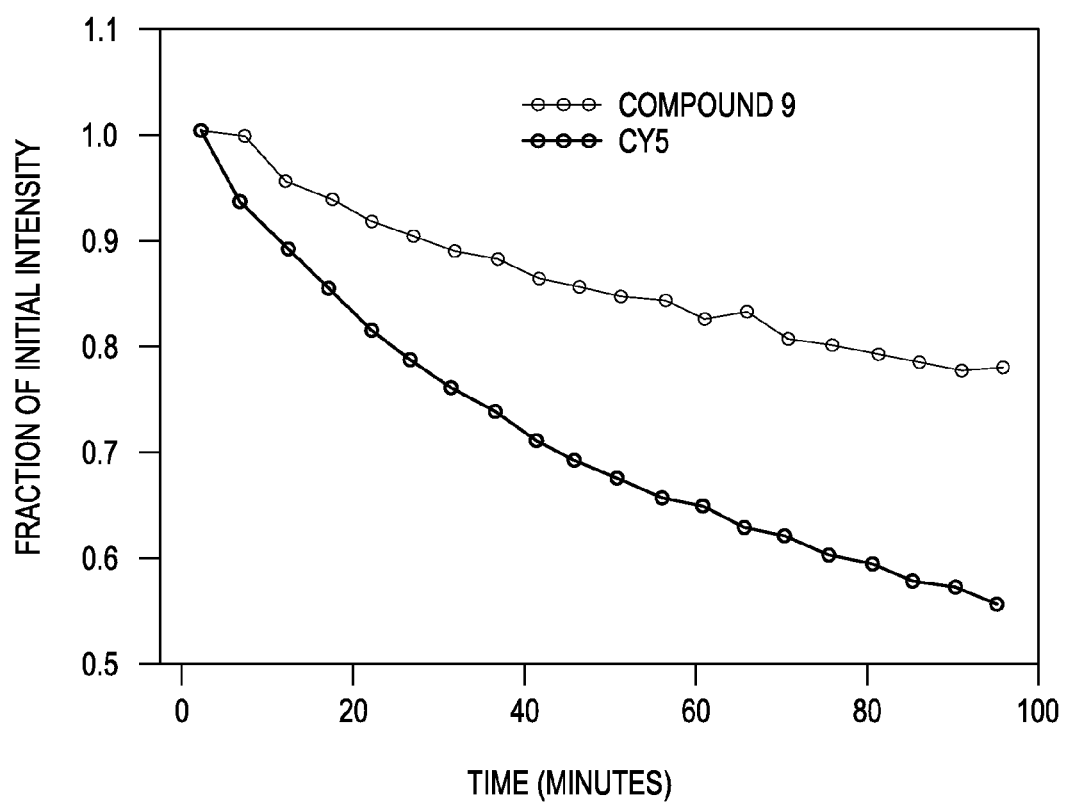
FIG. 7. Photostability comparison of Compound 9 (solid circles) with Cy5 (open circles), (40× objective, pH=7.5 solution) (see Example 74).

Photobleaching experiments are performed in small capillary tubes at 05 μM concentrations of Compound 9 and commercially available Cy5 reactive succinimidyl esters, in PBS, pH 7.5. The 40× objective of a Nikon Eclipse E-400 and Cy3/Cy5 filter XF92 (Omega) with a 100 W Mercury lamp excitation, is utilized. Integrated intensities are collected under constant illumination as a function of time (FIG. 7). After 100 minutes of illumination, Compound 9 remains about 2× brighter than the Cy5 dye.

Example 75

Labeling β-Galactosidase with a Thiol-Reactive Dye

A solution of β-galactosidase, a protein rich in free thiol groups, is prepared in PBS (20 mg in 400 μL). The protein solution is then treated with a 20 mg/mL solution of the maleimide derivative Compound 11 in DMF. Unreacted dye is removed on a spin column. The degree of substitution by the dye is estimated using the extinction coefficient of the free dye. The protein concentration is estimated from the absorbance at 280 nm, corrected for the absorbance of Compound 11 at that wavelength.

Example 76

Fluorescence Energy Transfer in Conjugates of R-Phycoerythrin and Allophycocyanin An R-phycoerythrin (R-PE) conjugate of Compound 9 or 74 is prepared as in Example 66 with a DOS sufficiently high to quench the donor fluorescence almost completely (DOS ~4-8). The resulting phycobiliprotein conjugate is excited at 488 nm and the fluorescence emission is compared to that of unmodified R-phycoerythrin excited at the same wavelength. Highly efficient energy transfer (>99%) occurs from the protein to the fluorescent dye (FIG. 8).

Compound 22 conjugated to R-PE with a DOS of 4.7, 8.2, and 13, generates energy-transfer efficiencies of ~90%, ~99%, and ~99.3%, respectively. A conjugate of these complexes with streptavidin is prepared essentially as described by Haugland (METH. MOL. BIOL. 45, 205 (1995), supra). This streptavidin conjugate retains the energy transfer properties and is useful for cell staining in flow cytometers that utilize the argon-ion laser for excitation.

Tandem conjugates of allophycocyanin can also be made, with longer wavelength dyes of the invention such as Compound 22. These conjugates yield emission well beyond 700 nm when excited near 633 nm (FIG. 9).

Example 77

Staining Cells with Tandem Dye-Labeled Streptavidin

Human peripheral blood is drawn in a sodium heparin tube and treated exactly as described in Example 72, except in this case, a biotinylated anti-CD3 antibody (Caltag) is utilized as the primary step, and tandem-dye conjugates of Compound 9-derivatized streptavidin-R-PE and the commercial Cy5 version of this product (Gibco Red 670) are utilized for detection in parallel experiments. The samples are analyzed on a FACScan flow cytometer (BD Biosciences) exciting with a 488 nm argon-ion laser and a long-pass (>650 nm) filter. A direct comparison of the tandem streptavidin-R-PE conjugate of Compound 9 with the commercially available tandem dye-labeled streptavidin-R-PE reveals that the signal-to-noise ratio of the tandem conjugate prepared from Compound 9 is ~4.5× brighter than the corresponding Cy5 tandem conjugate (FIG. 10).

Example 78

Labeling and Use of a Wheat Germ Agglutinin Dye-Conjugate

Wheat germ agglutinin (100 mg, EY Laboratories) is dissolved in 5 mL NaHCO$_3$, pH 83, containing 9 mg N-acetylglucosamine. To the solution is added 9 mg of Compound 9. After 1 hour the solution is purified by gel filtration. A degree of substitution of 2-3 dyes per molecule is determined from the absorption at 650 nm.

A 1 mg/mL stock solution of the resulting wheat germ agglutinin (WGA) conjugate is prepared in 0.1 M sodium bicarbonate ~pH 8. *Staphylococcus aureus* are cultured for 17 hours at 30° C. in TSB broth. Equal volumes of the TSB culture and a bovine serum albumin (BSA) solution (0.25% BSA+0.85% NaCl sterile filtered through 0.2 μm filter) are incubated at room temperature for 15 minutes. The BSA-bacterial suspension (200 μL) is centrifuged for 2 minutes at 350×g, capturing the bacteria on a filter membrane. The cells are resuspended in 90 μL of BSA solution and 10 μL of stain is added for 15 minutes. Following centrifugation, the bacteria are resuspended in BSA solution, and an aliquot is trapped between a slide and a glass coverslip.

The bacteria are observed on a Nikon Diaphot epifluorescence microscope using an appropriate band pass filter set. Images are acquired using the Star-1 cooled CCD camera and the software package supplied with the camera is used for data analysis. Two images are collected for each stain, each image having a 2 second exposure time. When used according to Sizemore et al. (U.S. Pat. No. 5,137,810) the conjugate can distinguish between Gram-positive and Gram-negative bacteria.

Example 79

Simultaneous Labeling of Actin and Tubulin in Cultured Mammalian Cells

Bovine pulmonary artery cells (BPAEC) are grown to 30-50% of confluence on glass The cells are fixed with 3.7% formaldehyde, permeabilized with 0.2% Triton X-100, and blocked with 6% BSA. The cells are incubated with mouse monoclonal anti-α-tubulin for 60 min.

A cell sample is labeled with a monoclonal mouse anti-tubulin (Molecular Probes, Inc.) and a GAM conjugate of Compound 13 for 30 min, washed, and then incubated with the phalloidin dye-conjugate of Example 64 for an additional 30 min. The cells are rinsed with blocking buffer and mounted in PBS pH 7.4. The stained cells display microtubules decorated with green fluorescence and actin filaments decorated with red fluorescence. Additionally, nuclei can be distinguished by their blue fluorescence when stained with DAPI.

Example 80

Preparation and Use of a Fluorescent α-Bungarotoxin Dye-Conjugate

α-Bungarotoxin (1 mg) in 25 μL 0.1 M NaHCO$_3$ is treated with 1.5 equivalents of the succinimidyl ester of Compound 18 or 1.5 equivalents of Compound 69 at room temperature for 2 hours. The product is purified by size exclusion, by ion exchange chromatography, and finally by reverse-phase HPLC. Staining of acetylcholine receptors and detection of their resulting fluorescence, although detected at a longer wavelength, is comparable to that obtained with TEXAS RED dye-conjugated α-bungarotoxin.

Example 81

Preparation of a Fluorescent Tyramide

A 2-fold molar excess of tyramine hydrochloride is added to Compound 9 in aqueous solution at room temperature followed by an excess of triethylamine After 30 minutes the red solid is precipitated with acetone, washed with ether and purified by preparative HPLC.

Example 82

Peroxidase-Catalyzed Deposition of a Fluorescent Tyramide

Bovine pulmonary artery cells (BPAEC) are grown to 30-50% of confluence on glass The cells are fixed with 3.7% formaldehyde, permeabilized with 0.2% Triton X-100, and blocked with 1 mg/mL streptavidin and 1 mM biotin. After washing, cells are exposed to ~0.05 μg/mL of biotinylated anti-cytochrome c oxidase (anti-COX) (Molecular Probes) then incubated with Streptavidin-HRP conjugate (Molecular Probes) for 60 minutes at room temperature or 37° C. Cells are rinsed again. The sample is then incubated with Compound 9 tyramide (synthesized as described in Example 81) and examined using fluorescence microscopy (Cy5 filter set, Omega XF47). A bright fluorescence emission localized on the mitochondria is obtained, indicating the successful molecular targeting of COX by the Compound 9 tyramide.

Example 83

Preparation of Aminodextran Dye-Conjugates 70,000 MW aminodextran (50 mg) derivatized with an average of 13 amino groups is dissolved at 10 mg/mL in 0.1 M $NaHCO_3$. Compound 13 or 69 is added so as to give a dye/dextran ratio of ~12. After 6 hours the conjugate is purified on SEPHADEX G-50, eluting with water. Typically 4-6 moles of dye are conjugated to 70,000 MW dextran.

Example 84

Preparation of Fluorescent-Dye Labeled Microspheres

Uniform microspheres are conjugated to the dyes of the invention by one of four methods In Method A, 1.0 μm amine-derivatized polystyrene microspheres are suspended at ~2% solids in 100 mM $NaHCO_3$, pH 8.3 and treated with 2 mg/mL of an amine-reactive dye. After 1 hour the microspheres are centrifuged and washed with buffer.

In Method B, carboxylate-modified microspheres are suspended in a solution of a protein that has been conjugated to a dye of the invention. The protein is passively adsorbed on the microspheres, and excess protein is removed by centrifugation and washing. Microparticles of a size that cannot be centrifuged are separated from excess protein by dialysis through a semi-permeable membrane with a high MW cutoff or by gel filtration chromatography.

In Method C a dye-labeled protein is covalently coupled through its amine residues to the carboxylate groups of the polymer using ethyl 3-(dimethylaminopropyl)carbodiimide (EDAC).

In Method D, biotinylated microspheres are treated with a streptavidin, avidin or anti-biotin conjugate of a dye of the invention, and the conjugates are isolated as in Method B.

The larger particles can be analyzed for uniformity of staining and brightness using flow cytometry. The microspheres can be further coupled to proteins, oligonucleotides, haptens and other biomolecules for assays using methods well known in the art.

Example 85

Preparation of Fluorescent Liposomes Using Dyes of the Invention

Selected dyes of the invention are sufficiently water soluble to be incorporated into the interior of liposomes by methods well known in the art (J BIOL. CHEM. 257, 13892 (1982) and PROC. NATL. ACAD. SCI. USA 75, 4194 (1978)). Alternatively, liposomes containing dyes of the invention having a lipophilic substituent (e.g. alkyl having 11-22 carbons), within their membranes are prepared by co-dissolving the fluorescent lipid and the unlabeled lipids phospholipid(s) that make up the liposome before forming the liposome dispersion essentially as described by Szoka, Jr. et al. (ANN. REV. BIOPHYS. BIOENG. 9, 467 (1980)).

Example 86

Preparation of Fluorescent Dye-Conjugates of Bacteria

Heat-killed *Escherichia coli* are suspended at 10 mg/mL in pH 8-9 buffer then incubated with 0.5-1.0 mg/mL of an amine-reactive dye, typically a succinimidyl ester derivative. After 30-60 minutes the labeled bacteria are centrifuged and washed several times with buffer to remove any unconjugated dye. Labeled bacteria that are opsonized are taken up by macrophage, as determined by flow cytometry.

Example 87

Preparation of Nucleotide Dye-Conjugates

To 2 mg of 5-(3-aminoallyl)-2'-deoxyuridine 5'-triphosphate (Sigma Chemical) in 100 μL water is added Compound 9 or 69 in 100 μL DMF and 5 μL triethylamine. After 3 hours, the solution is evaporated and the residue is purified by HPLC. The product fractions are lyophilized to give the red-fluorescent nucleotide conjugate.

Alternatively, fluorescent dye-conjugates of deoxyuridine 5'-triphosphate are prepared from 5-(3-amino-1-propynyl)-2'-deoxyuridine 5'-triphosphate (as described in Hobbs, Jr. et al, supra), or by treating a thiolated nucleotide or a thiophosphate nucleotide with a thiol-reactive dye of the invention (such as the maleimide Compound 11).

Additionally, 2'-(or 3')-2-aminoethylaminocarbonyladenosine 5'-triphosphate is reacted with a slight excess of Compound 9 and, following precipitation with ethanol, the ribose-modified product is purified by preparative HPLC.

Example 88

Preparation of an Oligonucleotide Dye-Conjugate

A 5'-amine-modified, 18-base M13 primer sequence (~100 μg) is dissolved in 4 μL $H_2O$. To this is added 250 μg of Compound 9 or 69 in 100 μL 0.1 M sodium borate, pH 8.5. After 16 hours, 10 μL of 5 M NaCl and 3 volumes of cold ethanol are added. The mixture is cooled to −20° C., centrifuged, the supernatant is decanted, the pellet is rinsed with ethanol and then dissolved in 100 μL $H_2O$. The labeled oligonucleotide is purified by HPLC on a 300 Å C8 reverse-phase column using a ramp gradient of 0.1 M triethylammonium acetate (pH ~7) and acetonitrile (5-95% over 30 min). The desired peak is collected and evaporated to give the fluorescent oligonucleotide.

Example 89

Preparing DNA Hybridization Probes Using Fluorescent Nucleotide Dye-Conjugates For each labeling reaction, a microfuge tube containing about 1 μg of a ~700 bp Hind III-Bgl II fragment of the *E. coli* lacZ structural gene is heated for 10 minutes at 95° C. to fully separate the strands. The DNA is cooled on ice. A 2 µL aliquot of a 2 mg/mL mixture of random sequence hexanucleotides in 0.5 M Tris-HCl, pH 7.2, 0.1 M MgCl$_2$, 1 mM dithiothreitol is added, followed by 2 µL of a dNTP labeling mixture (1 mM dATP, 1 mM dGTP, 1 mM dCTP, 0.65 mM dTTP and 0.35 mM fluorescent dye-labeled dUTP (as prepared in Example 88). Sterile, distilled, deionized water is added to bring the total volume to 19 µL. 1 µL Klenow DNA polymerase (2 units/µL) is added. The samples are incubated 1 hr at 37° C. The reactions are stopped with 2 µL of 0.2 M EDTA, pH 8.0. The labeled DNA is precipitated with 2.5 µL of 4 M LiCl and 75 µL of −20° C. ethanol. After 2 hours at −20° C. the precipitated nucleic acids are centrifuged at 12,000 rpm. The pellets are washed with cold 70% ethanol, then cold 100% ethanol. The pellets are dried and dissolved in 10 mM Tris-HCl, pH 8.0, 1 mM EDTA. A portion of each sample is analyzed by gel electrophoresis on a 1% agarose minigel under standard conditions. The labeled DNA products are suitable for in situ hybridization experiments for the detection of RNA or DNA, such as is associated with the *E. coli* lacZ gene in cells or tissues.

Example 90

Incorporation of Fluorescent Nucleotide Conjugates into DNA Amplification Products A DNA amplification reaction is prepared as follows: 1 µL each of 20 µM solutions of two oligonucleotide primers that hybridize to the human β-actin gene are added to a labeling reaction containing 5 µL DNA template (100 pmol of a plasmid containing the entire gene), 5 µL 10× reaction buffer (100 mM Tris, pH 8.3, 500 mM KCl), 2.5 µL 1 mM fluorescent-labeled dUTP (Example 87), 1 µL 10 mM dATP, 1 µL 10 mM dCTP, 1 µL 10 mM dGTP, 1.5 µL 5 mM dTTP, 3 µL 25 mM MgCl$_2$, and 28 µL distilled, deionized water. The sample is transferred to a thermocycler and processed as follows: one cycle, 94° C., 2.5 minutes; 30 cycles, 94° C., 1 minute, 50° C., 1 minute, 72° C., 1 minute; one cycle, 72° C., 5 minutes; then 4° C. overnight. An aliquot of the sample is mixed with an equal volume of 10% glycerol, loaded onto a 0.9% agarose minigel and electrophoresed. Fluorescent bands of the expected size are visible when the gel is illuminated with 300 nm ultraviolet light.

Example 91

In Situ Hybridization of an RNA Probe

Mouse fibroblasts are fixed and prepared for mRNA in situ hybridization using standard procedures A dye-labeled RNA probe is prepared by in vitro transcription of a plasmid containing the mouse actin structural gene cloned downstream of a phage T3 RNA polymerase promoter. Labeling reactions comprise combining 2 µL DNA template (1 µg DNA), 1 µL each of 10 mM ATP, CTP and GTP, 0.75 µL 10 mM UTP, 2.5 µL 1 mM aminoallyl-labeled UTP (Example 87), 2 µL 10× transcription buffer (400 mM Tris, pH 8.0, 100 mM MgCl$_2$, 20 mM spermidine, 100 mM NaCl), 1 µL T3 RNA polymerase (40 units/µL), 1 µL 2 mg/mL BSA, and 8.75 µL water. Reactions are incubated at 37° C. for two hours.

The DNA template is removed by treatment with 20 units DNase I for 15 minutes, at 37° C. The RNA transcript is purified by extraction with an equal volume of phenol:chloroform, 1:1, then by chromatography on SEPHADEX G50. Labeled RNA is denatured for 5 minutes at 50° C., then hybridized to cellular preparations using standard procedures. The long-wavelength fluorescence of the labeled cells is detected by excitation through an optical filter optimized for Cy5-like dyes (Omega XF47). The spatially integrated fluorescence from the FISH target region (18 separate intensities) as a function of the number of dyes incorporated per base of probe for conjugates of Compound 9 and of Cy5 reveal that conjugates of Compound 9 are brighter than the corresponding Cy5 probe by greater than 50% (at ~13 bases per dye incorporation).

Example 92

Preparing DNA Hybridization Probes Using Fluorescent Platinum Dye (ULS)-Compounds A fluorescent platinum complex (ULS) is prepared from a Compound of the invention and from Cy5 monosuccinimidyl ester by adapting the methods provided in US. Pat. No. 5,714,327 to Houthoff et al. (1998) to yield the compound:

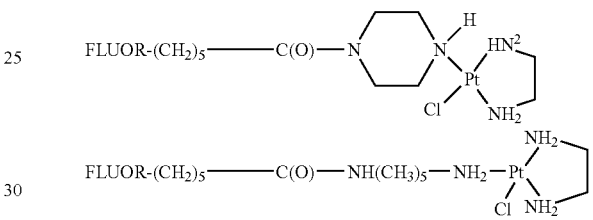

where FLUOR is any of the dye compounds of the invention, attached at its R$^3$ substituent. For each labeling reaction, a microfuge tube containing 1 µg of pUC1.77 plasmid DNA containing a chromosome 1 human α-satellite probe (DNase treated to a fragment size between 500-1000 bp) in 5 mM Tris, pH 8, 1 mM EDTA, is heated for ~10 minutes at 95° C. to fully denature the DNA. The DNA is cooled on ice. 1 µL of a 1 mg/mL solution of the prepared ULS complex is added, followed by the addition of 5 mM Tris, pH 8, 1 mM EDTA to bring the total volume to 25 µL. The samples are incubated 15 minutes at 80° C. The reactions are stopped on ice. The labeled DNA is purified on a Bio-Rad Micro Bio-Spin P-30 Tris Chromatography Column. The labeled DNA products are suitable for in situ hybridization experiments.

A series of Compound 9 ULS and Cy5 ULS DNA hybridization probes are examined with the number of dyes per base varying from 0 per 100 bases, to approximately 8 dyes per hundred bases (FIG. 11). Similar to the behavior of the Cy5 bioconjugates of proteins (Examples 33, 34) and on aminoallyl-labeled DNA (Example 59), the fluorescently quenched 600 nm absorbance band greatly increases at larger numbers of Cy5 dyes per DNA base (equivalent to higher DOS in protein examples) (open circles, FIG. 11), but does not increase with the Compound 9 ULS-labeled DNA (closed circles, FIG. 11).

Example 93

Preparing DNA Hybridization Probes Using Amine-Modified DNA and an Amine-Reactive Dye of the Invention Nick translation is performed using pUC177 plasmid DNA containing a chromosome 1 human α-satellite probe. To a microcentrifuge tube is added, in the following order: 23.5 µL H₂O, 5 µL 10× Nick Translation buffer (0.5 M Tris-HCl, 50 mM MgCl₂, 0.5 mg/mL BSA, pH 7.8), 5 µL 0.1 M DTT, 4 µL d(GAC)TP mix (0.5 mM dATP, 0.5 mM dCTP, 0.5 mM dGTP), 1 µL 0.5 mM dTTP, 4 µL 0.5 mM aminoallyl-dUTP, 1 µL 1 µg/µL template DNA, 5 µL DNase I (1 µg/mL, 2000 Kunitz units/mg), 1.5 µL DNA polymerase I (10 U/µL). The tube is incubated 2 hours at 15° C., then brought to a final volume of 100 µL with H₂O. The amine-modified DNA is purified using a QIAQUICK PCR purification Kit (Qiagen) with the following modifications to purify the DNA from the enzyme and amine-containing Compounds: 75% EtOH is substituted for the wash buffer, H₂O is substituted for the elution buffer, and elution is performed twice for 5 minutes each. The DNA is precipitated by adding ¹/₁₀ volume 3 M sodium acetate and 2.5 volumes 100% EtOH, incubated at −70° C. for 30 minutes, centrifuged for 15 minutes, and washed with 70% EtOH.

The amine-modified DNA is resuspended in 5 µL H₂O. To the solution is added 3 µL 25 mg/mL sodium bicarbonate and 50 µg of Compound 9 or 69 in 5 µL DMF. The reaction is incubated for 1 hour at room temperature in the dark, to the reaction is added 90 µL H₂O, and it is purified using a QIAQUICK PCR purification kit (QIAGEN), with the following modifications: three washes are performed with 75% EtOH and three elutions of 5 minutes each with the QIAGEN elution buffer. The DNA is precipitated as before. The labeled DNA products are suitable for in situ hybridization experiments, use on microarrays and as fluorescence donors or acceptors in hybridization-based assays. A comparison of varying the amino-allyl dUTP to dTTP ratios, followed by subsequent conjugation of the cDNA with either Compound 9 or Cy5 is shown in the Table 5. In the presence of excess reactive dye, both Compound 9 and Cy5 derivatives can label cDNA to equivalent degrees.

TABLE 8

| Nucleotide ratio, AA-dUTP:dTTP | Compound 9 bases/dye | Cy5 bases/dye |
|---|---|---|
| 90 µM:10 µM | 13.2 | 13.6 |
| 60 µM:10 µM | 14.8 | 16.1 |
| 30 µM:10 µM | 17.6 | 15 |
| 10 µM:10 µM | 18.1 | 18.9 |
| 3 µM:10 µM | 23.3 | 23.7 |
| 1 µM:10 µM | 30.2 | 32.2 |

Example 94

Comparison of the Absorbance and Fluorescence Characteristics of Nucleic Acids Prepared as in Example 93 from Compound 9 and from Cy5 Monosuccinimidyl Ester Nucleic acid conjugates of Compound 9 and of Cy5 monosuccinimidyl ester are prepared from the same batch of amine-substituted nucleic acid. Using the above protocol, it is possible to select a dye-labeling ratio that is essentially identical for both the Cy5 derivative and the Compound 9 derivative (e.g., 1 dye per 23 to 24 bases, Table 5). Absorption spectra at the same nucleic acid concentration and dye labeling ratio show a shifting of extinction from the long-wavelength 650 nm band to a non-emitting 600 nm band for the Cy5 conjugate relative to the conjugate of Compound 9 (FIG. 12). This result is very similar to the absorbance changes observed for Cy5 conjugates of proteins (FIGS. 2, 3). Fluorescence emission spectra excited at 600 nm reveal ~4× greater fluorescence of the conjugate of Compound 9 cDNA relative to the Cy5 cDNA conjugate (FIG. 12).

To further prove that it is the behavior of the Cy5 when derivatized onto the cDNA that causes the large increase in the 600 nm absorbance band and decrease in the 650 nm absorbance, the synthesized Cy5 labeled cDNA is digested with micrococcal nuclease (EC 3.1.31.1; Worthington Biochemicals). The enzyme is dissolved at 1.0 mg/mL in reagent-grade water and diluted to approximately 0.001 mg/mL in 0.1% bovine serum albumin prior to addition to the Cy5 dye- and Compound 9-labeled cDNA's, pH=8.8, 0.1 M sodium borate, 0.01 M calcium chloride. The reaction is allowed to proceed at room temperature for 4 hours.

A comparison of the absorbance spectra of the identical labeled cDNA before and after treatment with the nuclease (which will digest the cDNA to dNMP's) is shown in FIG. 13. One can clearly see that the distortion in the absorbance of the Cy5-cDNA conjugate can be eliminated by digesting the cDNA down to its individual deoxynucleoside monophosphates.

There is a concomitant increase in the fluorescence of the Cy5 cDNA upon digestion of ~15×, revealing that this absorbance pattern change is associated with the large decrease in the fluorescence associated with the Cy5-cDNA conjugate.

Example 95

Discrimination of Live and Dead Cells Using the Dyes of the Invention

Selected dyes of the invention are highly polar and therefore relatively impermeant to the membranes of live cells These dyes can therefore be used to discriminate cells that have intact versus compromised cell membranes in a single-color assay as follows: Mouse monocyte-macrophage, Abelson Leukemia Virus Transformed (RAW264.7) cells are trypsinized and washed with PBS, pH 7.2. Approximately 8-10 million cells suspended in 180 µL of PBS, pH 7.2 are placed in a glass test tube and heated in a water bath at 50° C. for 20 minutes to kill a fraction of the cells. Approximately 60 µL (2-3 million cells) of the cell suspension is added to 940 µL of PBS, pH 7.2, followed by 0.1 µL of a 1 mg/mL solution of a succinimidyl ester derivative of a dye of the invention in DMSO. The mixture is incubated on ice for 30 minutes and washed twice with PBS, followed by addition of 200 µL of PBS, pH 7.2. An identical aliquot of cells is treated with 2 µL of a 150 µM solution of propidium iodide in water (as a control for dead cells). Analysis of the cell suspension using flow cytometry shows that populations of dead cells stained by the instant Compounds and those stained by propidium iodide are very similar.

Example 96

Staining Cells with Tandem Dye-Labeled Streptavidin

Jurkat cells are washed twice with 1% BSA/PBS and resuspended at a concentration of 1×10⁷ cells/mL The Jurkat cells are then incubated on ice for 60 minutes with Mouse anti-Human CD4 Biotin (Biosource International) at the recommended concentration of 10 µL for 1×10⁶ cells. After incubation with the primary antibody, the cells are washed with 1% BSA/PBS and incubated on ice for 30 minutes with 1 µg of either the fluorescent streptavidin-phycoerythrin conjugate of Example 40, or a streptavidin conjugate of GIBCO'S RED 670. The cells are washed with 1% BSA/PBS, centrifuged, and resuspended with 400 μL of 1% BSA/PBS. The samples are analyzed on a FacsVantage flow cytometer exciting with the 488-nm line of an argon laser, collecting the emission by a 700-nm long pass filter (XF-48). Using a FSC versus SSC dot plot the live cells are gated and the geometric mean of the fluorescence for FL3 is measured. The data is analyzed for both fluorescence and signal/noise ratio. The cells stained with a conjugate of the invention exhibit a signal-to-noise ratio approximately 13% greater than those labeled with GIBCO RED 670.

It is to be understood that, while the foregoing invention has been described in detail by way of illustration and example, numerous modifications, substitutions, and alterations are possible without departing from the spirit and scope of the invention as described in the following claims.

What is claimed is:

1. A method of staining a biological sample, comprising: combining a dye solution comprising a compound having the formula:

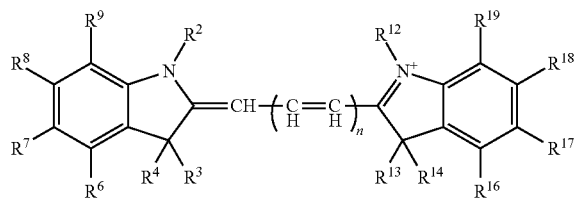

and its salts, wherein,
$R^2$ is alkyl or sulfoalkyl;
$R^{12}$ is alkyl or sulfoalkyl;
$R^3$ is carboxyalkyl or —$(CH_2)_d(CONH(CH_2)_e)_{z'}$—$R_x$, wherein $R_x$ is a carboxylic acid, a succinimidyl ester of a carboxylic acid, a hydrazide, or a maleimide; d is 0-5; e is 1-5; and z' is 0 or 1;
$R^4$ is alkyl;
$R^{13}$ is alkyl or sulfoalkyl;
$R^{14}$ is alkyl or sulfoalkyl;
$R^6$ is selected from hydrogen or sulfo;
$R^7$ is selected from hydrogen or sulfo;
$R^8$ is selected from hydrogen or sulfo;
$R^9$ is selected from hydrogen or sulfo;
$R^{16}$ is selected from hydrogen or sulfo;
$R^{17}$ is selected from hydrogen or sulfo;
$R^{18}$ is selected from hydrogen or sulfo;
$R^{19}$ is selected from hydrogen or sulfo;
wherein sulfo is sulfonic acid or sulfonate; and
n is 1, 2, or 3;
with a biological sample in a concentration sufficient to yield a detectable optical response under desired conditions.

2. The method of claim 1, wherein $R^2$ is sulfoalkyl.
3. The method of claim 1, wherein $R^{12}$ is alkyl.
4. The method of claim 1, wherein $R^{12}$ is ethyl.
5. The method of claim 1, wherein $R^4$ is methyl.
6. The method of claim 1, wherein $R^{14}$ is methyl.
7. The method of claim 1, wherein each of the sulfoalkyl groups are sulfopropyl groups.
8. The method of claim 1, wherein $R^7$ and $R^{17}$ are sulfo.
9. The method of claim 1, wherein n is 1.
10. The method of claim 1, wherein n is 2.
11. The method of claim 1, wherein $R^3$ is —$(CH_2)_d(CONH(CH_2)_e)_{z'}$—$R_x$, wherein $R_x$ is a succinimidyl ester of a carboxylic acid.
12. The method of claim 10, wherein; d is 3 or 5 and z' is 0.

13. The method of claim 1, wherein $R^3$ is —$(CH_2)_d(CONH(CH_2)_e)_{z'}$—$R_x$, wherein $R_x$ is a maleimide.
14. The method of claim 12, wherein d is 3 or 5; e is 2; and z' is 1.
15. The method of claim 1, wherein $R^{16}$ is alkyl.
16. The method of claim 1, wherein the salt is sodium.
17. The method according to claim 1, wherein the compound has the formula:

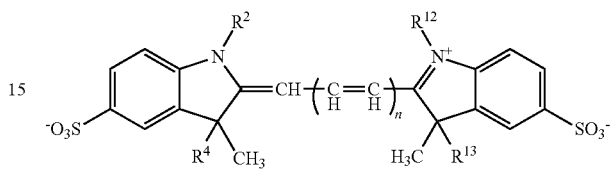

and its salts, wherein,
$R^2$ is alkyl or sulfoalkyl;
$R^{12}$ is alkyl or sulfoalkyl;
$R^3$ is carboxyalkyl or —$(CH_2)_d(CONH(CH_2)_e)_{z'}$—$R_x$, wherein $R_x$ is a carboxylic acid, a succinimidyl ester of a carboxylic acid, a hydrazide, or a maleimide; d is 0-5; e is 1-5; and z' is 0 or 1;
$R^{13}$ is sulfoalkyl;
wherein sulfo is sulfonic acid or sulfonate; and
n is 1, 2 or 3.

18. The method according to claim 1, wherein the compound has the formula:

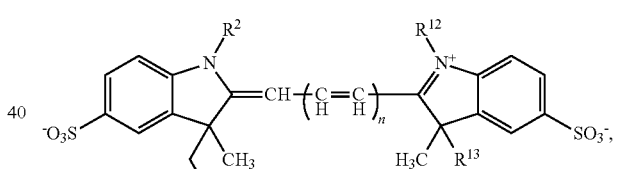

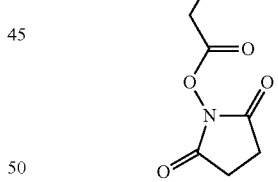

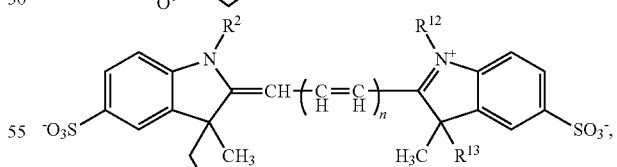

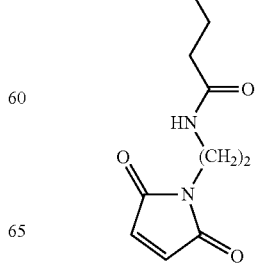

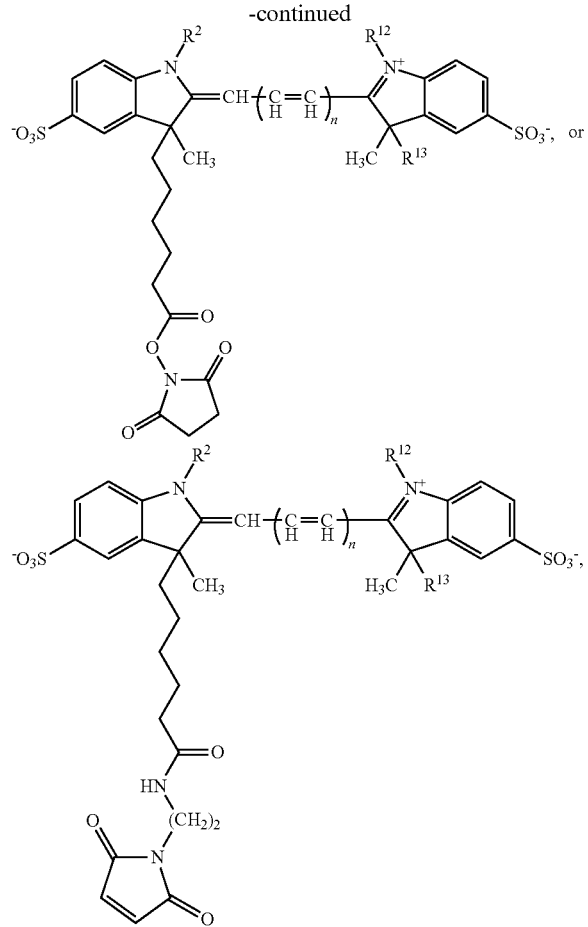

or a salt thereof, wherein,
$R^2$ is alkyl or sulfoalkyl;
$R^{12}$ is alkyl or sulfoalkyl;
$R^{13}$ is alkyl or sulfoalkyl;
wherein sulfo is sulfonic acid or sulfonate; and
n is 1, 2 or 3.

19. The method according to claim 1, wherein the sample comprises cells, proteins, or nucleic acid polymers.

20. The method according to claim 1, wherein the sample is contained in or on a solid or semi-solid matrix that is a membrane, an electrophoretic gel, silicon chip, a glass slide, a microwell plate or a microfluidic chip.

21. A method for forming a dye-conjugate of a protein, peptide, or a nucleic acid polymer, said method comprising:
combining a dye solution comprising a compound of the formula:

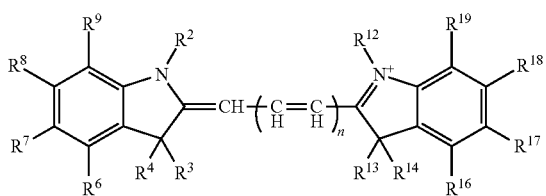

and its salts, wherein,
$R^2$ is alkyl or sulfoalkyl;
$R^{12}$ is alkyl or sulfoalkyl;
$R^3$ is carboxyalkyl or —$(CH_2)_d(CONH(CH_2)_e)_{z'}$—$R_x$, wherein $R_x$ is a carboxylic acid, a succinimidyl ester of a carboxylic acid, a hydrazide, or a maleimide; d is 0-5; e is 1-5; and z' is 0 or 1;
$R^4$ is alkyl;
$R^{13}$ is alkyl or sulfoalkyl;
$R^{14}$ is alkyl or sulfoalkyl;
$R^6$ is selected from hydrogen or sulfo;
$R^7$ is selected from hydrogen or sulfo;
$R^8$ is selected from hydrogen or sulfo;
$R^9$ is selected from hydrogen or sulfo;
$R^{16}$ is selected from hydrogen or sulfo;
$R^{17}$ is selected from hydrogen or sulfo;
$R^{18}$ is selected from hydrogen or sulfo;
$R^{19}$ is selected from hydrogen or sulfo;
wherein sulfo is sulfonic acid or sulfonate; and
n is 1, 2, or 3;
with a sample comprising a protein, peptide, or a nucleic acid polymer whereby a dye conjugate is formed.

22. A kit for fluorescent labeling of a biological sample, comprising:
a dye solution comprising a compound having the formula:

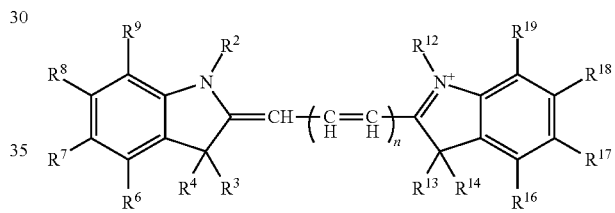

and its salts, wherein,
$R^2$ is alkyl or sulfoalkyl;
$R^{12}$ is alkyl or sulfoalkyl;
$R^3$ is carboxyalkyl or —$(CH_2)_d(CONH(CH_2)_e)_{z'}$—$R_x$, wherein $R_x$ is a carboxylic acid, a succinimidyl ester of a carboxylic acid, a hydrazide, or a maleimide; d is 0-5; e is 1-5; and z' is 0 or 1;
$R^4$ is alkyl;
$R^{13}$ is alkyl or sulfoalkyl;
$R^{14}$ is alkyl or sulfoalkyl;
$R^6$ is selected from hydrogen or sulfo;
$R^7$ is selected from hydrogen or sulfo;
$R^8$ is selected from hydrogen or sulfo;
$R^9$ is selected from hydrogen or sulfo;
$R^{16}$ is selected from hydrogen or sulfo;
$R^{17}$ is selected from hydrogen or sulfo;
$R^{18}$ is selected from hydrogen or sulfo;
$R^{19}$ is selected from hydrogen or sulfo;
wherein sulfo is sulfonic acid or sulfonate; and
n is 1, 2, or 3;
and a buffer.

23. The kit of claim 21, further comprising instructions for fluorescent labeling a biological sample.

24. A composition comprising a compound having the formula:

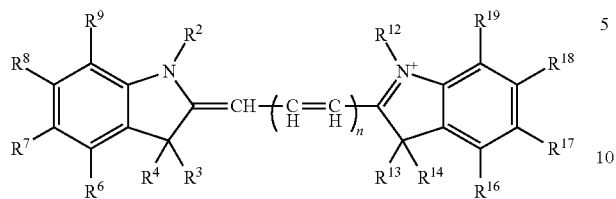

and its salts, wherein,
$R^2$ is alkyl or sulfoalkyl;
$R^{12}$ is alkyl or sulfoalkyl;
$R^3$ is carboxyalkyl or —$(CH_2)_d(CONH(CH_2)_e)_{z'}$—$R_x$, wherein $R_x$ is a carboxylic acid, a succinimidyl ester of a carboxylic acid, a hydrazide, or a maleimide; d is 0-5; e is 1-5; and z' is 0 or 1;
$R^4$ is alkyl;
$R^{13}$ is alkyl or sulfoalkyl;
$R^{14}$ is alkyl or sulfoalkyl;
$R^6$ is selected from hydrogen or sulfo;
$R^7$ is selected from hydrogen or sulfo;
$R^8$ is selected from hydrogen or sulfo;
$R^9$ is selected from hydrogen or sulfo;
$R^{16}$ is selected from hydrogen or sulfo;
$R^{17}$ is selected from hydrogen or sulfo;
$R^{18}$ is selected from hydrogen or sulfo;
$R^{19}$ is selected from hydrogen or sulfo;
wherein sulfo is sulfonic acid or sulfonate; and
n is 1, 2, or 3;
and a protein, peptide, or a nucleic acid polymer.

* * * * *